United States Patent
Leroy et al.

(10) Patent No.: US 8,618,287 B2
(45) Date of Patent: Dec. 31, 2013

(54) DERIVATIVES OF TRIAZINES AND URACILS, THEIR PREPARATION AND THEIR APPLICATION IN HUMAN THERAPEUTICS

(75) Inventors: Isabelle Leroy, Saix (FR); Elisabeth Dupont-Passelaigue, Castres (FR); Karine Valeille, Palaiseau (FR); Yves Rival, Lagarrigue (FR); Didier Junquero, Castres (FR)

(73) Assignee: Pierre Fabre Medicament, Boulogne-Billancourt (FR)

( * ) Notice: Subject to any disclaimer, the term of this patent is extended or adjusted under 35 U.S.C. 154(b) by 167 days.

(21) Appl. No.: 13/054,293

(22) PCT Filed: Jul. 7, 2009

(86) PCT No.: PCT/EP2009/058609
§ 371 (c)(1),
(2), (4) Date: Jan. 14, 2011

(87) PCT Pub. No.: WO2010/006962
PCT Pub. Date: Jan. 21, 2010

(65) Prior Publication Data
US 2011/0118266 A1      May 19, 2011

(30) Foreign Application Priority Data
Jul. 15, 2008   (FR) ...................................... 08 54794

(51) Int. Cl.
| | |
|---|---|
| C07D 403/04 | (2006.01) |
| C07D 403/14 | (2006.01) |
| C07D 401/14 | (2006.01) |
| C07D 253/075 | (2006.01) |
| A61K 31/4523 | (2006.01) |
| A61K 31/496 | (2006.01) |
| A61P 3/04 | (2006.01) |
| A61P 3/10 | (2006.01) |

(52) U.S. Cl.
USPC ........... 544/182; 514/242; 514/228.8; 544/96

(58) Field of Classification Search
USPC .......................................... 544/182; 514/242
See application file for complete search history.

(56) References Cited

FOREIGN PATENT DOCUMENTS

WO    WO 2005/080354 A1    9/2005

OTHER PUBLICATIONS

Freshney et al.,Culture of Animal Cells, A Manual of Basic Technique, Alan R. Liss, Inc., 1983, New York, p. 4.*
Dermer et al., Bio/Technology, 1994, 12:320.*
Dobrzyn et al., Journal of Phisiology and Pharmacology, 57, Suppl. 10, 31-42, 2006.*
Flowers et al., Current Opinion in Lipidology, 19, 248-256, 2008.*
Attie et al.; "Relationship Between Stearoyl-CoA Desaturase Activity and Plasma Triglycerides in Human and Mouse Hypertriglyceridemia"; Journal of Lipid Research, vol. 43, 2002, pp. 1899-1907.
Biddinger et al.; Leptin Suppresses Stearoyl-CoA Desaturase 1 by Mechanisms Independent of Insulin and Sterol Regulatory Element-Binding Protein-1c; Diabetes, vol. 55, 2006, pp. 2032-2041.
Chemical Abstract XP-002518360, Chemcats 2049088870, Jun. 13, 2008.
Cohen et al.; Role for Stearoyl-CoA Desaturase-1 in Leptin-Mediated Weight Loss; Science, vol. 297, 2002, pp. 240-243.
Grundy; "Drug Therapy of the Metabolic Syndrome: Minimizing the Emerging Crisis in Polypharmacy"; Nature Reviews, vol. 5, 2006, pp. 295-309.
Hulver et al.; "Elevated Stearoyl-CoA desaturase-1 Expression in Skeletal Muscle Contributes to Abnormal Fatty Acid Partitioning in Obese Humans"; Cell Metabolism, vol. 2, 2005, pp. 251-261.
Jorgensen et al.; A Suprising Ring Opening Mechanism in the Formation of • -D-Arabinofuranosyl Nucleosides from 5-Substituted Uracils; Synthesis, 1992, pp. 1299-1306, XP-002518359.
Miyazaki et al.; "A Lipogenic Diet in Mice with a Disruption of the Stearoyl-CoA Desaturase 1 Gene Reveals a Stringent Requirement of Endogenous Monounsaturated Fatty Acids for Triglyceride Synthesis"; Journal of Lipid Research, vol. 42, 2001, pp. 1018-1024.
Ntambi et al.; Loss of Stearoyl-CoA Desaturase-1 Function Protects Mice Against Adiposity; PNAS, vol. 99, No. 17, 2002, pp. 11482-11486.
Okada et al.; "Plasma Palmitoleic Acid Content and Obesity in Children 1-3"; Am J Clin Nutr 2005, 82, pp. 747-750.

* cited by examiner (Continued)

Primary Examiner — Venkataraman Balasubramanian
(74) Attorney, Agent, or Firm — Birch, Stewart, Kolasch & Birch, LLP

(57) ABSTRACT

The present invention relates to derivatives of general formula I wherein: —W represents nitrogen, —$R_1$ represents: •a hydrogen or a linear or branched $C_1$-$C_5$ alkyl radical or, •a $C_1$-$C_3$ alkyl radical substituted with groups such as trifluoromethyl, nitrile, hydroxy, $C_1$-$C_3$ alcoxy, $C_3$-$C_6$ alkoxyalkoxy, indolyl, thiophenyl, oxothiophenyl, $C_1$-$C_3$ N-alkylcarbamoyl groups or, •a phenyl or pyridyl or naphthyl, or thiophenyl group optionally substituted with one or more groups such as halogen atoms, nitro, nitrile, trifluoromethyl, vinyl, methylsulfanyl, linear branched $C_1$-$C_4$ alkyl, linear or branched $C_1$-$C_3$ alkoxy groups, •a $C_6$ 2-oxocycloalkyl radical—$R_2$ represents a methyl or heptyl, -m, n are equal to 1, —V represents $CH_2$, —X—Y represents —N— (C=O)—, —CH—O—, —Z represents a phenyl group substituted with one or more trifluoromethyl groups, halogen atoms or linear $C_1$-$C_4$ alkyl groups.

(I)

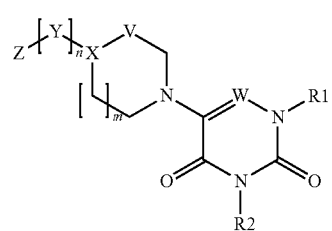

22 Claims, No Drawings

DERIVATIVES OF TRIAZINES AND URACILS, THEIR PREPARATION AND THEIR APPLICATION IN HUMAN THERAPEUTICS

The object of the present invention is derivatives of triazines and uracils inhibiting the activity of the SCD-1 enzyme and their application in human therapeutics.

The metabolic syndrome is the result of increased peripheral resistance to insulin, and is characterized by obesity, intolerance to glucose, certain dyslipidemias which may be associated with arterial hypertension and vascular inflammation. The conjunction of these multiple risk factors promotes development of atheromatous pathology at the origin of thrombotic episodes and to the development of peripheral, coronary, cerebrovascular and arterial diseases (Grundy, S. M. Drug therapy of the metabolic syndrome: minimizing the emerging crisis in polypharmacy. *Nat Rev Drug Discov* 5, 295-309 (2006)).

Stearoyl-CoA Desaturase-1 (SCD-1), also called Δ9-desaturase, is an enzyme which limits the synthesis of monounsaturated fatty acids under the control of the transcription factor $SREBP_{1C}$ (Miyazaki, M., Kim, Y. C., Ntambi, J. M. A lipogenic diet in mice with a disruption of the stearoyl-CoA desaturase-1 gene reveals a stringent requirement of endogenous monounsaturated fatty acids for triglyceride synthesis. *J Lipid Res* 42, 1018-1024 (2001)). Invalidation of the SCD-1 gene in mice makes it resistant to genetic obesity or obesity induced by diet; the peripheral effect of leptin on the increase of energy expense, weight loss and sensitivity to insulin are inversely correlated with the expression of the SCD-1 gene and with the enzymatic activity (Cohen, P., Miyazaki, M., Socci, N. D. et al. Role for stearoyl-CoA desaturase-1 in leptin-mediated weight loss. *Science* 297, 240-243 (2002), Ntambi, J. M., Miyazaki, M., Stoehr, J. P. et al. Loss of stearoyl-CoA desaturase-1 function protects mice against adiposity. *Proc Natl Acad Sci* 99, 11482-11486 (2002), Biddinger, S. B., Miyazaki, M., Boucher, J. et al. Leptin suppresses stearoyl-CoA desaturase-1 by mechanisms independent of insulin and sterol regulatory element-binding protein-1c. *Diabetes* 55, 2032-2041 (2006)).

The involvement of SCD-1 in the pathogenesis of obesity is reinforced by the correlation between plasma concentration of palmitoleic acid and abdominal adiposity in children (Okada, T., Furuhashi, N., Kuromori, Y. et al. Plasma palmitoleic acid content and obesity in children. *Am J Clin Nutr* 82, 747-750 (2005)), the association of over-expression of SCD-1 in the skeletal muscle in obese adults with a bad distribution of fatty acids which causes inhibition of hepatic β-oxidation (Hulver, M. W., Berggren, J. R., Carper, M. J. et al. Elevated stearoyl-CoA desaturase-1 expression in skeletal muscle contributes to abnormal fatty acid partitioning in obese humans. *Cell Metab* 2, 251-261 (2005)). The plasma ratio 18:1/18:0, also called the "desaturation index", appears as the biomarker of SCD-1 activity in humans and correlates with the plasma triglyceride level and in an inversely proportional way with the level of HDL (Attie, A. D., Krauss, R. M., Gray-Keller, M. P. et al. Relationship between stearoyl-CoA desaturase activity and plasma triglycerides in human and mouse hypertriglyceridemia. *J Lipid Res* 43, 1899-1907 (2002)). Accordingly, inhibition of SCD-1 appears as a therapeutic target of choice in the treatment of obesity, of type 2 diabetes and of lipid disorders related to the metabolic syndrome.

The compounds of the invention are characterized by their property of inhibiting the activity of the SCD-1 enzyme and by their pharmacological profile.

The compounds of the invention correspond to the general formula I.

The invention relates to the derivatives of 2H-[1,2,4]triazine-3,5-dione and of H-pyrimidine-2,4-dione for their use as inhibitors of the activity of the SCD-1 enzyme and corresponding to the general formula I:

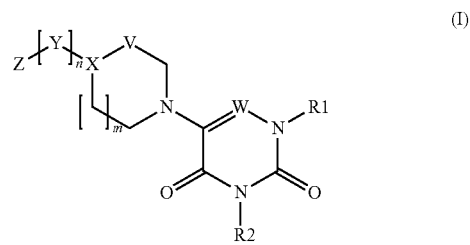

(I)

wherein:
W represents nitrogen or CH
$R_1$ and $R_2$ represent independently of each other:
  a hydrogen or
  a linear or branched $C_1$-$C_7$ alkyl or alkenyl radical or
  a $C_1$-$C_3$ alkyl radical substituted with groups such as:
    trifluoromethyl, nitrile, hydroxy, $C_1$-$C_3$ alcoxy, $C_3$-$C_6$ alkoxyalkoxy, indolyl, thiophenyl, oxothiophenyl, $C_1$-$C_3$ N-alkyl or N-dialkylcarbamoyl or,
    phenyl or aroyl or benzyloxy or N-arylcarbamoyl (for which the phenyl ring is optionally substituted with one or more groups such as a linear or branched $C_1$-$C_4$ alkyl, nitro group, a halogen atom),
  a phenyl or pyridyl or naphthyl, or thiophenyl group optionally substituted with one or more groups such as a halogen, a nitro, nitrile, trifluoromethyl, vinyl, methylsulfanyl, linear branched $C_1$-$C_4$, alkyl, linear or branched $C_1$-$C_3$ alkoxy, phenyl, $C_1$-$C_3$N-mono- or di-alkylcarbamoyl ou dialkylcarbamoyle, $C_1$-$C_4$ alkylcarboxamido group,
  a $C_5$-$C_6$ 2-oxocycloalkyl radical optionally fused with a phenyl group,
m is equal to 0 or 1
V represents $CH_2$, $CHCH_3$ or C=O
when n=1
  X—Y represents —N—(C=O)—, —N—$CH_2$—, —CH—$CH_2$—, —CH—O—, —CH—(C=O)—,
  Z represents a phenyl group optionally substituted with one or more trifluoromethyl groups, halogens, linear or branched $C_1$-$C_4$ alkyl, linear or branched $C_1$-$C_3$ alkoxy groups,
when n=0
  X represents N,
  Z represents a phenyl or cinnamyl or aryloxycarbonyl or 2-phenylacetyl group (the position 2 of which is optionally substituted with a linear or branched $C_1$-$C_4$ alkyl) for which the aromatic group is optionally substituted with one or more trifluoromethyl groups, halogens, linear or branched $C_1$-$C_4$ alkyl, linear or branched $C_1$-$C_3$ alkoxy, nitro groups,
as well as addition salts with pharmaceutically acceptable bases and acids, and the different enantiomers of the compounds having asymmetrical carbons, as well as their mixtures in any proportions notably including the racemic mixtures.

The present invention also relates to novel derivatives of 2H-[1,2,4]triazine-3,5-dione and of H-pyrimidine-2,4-dione, to their preparation and to their application in human therapeutics.

These compounds correspond to the general formula I.

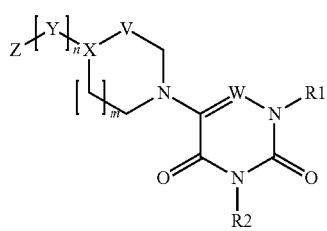

wherein:
W represents nitrogen or CH
$R_1$ and $R_2$ represent:
  a hydrogen in a non-simultaneous way or a linear or branched $C_1$-$C_7$ alkyl or alkenyl radical or,
  a $C_1$-$C_3$ alkyl radical substituted with groups such as: trifluoromethyl, nitrile, hydroxy, $C_1$-$C_3$ alkoxy, $C_3$-$C_6$ alkoxyalkoxy, indolyl, thiophenyl, oxothiophenyl, $C_1$-$C_3$ N-alkyl or N-dialkylcarbamoyl or,
  phenyl or aroyl or benzyloxy or N-arylcarbamoylr (for which the phenyl ring is possibly substituted with one or more groups such as linear or branched $C_1$-$C_4$ alkyl, nitro groups, halogen atoms),
  a phenyl or pyridyl or naphthyl or thiophenyl group, possibly substituted with one or more groups such as halogen atoms, nitro, nitrile, trifluoromethyl, vinyl, methylsulfanyl, linear or branched $C_1$-$C_4$ alkyl, linear or branched $C_1$-$C_3$ alkoxy, phenyl, $C_1$-$C_3$ N-mono- or di-alkylcarbamoyl, $C_1$-$C_4$ alkylcarboxamido groups,
  a $C_5$-$C_6$ 2-oxocycloalkyl radical optionally fused with a phenyl group,
m is equal to 0 or 1
V represents $CH_2$, $CHCH_3$ or $C=O$
when n=1
  X—Y represents —N—(C=O)—, —N—$CH_2$—, —CH—$CH_2$—, —CH—O—, —CH—(C=O)—,
  Z represents a phenyl group substituted with one or more trifluoromethyl groups, halogen atoms, linear or branched $C_1$-$C_4$ alkyl, linear or branched $C_1$-$C_3$ alkoxy groups except for the compounds 6-[4-(4-isopropyl-benzyl)-piperazin-1-yl]-2,4-dimethyl-2H-[1,2,4]triazine-3,5-dione and 2,4-dimethyl-6-[4-(3-trifluoro-methyl-benzyl)-piperazin-1-yl]-2H-[1,2,4]triazine-3,5-dione,
when n=0
  X represents N,
  Z represents a phenyl or cinnamyl or aryloxycarbonyl or 2-phenylacetyl group (the position 2 of which is optionally substituted with a linear or branched $C_1$-$C_4$ alkyl) for which the aromatic group is substituted with one or more trifluoromethyl groups, halogen atoms, linear or branched $C_1$-$C_4$ alkyl, linear or branched $C_1$ or $C_3$ alkoxy, nitro groups, and this except for the following compounds:
6-[4-(4-fluoro-phenyl)-piperazin-1-yl]-2,4-dimethyl-2H-[1,2,4]triazine-3,5-dione
6-[4-(4-methoxy-phenyl)-piperazin-1-yl]-2,4-dimethyl-2H-[1,2,4]triazine-3,5-dione
6-[4-(2-chloro-phenyl)-piperazin-1-yl]-2,4-dimethyl-2H-[1,2,4]triazine-3,5-dione
as well as the addition salts with pharmaceutically acceptable bases and acids, and the different enantiomers of the compounds having asymmetrical carbons, as well as their mixtures in any proportions notably including racemic mixtures.

The present invention more particularly relates to derivatives of 2H-[1,2,4]triazine-3,5-dione and of H-pyrimidine-2,4-dione corresponding to the general formula I

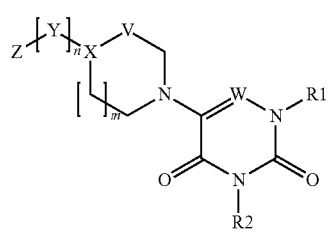

wherein:
W represents nitrogen or CH
$R_1$ and $R_2$ represent:
  a hydrogen (in a non-simultaneous way) or a linear or branched $C_1$-$C_7$ alkyl or alkenyl radical or,
  a $C_1$-$C_3$ alkyl radical substituted with groups such as: trifluoromethyl, nitrile, hydroxy, $C_1$-$C_3$ alkoxy, $C_3$-$C_6$ alkoxyalkoxy, indolyl, thiophenyl, oxothiophenyl, $C_1$-$C_3$ N-alkyl or N-dialkylcarbamoyl groups or,
  phenyl or aroyl or benzyloxy or N-arylcarbamoyl (for which the phenyl ring is optionally substituted with one or more groups such as a linear or branched $C_1$-$C_4$ alkyl, nitro groups, halogen atoms),
  a phenyl or pyridyl or naphthyl or thiophenyl group optionally substituted with one or more groups such as halogen atoms, nitro, nitrile, trifluoromethyl, vinyl, methylsulfanyl, linear or branched $C_1$-$C_4$ alkyl, linear or branched $C_1$-$C_3$ alkoxy, phenyl, $C_1$-$C_3$ N-mono- or di-alkylcarbamoyl, $C_1$-$C_4$ alkylcarboxamido groups,
  a $C_5$-$C_6$ 2-oxocycloalkyl radical optionally fused with a phenyl group,
m,n are equal to 1
V represents $CH_2$
X—Y represents —N—(C=O)—, — —CH—$CH_2$—, —CH—O—, —CH—(C=O)—,
Z represents a phenyl group substituted with one or more trifluoromethyl groups, halogen atoms, linear or branched $C_1$-$C_4$ alkyl, linear or branched $C_1$-$C_3$ alkoxy groups.

The present invention still more particularly relates to the derivatives of 2H-[1,2,4]triazine-3,5-dione and of H-pyrimidine-2,4-dione corresponding to the general formula I

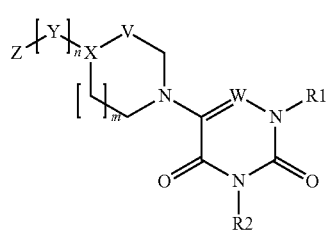

wherein:
W represents nitrogen or CH
$R_1$ and $R_2$ represent:
  a hydrogen (in a non-simultaneous way) or a linear or branched $C_1$-$C_7$ alkyl radical or, a C$_1$-C$_3$ alkyl radical substituted with groups such as: trifluoromethyl, nitrile, hydroxy, C$_1$-C$_3$ alkoxy, C$_3$-C$_6$ alkoxyalkoxy, indolyl, oxothiophenyl, C$_1$-C$_3$ N-alkyl or N-dialkylcarbamoyl groups, a phenyl or pyridyl or naphthyl or thiophenyl group optionally substituted with one or more groups such as halogen atoms, nitro, nitrile, trifluoromethyl, vinyl, methylsulfanyl, linear or branched C$_1$-C$_4$ alkyl, linear or branched C$_1$-C$_3$ alkoxy, C$_1$-C$_3$ N-mono- or di-alkylcarbamoyl, C$_1$-C$_4$ alkylcarboxamido groups, a C$_5$-C$_6$ 2-oxocycloalkyl radical optionally fused with a phenyl group, m,n are equal to 1

V represents CH$_2$

X—Y represents —N—(C=O)—, —CH—O—,

Z represents a phenyl group substituted with one or more trifluoromethyl groups, halogen atoms, linear or branched C$_1$-C$_4$ alkyl groups, The present invention particularly relates to the derivatives of 2H-[1,2,4]triazine-3,5-dione corresponding to the general formula I wherein:

W represents nitrogen,

R$_1$ represents:
a hydrogen or a linear or branched C$_1$-C$_5$ alkyl radical or,
a C$_1$-C$_3$ alkyl radical substituted with groups such as trifluoromethyl, nitrile, hydroxy, C$_1$-C$_3$ alkoxy, C$_3$-C$_6$ alkoxyalkoxy, indolyl, oxothiophenyl, C$_1$-C$_3$ N-alkylcarbamoyl groups,
a phenyl or pyridyl or naphthyl or thiophenyl group optionally substituted with one or more groups such as halogen atoms, nitro, nitrile, trifluoromethyl, vinyl, methylsulfanyl, linear or branched C$_1$-C$_4$ alkyl, linear or branched C$_1$-C$_3$ alkoxy, phenyl, C$_1$-C$_3$ N-mono- or di-alkylcarbamoyl, C$_1$-C$_4$ alkylcarboxamido groups,
a C$_5$-C$_6$ 2-oxocycloalkyl radical, R$_2$ represents: a linear or branched C$_1$-C$_7$ alkyl radical, and preferably a methyl, m,n are equal to 1, V represents CH$_2$, X—Y represents —N—(C=O)—, —CH—O—, Z represents a phenyl group substituted with one or more trifluoromethyl groups, halogen atoms, or linear C$_1$-C$_4$ alkyl groups.

The present invention still more particularly relates to the derivatives of 2H-[1,2,4]triazine-3,5-dione corresponding to the general formula I wherein:

W represents nitrogen,

R$_1$ represents:
a hydrogen or a linear or branched C$_1$-C$_5$ alkyl radical or,
a C$_1$-C$_3$ alkyl radical substituted with groups such as trifluoromethyl, nitrile, hydroxy, C$_1$-C$_3$ alkoxy, C$_3$-C$_6$ alkoxyalkoxy, indolyl, oxothiophenyl, C$_1$-C$_3$ N-alkylcarbamoyl groups,
a phenyl or pyridyl or thiophenyl group possibly substituted with one or more groups such as halogen atoms, nitrile, linear or branched C$_1$-C$_4$ alky, linear or branched C$_1$-C$_3$alkoxy groups,
a C$_6$ 2-oxocycloalkyl radical, R$_2$ represents a methyl or heptyl, m,n are equal to 1, V represents CH$_2$, X—Y represents —N—(C=O)—, —CH—O—, Z represents a phenyl group substituted with one or more trifluoromethyl groups, halogen atoms or linear C$_1$-C$_4$ alkyl groups.

The present invention relates to the compounds of the general formula I characterized in that they are selected from:

4-heptyl-2-methyl-6-[4-(2-trifluoromethyl-benzoyl)-piperazin-1-yl]-2H-[1,2,4]triazine-3,5-dione 2-methyl-6-[4-(2-trifluoromethyl-benzoyl)-piperazin-1-yl]-2H-[1,2,4]triazine-3,5-dione 4-methyl-2-(4,4,4-trifluoro-butyl)-6-[4-(2-trifluoromethyl-benzoyl)-piperazin-1-yl]-2H-[1,2,4]triazine-3,5-dione 4-methyl-6-[4-(2-trifluoromethyl-benzoyl)-piperazin-1-yl]-2H-[1,2,4]triazine-3,5-dione 2,4-dimethyl-6-[4-(2-trifluoromethyl-benzoyl)-piperazin-1-yl]-2H-[1,2,4]triazine-3,5-dione 2,4-dimethyl-6-[4-(2-trifluoromethyl-phenoxy)-piperidin-1-yl]-2H-[1,2,4]triazine-3,5-dione 3-{4-heptyl-3,5-dioxo-6-[4-(2-trifluoromethyl-phenoxy)-piperidin-1-yl]-4,5-dihydro-3H-[1,2,4]triazin-2-yl}-propionitrile 2-butyl-4-methyl-6-[4-(2-trifluoromethyl-phenoxy)-piperidin-1-yl]-2H-[1,2,4]triazine-3,5-dione N-methyl-2-{4-methyl-3,5-dioxo-6-[4-(2-trifluoromethyl-phenoxy)-piperidin-1-yl]-4,5-dihydro-3H-[1,2,4]triazin-2-yl}-acetamide 2-(2-ethoxy-ethyl)-4-methyl-6-[4-(2-trifluoromethyl-phenoxy)-piperidin-1-yl]-2H-[1,2,4]triazine-3,5-dione 2-[2-(1H-indol-3-yl)-ethyl]-4-methyl-6-[4-(2-trifluoromethyl-phenoxy)-piperidin-1-yl]-2H-[1,2,4]triazine-3,5-dione 4-methyl-2-(4-oxo-4-thiophen-2-yl-butyl)-6-[4-(2-trifluoromethyl-phenoxy)-piperidin-1-yl]-2H-[1,2,4]triazine-3,5-dione 3-{6-[4-(2-chloro-phenoxy)-piperidin-1-yl]-4-methyl-3,5-dioxo-4,5-dihydro-3H-[1,2,4]triazin-2-yl}-propionitrile 6-[4-(2-chloro-phenoxy)-piperidin-1-yl]-4-methyl-2-(4,4,4-trifluoro-butyl)-2H-[1,2,4]triazine-3,5-dione 6-[4-(2-chloro-phenoxy)-piperidin-1-yl]-2,4-dimethyl-2H-[1,2,4]triazine-3,5-dione 6-[4-(2-fluoro-phenoxy)-piperidin-1-yl]-2,4-dimethyl-2H-[1,2,4]triazine-3,5-dione 6-[4-(2-chloro-5-trifluoromethyl-phenoxy)-piperidin-1-yl]-2,4-dimethyl-2H-[1,2,4]triazine-3,5-dione 6-[4-(2-chloro-5-fluoro-phenoxy)-piperidin-1-yl]-2,4-dimethyl-2H-[1,2,4]triazine-3,5-dione 2,4-dimethyl-6-(4-o-tolyloxy-piperidin-1-yl)-2H-[1,2,4]triazine-3,5-dione 6-[4-(4-fluoro-phenoxy)-piperidin-1-yl]-2,4-dimethyl-2H-[1,2,4]triazine-3,5-dione 6-[4-(5-fluoro-2-trifluoromethyl-benzoyl)-piperazin-1-yl]-2,4-dimethyl-2H-[1,2,4]triazine-3,5-dione 6-[4-(5-fluoro-2-trifluoromethyl-benzoyl)-piperazin-1-yl]-4-methyl-2-(4,4,4-trifluoro-butyl)-2H-[1,2,4]triazine-3,5-dione 6-[4-(5-fluoro-2-trifluoromethyl-benzoyl)-piperazin-1-yl]-4-methyl-2-(3-methyl-butyl)-2H-[1,2,4]triazine-3,5-dione 2,4-dimethyl-6-[4-(2-trifluoromethyl-benzyl)-piperazin-1-yl]-2H-[1,2,4]triazine-3,5-dione 4-methyl-2-(4,4,4-trifluoro-butyl)-6-[4-(2-trifluoromethyl-benzyl)-piperazin-1-yl]-2H-[1,2,4]triazine-3,5-dione 4-methyl-6-[4-(2-trifluoromethyl-benzyl)-piperazin-1-yl]-2H-[1,2,4]triazine-3,5-dione 6-[4-(5-fluoro-2-trifluoromethyl-benzyl)-piperazin-1-yl]-4-methyl-2H-[1,2,4]triazine-3,5-dione 6-[4-(4-fluoro-2-trifluoromethyl-benzyl)-piperazin-1-yl]-4-methyl-2H-[1,2,4]triazine-3,5-dione 6-[4-(4-fluoro-2-trifluoromethyl-benzyl)-piperazin-1-yl]-4-methyl-2H-[1,2,4]triazine-3,5-dione 2-butyl-4-methyl-6-[4-(2-trifluoromethyl-benzoyl)-piperazin-1-yl]-2H-[1,2,4]triazine-3,5-dione 6-[4-(2-chloro-phenoxy)-piperidin-1-yl]-4-heptyl-2H-[1,2,4]triazine-3,5-dione 4-methyl-2-o-tolyl-6-[4-(2-trifluoromethyl-phenoxy)-piperidin-1-yl]-2H-[1,2,4]triazine-3,5-dione 2-(4-fluoro-phenyl)-4-methyl-6-[4-(2-trifluoromethyl-phenoxy)-piperidin-1-yl]-2H-[1,2,4]triazine-3,5-dione 4-methyl-2-pyridin-3-yl-6-[4-(2-trifluoromethyl-phenoxy)-piperidin-1-yl]-2H-[1,2,4]triazine-3,5-dione 4-methyl-2-thiophen-3-yl-6-[4-(2-trifluoromethyl-phenoxy)-piperidin-1-yl]-2H-[1,2,4]triazine-3,5-dione 4-{4-methyl-3,5-dioxo-6-[4-(2-trifluoromethyl-phenoxy)-piperidin-1-yl]-4,5-dihydro-3H-[1,2,4]triazin-2-yl}-benzonitrile 2-(2-methoxy-phenyl)-4-methyl-6-[4-(2-trifluoromethyl-phenoxy)-piperidin-1-yl]-2H-[1,2,4]triazine-3,5-dione 4-methyl-6-[4-(2-trifluoromethyl-phenoxy)-piperidin-1-yl]-2H-[1,2,4]triazine-3,5-dione 4-methyl-2-(2-oxo-cyclohexyl)-6-[4-(2-trifluoromethyl-phenoxy)-piperidin-1-yl]-2H-[1,2,4]triazine-3,5-dione 2-[2-(2-ethoxy-ethoxy)-ethyl]-4-methyl-6-[4-(2-trifluoromethyl-phenoxy)-piperidin-1-yl]-2H-[1,2,4]triazine-3,5-dione 2-(2-hydroxy-ethyl)-4-methyl-6-[4-(2-trifluoromethyl-phenoxy)-piperidin-1-yl]-2H-[1,2,4]triazine-3,5-dione Synthesis The compounds of the present invention may be synthesized by using the synthesis routes described below or by using synthesis methods known to one skilled in the art.

Method 1

The synthesis of compounds of general formula I is characterized (Scheme 1) in that a derivative of general formula II

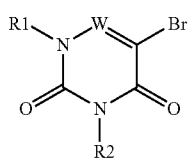

II wherein W, $R_1$ and $R_2$ represent the groups as described earlier in formula I is fused with a derivative of general formula III

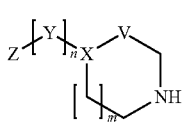

III wherein m, n, X, Y, V, and Z are as described earlier in formula I. This reaction may be conducted in the presence of a base such as triethylamine in n-butanol or toluene or dimethylformamide;

Scheme 1

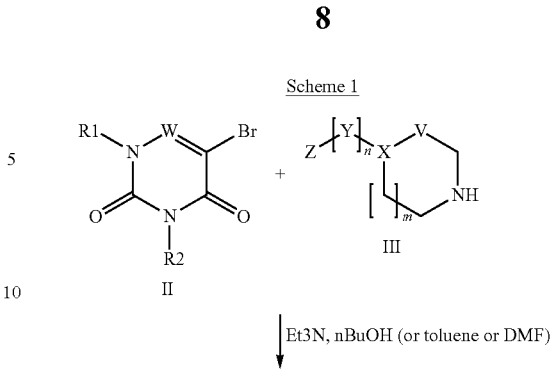

Method 2

This synthesis method for compounds of general formula I (Scheme 2) for which X represents a nitrogen, is characterized in that a derivative of general formula IV

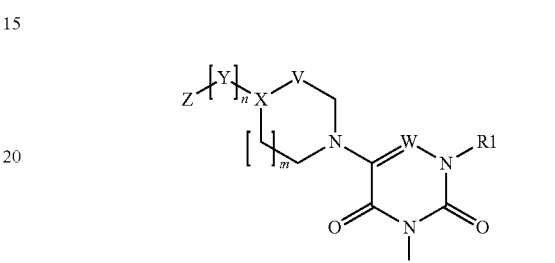

IV wherein m, V, W, $R_1$ and $R_2$ are as described earlier in formula I, is fused with a compound of general formula V

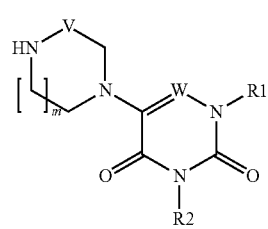

V wherein Hal represents a halogen such as Cl, Br or I, when n=1, Y represents —(C═O)—, —CH$_2$— and Z is as described earlier in formula I, and when n=0, Z represents a cinnamyl or aryloxycarbonyl or 2-phenylethyl group (the position 2 of which is optionally substituted with a linear or branched $C_1$-$C_4$ alkyl) for which the aromatic group is substituted with one or more trifluoromethyl groups, halogen atoms, linear or branched $C_1$-$C_4$ alkyl, linear or branched $C_1$-$C_3$ alkoxy, nitro groups.

This reaction may be carried out in the presence of triethylamine in dichloromethane or in toluene (when Y is —CH$_2$—).

Scheme 2

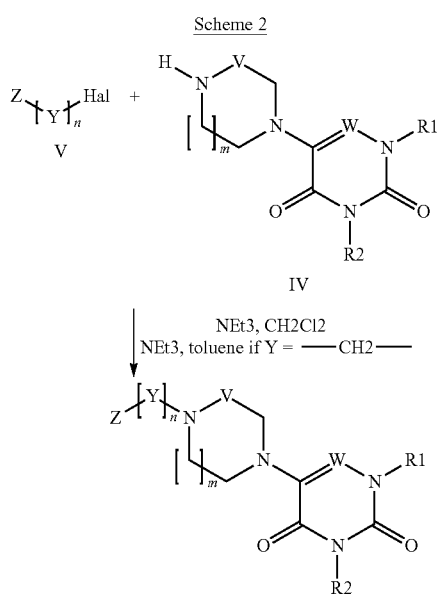

Method 3

This synthesis method of the compounds of general formula I for which W represents a nitrogen (Scheme 3) is characterized in that the nitrogen is alkylated in the position 2 of the compound VI, obtained according to the synthesis method 1 (for R₁ representing a hydrogen)

VI wherein X, Y, V, Z, m, n and R₂ are as described earlier in formula I, by a halogenated derivative of general formula R₁Hal, wherein Hal represents a halogen such as Cl, Br or I and R₁ is as described earlier in general formula I, under operating conditions such as NaH or tBuOK in dimethylformamide.

Scheme 3

VI

↓ NaH, DMF, R1Hal

-continued

The intermediate and final compounds may if desired by purified according to one or several purification methods selected from extraction, filtration, silica gel chromatography, preparative normal or reverse phase HPLC, crystallization.

The raw materials used in the methods described earlier are commercial or easily accessible to one skilled in the art according to methods described in the literature.

The following Examples illustrate the invention without limiting the scope thereof.

Elementary analyses and mass and NMR spectra confirm the structures of the compounds.

INTERMEDIATES 1 a) 6-bromo-2H-[1,2,4]triazine-3,5-dione (1a)

2H-[1,2,4]triazin-3,5-dione (20 g, 177 mmol) is placed in the presence of pyridinium perbromide in 200 mL of water at 90° C. for 4 h. The reaction medium is then extracted with ethyl acetate and the organic phases are dried on MgSO₄. After filtration and dry concentration, 1a is isolated as a white solid (27 g, yield=80%).

TLC silica gel 60 F 254 Merck, CH₂Cl₂-MeOH: 90-10, Rf=0.32.

b) 6-bromo-2,4-dimethyl-2H-[1,2,4]triazine-3,5-dione (1b)

11.8 g (295 mmol) of NaH (at 60% in paraffin) are placed in suspension at 0° C. in 250 mL of DMF under nitrogen. 25.80 g (135 mmol) of intermediate 1a diluted in 150 mL of DMF are poured dropwise. This solution is then placed at room temperature, and then 18.4 mL (296 mmol) of methyl iodide are poured dropwise. After one night of stirring and dry concentration of the reaction medium, the obtained residue is taken up with water and extracted with ethyl acetate. The organic phases are washed with brine, dried on magnesium sulfate and then dry concentrated. The obtained residue, taken up with ether, crystallizes and a first fraction of crystals is isolated. The filtrate is dry concentrated and then purified by flash chromatography on silica (heptane-AcOEt: 50-50). 24 g of intermediate 1b as a solid are thereby isolated (yield 81%).

TLC silica gel 60 F 254 Merck, $CH_2Cl_2$-AcOEt: 80-20, Rf=0.59.

c) 5-bromo-1,3-dimethyl-1H-pyrimidine-2,4-dione (1c)

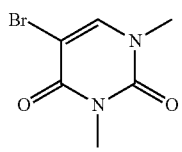

Synthesis of the intermediate 1c is achieved from 5-bromo-1H-pyrimidine-2,4-dione according to the operating procedure described for the synthesis of 1b (solid, yield 82%).

TLC silica gel 60 F 254 Merck, $CH_2Cl_2$-MeOH: 90-10, Rf=0.8.

INTERMEDIATES 2 a) 6-bromo-4-methyl-2H-[1,2,4]triazine-3,5-dione (2a)

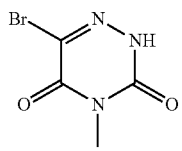

20.3 g (105.7 mmol) of triazine 1a are placed in 150 mL of acetic anhydride under reflux for 4.5 h. After dry concentration of the reaction medium, a precipitate is isolated and then recrystallized from ether: 24.3 g of crystals are isolated (yield=98%). 4.5 g (114.2 mmol) of NaH (60% in paraffin) are placed in 50 mL of DMF under nitrogen. A solution of 24.3 g (103.8 mmol) of crystals isolated earlier, in 150 mL of DMF is poured dropwise. The reaction medium is stirred for 45 min at room temperature and then 7 mL (114.2 mmol) of methyl iodide are added, and stirring then continues for 21 h at room temperature. After dry concentration, the obtained residue is taken up with $H_2O$ and extracted with ethyl acetate. After drying on $MgSO_4$, the organic phases are evaporated and the obtained clear oil is purified by flash chromatography on silica ($CH_2Cl_2$-AcOEt: 90-10). 22.9 g of crystals (yield=89%) are isolated, which are placed in 300 mL of ethanol in the presence of 0.6 g of paratoluene-sulfonic acid. This mixture is heated with reflux for 4.5 h and then dry concentrated. The residue is taken up with $H_2O$ and then extracted with ethyl acetate. After drying and evaporation of the organic phases, 17 g of intermediate 2a are isolated as a solid (yield=89%).

TLC silica gel 60 F 254 Merck, $CH_2Cl_2$-AcOEt: 90-10, Rf=0.29.

b) INTERMEDIATES 2b-2d

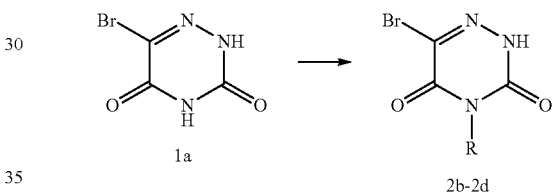

The synthesis of the 2b-2d intermediates is achieved from 1a according to the operating procedure described for the synthesis of 2a by using various alkylation agents RX.

TABLE 1

| | intermediates 2b-2d | | | |
|---|---|---|---|---|
| RX | Total yield | TLC | state | Intermediates 2b-2d |
| F₃C-CH₂CH₂CH₂-I | 76% | $CH_2Cl_2$—AcOEt: 90-10 Rf = 0.45 | solid | 2b: 6-bromo-4-(4,4,4-trifluoro-butyl)-2H-[1,2,4] triazine-3,5-dione |
| C₇H₁₅-Br | 84% | EP—AcOEt: 70-30 Rf = 0.73 | solid | 2c: 6-bromo-4-heptyl-2H-[1,2,4]triazine-3,5-dione |
| PhCH₂-O-CH₂-Cl | 81% | EP—AcOET: 50-50 Rf = 0.61 | solid | 2d: 4-benzyloxymethyl-6-bromo-2H-[1,2,4]triazine-3,5-dione |

TLC: silica gel 60 F. 254 Merck, EP = petroleum ether c) 6-bromo-2-methyl-2H-[1,2,4]triazine-3,5-dione (2e)

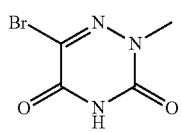

10 g (88 mmol) of 2H-[1,2,4]triazine-3,5-dione are placed in 177 mL of hexamethyldisilazane at room temperature. 17.7 mL (132 mmol) of trimethylsilyl chloride are added. The mixture is heated to 125° C. for 2.5 h and then placed at 60° C. and 55 mL (880 mmol) of methyl iodide are added. The medium is stirred at 60° C. for 15 h. After cooling to 0° C., 400 mL of acetic acid are slowly added. The mixture is left under stirring for 30 min. After dry concentration of the reaction medium, the obtained residue is purified by flash chromatography on silica ($CH_2Cl_2$-MeOH: 95-5). 4.7 g of crystals (yield=43%) are isolated. 4.7 g (37.2 mmol) of the obtained solid are placed in 50 mL of water in the presence of 7.6 mL of bromine (148.8 mmol). The medium is heated to 60° C. for 14 h. The reaction medium is then slowly poured onto a $Na_2SO_3$ 10% solution cooled to 0° C., up to a pH=7. It is then extracted with ethyl acetate and the organic phases are dried on $MgSO_4$. After filtration and dry concentration, 2e is isolated as a white powder (6.6 g, yield=85%).

TLC silica gel 60 F 254 Merck, $CH_2Cl_2$-MeOH: 90-10, Rf=0.75.

INTERMEDIATES 3 a) 3-(6-bromo-4-methyl-3,5-dioxo-4,5-dihydro-3H-[1,2,4]triazin-2-yl)-propionitrile (3a)

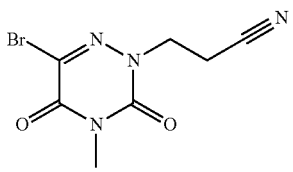

2.4 g (11.6 mmol) of the triazine 2a and 7 mL (106 mmol) of acrylonitrile are placed in 24 mL of a solution of pyridine and water (1/1) under reflux for 3 h. After concentration, the reaction medium is extracted with AcOEt and then after drying on $MgSO_4$, the organic phases are dry concentrated. After washing the obtained solid with ether, 2.8 g of intermediate 3a are obtained (yield=93%).

TLC silica gel 60 F 254 Merck, petroleum ether-AcOEt: 70-30, Rf=0.18.

b) INTERMEDIATES 3b and 3c

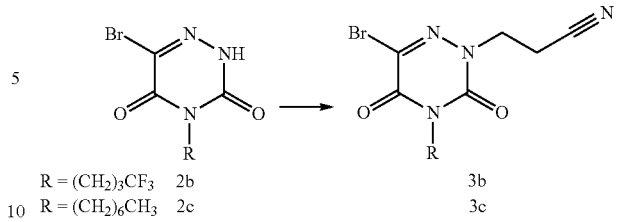

| | |
|---|---|
| R = $(CH_2)_3CF_3$ 2b | 3b |
| R = $(CH_2)_6CH_3$ 2c | 3c |

The synthesis of the intermediates 3b and 3c is achieved from the intermediates 2b and 2c respectively according to the operating procedure described for the synthesis of 3a.

TABLE 2 intermediates 3b and 3c

| Starting synthons | Yield | TLC | State | Intermediates 3b-3c |
|---|---|---|---|---|
| 2b | 91% | EP—AcOEt: 70-30 Rf = 0.34 | solid | 3b: 3-[6-bromo-3,5-dioxo-4-(4,4,4-trifluoro-butyl)-4,5-dihydro-3H-[1,2,4]triazin-2-yl]-propionitrile |
| 2c | 95% | $CH_2Cl_2$—AcOEt: 70-30 Rf = 0.51 | solid | 3c: 3-(6-bromo-4-heptyl-3,5-dioxo-4,5-dihydro-3H-[1,2,4]triazin-2-yl)-propionitrile |

TLC: silica gel 60 F 254 Merck, EP = petroleum ether

INTERMEDIATES 4 a)-6-bromo-4-methyl-2-(4,4,4-trifluoro-butyl)-2H-[1,2,4]triazine-3,5-dione (4a)

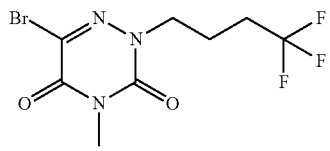 [SMILES: Cn1c(=O)c(Br)nn(CCCC(F)(F)F)c1=O]

0.85 g (21.3 mmol) of NaH (at 60% in paraffin) are placed in 10 mL of DMF under nitrogen. A solution of 4 g (19.4 mmol) of intermediate 2a in 40 mL of DMF is poured dropwise. The reaction medium is stirred for 1 h at room temperature and then 5 g (21.3 mmol) of 1,1,1-trifluoro-4-iodo-butane are added dropwise, and stirring is then continued for 3 h at room temperature. After dry concentration, the obtained residue is taken up with $H_2O$ and extracted with ethyl acetate. After drying on $MgSO_4$, the organic phases are evaporated and the obtained oil is purified by flash chromatography on silica (petroleum ether-AcOEt: 80-20). 5.3 g of crystals corresponding to the compound 4a (yield=87%) are isolated.

TLC silica gel 60 F 254 Merck, petroleum ether-AcOEt: 70-30, Rf=0.58.

b) INTERMEDIATES 4b-4j

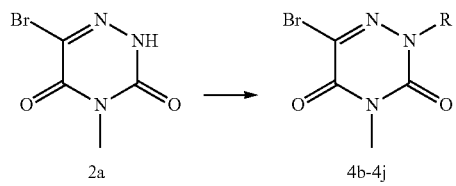

The synthesis of the intermediates 4b-4j is achieved from 2a according to the operating procedure described for the synthesis of 4a by using various alkylation agents RX.

TABLE 3 intermediates 4b-4j

| RX | Total yield | TLC | state | Intermediates 4b-4j |
|---|---|---|---|---|
| phthalimide-N-CH$_2$Br | 88% | EP—AcOEt: 50-50 Rf = 0.37 | solid | 4b: 2-(6-bromo-4-methyl-3,5-dioxo-4,5-dihydro-3H-[1,2,4]triazin-2-ylmethyl)-isoindole-1,3-dione |
| n-butyl iodide | 90% | CH$_2$Cl$_2$—MeOH: 95-5 Rf = 0.82 | solid | 4c: 6-bromo-2-butyl-4-methyl-2H-[1,2,4]triazine-3,5-dione |
| BrCH$_2$C(O)NHCH$_3$ | 65% | CH$_2$Cl$_2$—MeOH: 90-10 Rf = 0.49 | solid | 4d: 2-(6-bromo-4-methyl-3,5-dioxo4,5-dihydro-3H-[1,2,4]triazin-2-yl)-N-methyl-acetamide |
| EtO-CH$_2$CH$_2$-Br | 80% | CH$_2$Cl$_2$—MeOH: 95-5 Rf = 0.76 | oil | 4e: 6-bromo-2-(2-ethoxy-ethyl)-4-methyl-2H-[1,2,4]triazine-3,5-dione |
| 3-(2-bromoethyl)-1H-indole | 54% | CH$_2$Cl$_2$—AcOEt: 95-5 Rf = 0.72 | solid | 4f: 6-bromo-2-[2-(1H-indol-3-yl)-ethyl]-4-methyl-2H-[1,2,4]triazine-3,5-dione |
| isoamyl iodide | 86% | CH$_2$Cl$_2$—AcOEt: 95-5 Rf = 0.79 | oil | 4g: 6-bromo-4-methyl-2-(3-methyl-butyl)-2H-[1,2,4]triazine-3,5-dione |
| 2-nitrophenacyl bromide | 42% | CH$_2$Cl$_2$—AcOEt: 95-5 Rf = 0.61 | solid | 4h: 6-bromo-4-methyl-2-[2-(2-nitro-phenyl)-2-oxo-ethyl]-2H-[1,2,4]triazine-3,5-dione |
| 4-bromo-1-(thiophen-2-yl)butan-1-one | 43% | CH$_2$Cl$_2$—AcOEt: 95-5 Rf = 0.49 | solid | 4i: 6-bromo-4-methyl-2-(4-oxo-4-thiophen-2-yl-butyl)-2H-[1,2,4]triazine-3,5-dione |
| 2-chloro-N-(2-nitrophenyl)acetamide | 79% | CH$_2$Cl$_2$—MeOH: 95-5 Rf = 0.58 | solid | 4j: 2-(6-bromo-4-methyl-3,5-dioxo-4,5-dihydro-3H-[1,2,4]triazin-2-yl)-N-(2-nitro-phenyl)-acetamide |

TLC: silica gel 60 F. 254 Merck, EP = petroleum ether c)-6-bromo-4-methyl-2-(2-thiophen-2-yl-ethyl)-2H-[1,2,4]triazine-3,5-dione (4k)

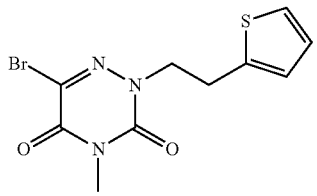 [SMILES: Cn1c(=O)c(Br)nn(CCc2cccs2)c1=O]

0.4 g (1.94 mmol) of intermediate 2a are placed in the presence of 0.24 mL (2.14 mmol) of 2-thiophen-2-yl-ethanol, 0.61 g (2.33 mmol) of triphenylphosphine in 4 mL of THF. At 0° C., 0.54 mL (2.33 mmol) of DEAD in solution in toluene are added dropwise. The reaction medium is heated for 7 h at 70° C. After concentration, the obtained residue is taken up with ethyl acetate and washed with water. After drying on $MgSO_4$, the organic phase is dry concentrated. The obtained residue is purified by flash chromatography on silica ($CH_2Cl_2$/MeOH, gradient 100/0 to 97/3 over 30 min). 0.48 g of crystals corresponding to the compound 4k are obtained (yield: 79%).

d) 6-bromo-4-methyl-2-o-tolyl-2H-[1,2,4]triazine-3,5-dione (4l)

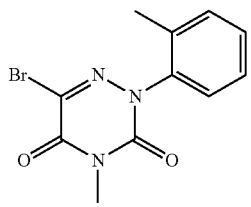 [SMILES: Cc1ccccc1-n1nc(Br)c(=O)n(C)c1=O]

0.5 g (2.43 mmol) of intermediate 2a are placed in the presence of 0.4 mL (4.85 mmol) of pyridine, 0.66 g (4.85 mmol) of o-tolyl boronic acid, 0.66 g (3.64 mmol) of copper acetate in 50 mL of $CH_2Cl_2$. The reaction medium is stirred for 24 h at room temperature and then filtered on celite. The filtrate is washed with water, and then with 0.01N hydrochloric acid. After drying on $MgSO_4$, the organic phase is dry concentrated. After washing the obtained residue with diethyl ether, 0.54 g of a white solid corresponding to the compound 4l are isolated (yield 75%)

e) INTERMEDIATES 4m-4q

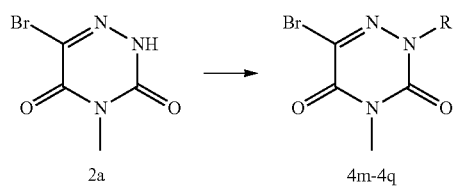

The synthesis of intermediates 4m-4q is achieved from 2a according to the operating procedure described for the synthesis of 4l by using various boronic acids $RB(OH)_2$.

TABLE 4

| intermediates 4m-4q | | | | |
|---|---|---|---|---|
| RB (OH)₂ | Yield | TLC | State | Intermediates 4m-4q |
| 4-fluorophenyl boronic acid | 93% | CH₂Cl₂—AcOEt: 90-10 Rf = 0.61 | solid | 4m: 6-bromo-2-(4-fluoro-phenyl)-4-methyl-2H-[1,2,4]triazine-3,5-dione |
| pyridin-3-yl boronic acid | 62% | EP—AcOEt: 5-5 Rf = 0.2 | solid | 4n: 6-bromo-4-methyl-2-pyridin-3-yl-2H-[1,2,4]triazine-3,5-dione |
| thiophen-3-yl boronic acid | 62% | CH₂Cl₂—AcOEt: 95-5 Rf = 0.62 | solid | 4o: 6-bromo-4-methyl-2-thiophen-3-yl-2H-[1,2,4]triazine-3,5-dione |
| 4-cyanophenyl boronic acid | 74% | CH₂Cl₂—AcOEt: 95-5 Rf = 0.48 | solid | 4p: 4-(6-bromo-4-methyl-3,5-dioxo-4,5-dihydro-3H-[1,2,4]triazin-2-yl)-benzonitrile |

TABLE 4-continued intermediates 4m-4q

| RB(OH)$_2$ | Yield | TLC | State | Intermediates 4m-4q |
|---|---|---|---|---|
| 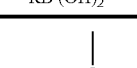 | 38% | CH$_2$Cl$_2$—AcOEt: 95-5<br>Rf = 0.56 | solid | 4q: 6-bromo-2-(2-methoxy-phenyl)-4-methyl-2H-[1,2,4]triazine-3,5-dione |

TLC: silica gel 60 F. 254 Merck, EP = petroleum ether

INTERMEDIATES 5

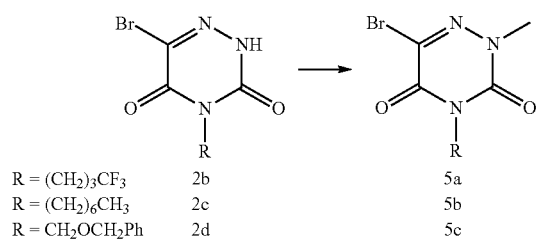

| | |
|---|---|
| R = (CH$_2$)$_3$CF$_3$ | 2b |
| R = (CH$_2$)$_6$CH$_3$ | 2c |
| R = CH$_2$OCH$_2$Ph | 2d |

| | |
|---|---|
| | 5a |
| | 5b |
| | 5c |

The synthesis of the intermediates 5a-5c is achieved from 2b-2d respectively according to the operating procedure described for the synthesis of 4a by using iodomethane as an alkylation agent.

TABLE 5 intermediates 5a-5c

| Starting synthons | Yield | TLC | State | Intermediates 5a-5b |
|---|---|---|---|---|
| 2b | 91% | EP—AcOEt: 70-30<br>Rf = 0.61 | solid | 5a: 6-bromo-2-methyl-4-(4,4,4-trifluoro-butyl)-2H-[1,2,4]triazine-3,5-dione |
| 2c | 92% | CH$_2$Cl$_2$—MeOH: 95-5<br>Rf = 0.65 | oil | 5b: 6-bromo-4-heptyl-2-methyl-2H-[1,2,4]triazine-3,5-dione |
| 2d | 87% | EP—AcOEt: 80-20<br>Rf = 0.49 | solid | 5c: 4-benzyloxymethyl-6-bromo-2-methyl-2H-[1,2,4]triazine-3,5-dione |

TLC: silica gel 60 F 254 Merck, EP = petroleum ether

INTERMEDIATES 6 a) piperazin-1-yl-(2-trifluoromethyl-phenyl)-methanone hydrochloride (6a)

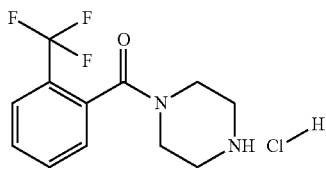

23.44 g (125 mmol) of BOC-piperazine are placed in the presence of 26 mL (186 mmol) of triethylamine in 250 mL de dichloromethane at 0° C. 25 g (119.8 mmol) of 2-trifluoromethyl-benzoyl chloride are added dropwise, the reaction medium is stirred for 30 min at 0° C., and then left with stirring at room temperature for 1 h 30 min. After concentration, the obtained residue is taken up with AcOEt, washed with water, and then with water saturated with NaCl. After drying on MgSO$_4$, the organic phases are dry concentrated. After washing the obtained residue with petroleum ether, 40.5 g of a beige solid are isolated (yield=94%). TLC silica gel 60 F 254 Merck, petroleum ether-AcOEt: 50-50 Rf=0.4. The obtained solid is placed in 100 mL of dichloromethane in the presence of 65 mL (877 mmol) of trifluoroacetic acid at room temperature for 1 h. After concentration, the obtained residue is taken up with water and then brought to pH 7 by adding NaHCO$_3$. The medium is extracted with AcOEt and then with dichloromethane. After drying on MgSO$_4$, the organic phases are dry concentrated. The obtained residue is taken up with EtOH, salified by adding a 2.3N HCl solution in isopropanol. The medium is saturated by adding ether, the formed crystals are filtered. 29.45 g of intermediate 4a are thereby isolated as a white powder (yield 88%).

TLC silica gel 60 F 254 Merck, CH$_2$Cl$_2$/MeOH 85/15, Rf=0.43.

b) INTERMEDIATES 6b-6d

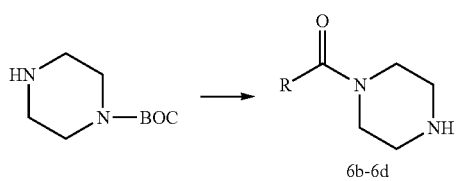

6b-6d

The synthesis of the intermediates 6b-6d is achieved from BOC-piperazine according to the operating procedure described for the synthesis of 6a by using various acid chlorides RCOCl, but without carrying out the final step for salifying the amine.

TABLE 6 intermediates 6b-6d

| RCOCl | Yield | TLC | State | Intermediates 6b-6d |
|---|---|---|---|---|
| | 91% | $CH_2Cl_2$—AcOEt: 95-5<br>Rf = 0.02 | oil | 6b: (2,5-Bis-trifluoromethyl-phenyl)-piperazin-1-yl-methanone |
| | 77% | $CH_2Cl_2$—AcOEt: 95-5<br>Rf = 0.02 | oil | 6c: (5-fluoro-2-trifluoromethyl-phenyl)-piperazin-1-yl-methanone |
| | 41% | $CH_2Cl_2$—MeOH: 95-5<br>Rf = 0.07 | oil | 6d: (4-fluoro-2-trifluoromethyl-phenyl)-piperazin-1-yl-methanone |

TLC: silica gel 60 F. 254 Merck.

INTERMEDIATES 7 a) 1-(2-trifluoromethyl-benzyl)-piperazine (7a)

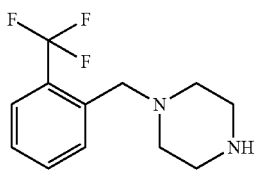

1.08 g (12.5 mmol) of piperazine are placed in the presence of 1 g (4.2 mmol) of 1-bromomethyl-2-trifluoromethyl-benzene and 0.64 mL (4.6 mmol) of triethylamine in 10 mL of toluene. The reaction medium is stirred for 30 min at room temperature and then heated to 110° C. for 6 h. After dry concentration, the obtained residue is taken up with AcOEt and washed with water. After drying on $MgSO_4$, the organic phases are dry concentrated, the obtained residue is purified by flash chromatography on silica ($CH_2Cl_2$-MeOH—$NH_4OH$: 90-9-1). 0.7 g of intermediate 7a are thereby isolated as a clear oil (yield 68%).

TLC silica gel 60 F 254 Merck, $CH_2Cl_2$-MeOH—$NH_4OH$: 90-9-1, Rf=0.27.

b) 1-(4-fluoro-2-trifluoromethyl-benzyl)-piperazine (7b)

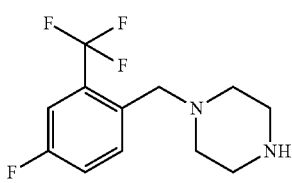

The synthesis of intermediate 7b is achieved from 1-bromomethyl-4-fluoro-2-trifluoromethyl-benzene according to the operating procedure described for synthesis of 4a (clear oil, yield 70%).

TLC silica gel 60 F 254 Merck, $CH_2Cl_2$-MeOH: 95-5, Rf=0.15.

INTERMEDIATES 8 a) 4-(2-chloro-phenoxy)-piperidine (8a)

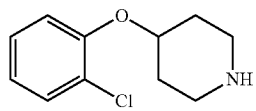 [SMILES: Clc1ccccc1OC1CCNCC1]

10 g (49.68 mmol) of BOC-4-hydroxy-piperidine are placed in the presence of 5.5 mL (54.65 mmol) of 2-chlorophenol, 15.6 g (59.62 mmol) of triphenylphosphine in 160 mL of THF. At 0° C., 20 mL (59.62 mmol) of DEAD (55% solution in toluene) are added dropwise. The reaction medium is heated for 8 h at 65° C., and then stirred for 16 h at room temperature. After concentration, the obtained residue is taken up with ether, washed with a soda (1N) solution and then with a NaCl saturated solution. After drying on MgSO$_4$, the organic phases are dry concentrated, and then taken up with a petroleum ether-Et$_2$O mixture: 65-35 in order to remove triphenylphosphine oxide. After filtration, the filtrate is concentrated, the obtained residue is purified by flash chromatography on silica (petroleum ether-Et$_2$O, gradient 100-0 to 65-35 over 30 min). 9.1 g of clear oil are obtained (yield 59%). TLC silica gel 60 F 254 Merck, CH$_2$Cl$_2$-AcOEt: 90-10, Rf=0.75. This oil is placed in 80 mL of dichloromethane in the presence of 8.67 mL (116.7 mmol) of TFA, and this solution is then stirred for 24 h at room temperature. The medium is concentrated, the obtained residue is taken up with AcOEt, washed with a soda (1N) solution and then with NaCl saturated water. After drying on MgSO$_4$, the organic phases are dry concentrated. 6.5 g of intermediate 8a are thus isolated as a clear oil (quantitative yield). TLC silica gel 60 F 254 Merck, CH$_2$Cl$_2$-MeOH—NH$_4$OH: 90-9-1, Rf=0.24.

b) 4-(2-chloro-5-fluoro-phenoxy)-piperidine (8b)

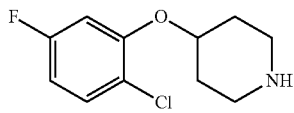

9 g (44.7 mmol) of BOC-4-hydroxy-piperidine are placed in 30 mL of dichloromethane at 0° C. 3.5 mL (44.7 mmol) of mesyl chloride and 8 mL (58.1 mmol) of triethylamine are slowly added. The reaction medium is stirred for 3 h at 0° C., and then filtered on a frit. The filtrate is washed with water. After drying on MgSO$_4$, the organic phase is concentrated. 12.48 g of oil are obtained (quantitative yield). TLC silica gel 60 F 254 Merck, CH$_2$Cl$_2$-MeOH: 95-5, Rf=0.60. 1.34 g (4.78 mmol) of this oil is placed in the presence of 0.50 mL (2.48 mmol) of 2-chloro-5-fluorophenol and of 3 g (4.78 mmol) of cesium carbonate in 5 mL of DMF. This solution is stirred for 24 h at 70° C. After concentration of the reaction medium, the obtained residue is purified by flash chromatography (petroleum ether-AcOEt, gradient 100-0 to 85-15 over 60 min). 0.84 g of clear oil is obtained (yield: 53%). TLC silica gel 60 F 254 Merck, CH$_2$Cl$_2$-AcOEt: 95-5, Rf=0.72. This oil is placed in 5 mL of CH$_2$Cl$_2$ in the presence of 0.76 mL (10.2 mmol) of TFA. The solution is stirred for 6 h at room temperature. After concentration of the reaction medium, the residue is taken up with AcOEt, washed with a soda (1N) solution and then with NaCl saturated water. After drying the organic phase on MgSO$_4$, 0.4 g of intermediate 8b is obtained as a clear oil (yield 69%).

TLC silica gel 60 F 254 Merck, CH$_2$Cl$_2$-MeOH: 95-5, Rf=0.19.

c) INTERMEDIATES 8c and 8d

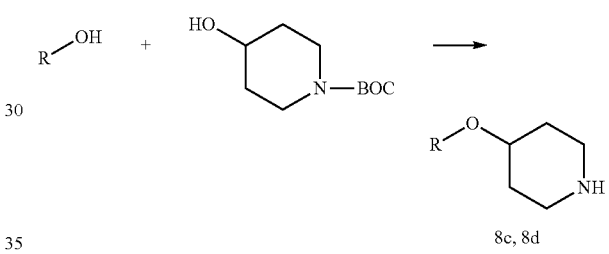

The synthesis of the intermediates 8c and 8d is achieved according to the operating procedure described for synthesis of 8a by using various phenols R—OH.

TABLE 7

| | | | | |
|---|---|---|---|---|
| | | intermediates 8c-8d | | |
| ROH | Yield | TLC | State | intermediates 8c-8d |
| ![F3C-phenol] | 65% | CH$_2$Cl$_2$—MeOH—NH$_4$OH: 90-9-1 Rf = 0.24 | solid | 8c: 4-(2-trifluoromethyl-phenoxy)-piperidine |
| ![4-F-phenol] | 71% | CH$_2$Cl$_2$—MeOH—NH$_4$OH: 90-9-1 Rf = 0.22 | solid | 8d: 4-(4-fluoro-phenoxy)-piperidine |

TLC: silica gel 60 F. 254 Merck.

d) INTERMEDIATES 8e-8i

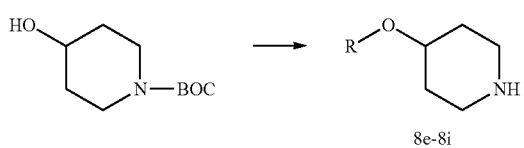

8e-8i

The synthesis of the intermediates 8e-8l is achieved according to the operating procedure described for the synthesis of 8b by using various phenols R—OH.

is purified by flash chromatography on silica (CH$_2$Cl$_2$-MeOH, gradient 100-0 to 95-5 over 45 min). 0.96 g of a clear oil is obtained (quantitative yield). TLC silica gel 60 F 254 Merck, CH$_2$Cl$_2$-MeOH: 95-5, Rf=0.75. This oil is placed in the presence of few drops of 15-crown-5 crown ether in 10 mL of THF at 0° C. and 0.15 g (3.98 mmol) of NaH (60% in paraffin) are added. The reaction medium is stirred for 30 min at 0° C. and then 0.55 mL (3.06 mmol) of benzyl-piperidin-4-one are added at 0° C. The mixture is then stirred at room temperature for 24 h, and then poured into water at 0° C. and extracted with AcOEt. The organic phase is washed with a

TABLE 8 intermediates 8e-8i

| ROH | Yield | TLC | State | Intermediates 8e-8i |
|---|---|---|---|---|
| F / OH (2-fluorophenol) | 48% | CH$_2$Cl$_2$—AcOEt: 90-10 Rf = 0.14 | oil | 8e: 4-(2-fluoro-phenoxy)-piperidine |
| Cl / OH / CF$_3$ (2-chloro-5-trifluoromethylphenol) | 38% | CH$_2$Cl$_2$—AcOEt: 90-10 Rf = 0.18 | oil | 8f: 4-(2-chloro-5-trifluoromethyl-phenoxy)-piperidine |
| CH$_3$ / OH (o-cresol) | 30% | CH$_2$Cl$_2$—MeOH: 95-5 Rf = 0.17 | oil | 8g: 4-o-Tolyloxy-piperidine |
| CF$_3$ / OH (4-trifluoromethylphenol) | 43% | CH$_2$Cl$_2$—MeOH: 95-5 Rf = 0.34 | oil | 8h: 4-(4-trifluoromethyl-phenoxy)-piperidine |
| OMe / OH (guaiacol) | 32% | CH$_2$Cl$_2$—MeOH: 95-5 Rf = 0.11 | oil | 8i: 4-(2-methoxy-phenoxy)-piperidine |

TLC: silica gel 60 F. 254 Merck.

INTERMEDIATES 9 a) 4-(2-fluoro-5-trifluoromethyl-benzyl)-piperidine (9a)

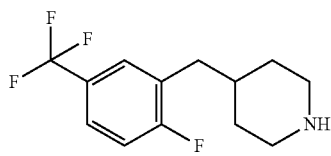 [SMILES: Fc1ccc(C(F)(F)F)cc1CC1CCNCC1]

0.8 g (3.1 mmol) of 2-bromomethyl-1-fluoro-4-trifluoromethylbenzene is placed in the presence of 0.9 mL (5.36 mmol) of triethylphosphite at 150° C. for 24 h. The reaction medium saturated NaHCO$_3$ solution, and then with a saturated NaCl solution. After drying on MgSO$_4$, the organic phases are dry concentrated. The obtained residue is purified by flash chromatography on silica (petroleum ether-AcOEt, gradient 100-0 to 90-10 over 45 min). 0.64 g of a clear oil is obtained (yield 60%). TLC silica gel 60 F 254 Merck petroleum ether-AcOEt: 90-10, Rf: 0,32. This oil is placed in 5 mL of MeOH in the presence of 0.12 g of palladium on charcoal under 5 bars of hydrogen, and this solution is then stirred 3 days at room temperature. After filtration on celite, the reaction medium is concentrated. The obtained residue is purified by flash chromatography on silica (CH$_2$Cl$_2$-MeOH, gradient 100-0 to 90-10 over 30 min, and then CH$_2$Cl$_2$-MeOH—

NH$_4$OH, gradient 100-0 to 90-9-1). 0.30 g of intermediate 9a is obtained as a clear oil (yield 63%). TLC silica gel 60 F 254 Merck CH$_2$Cl$_2$-AcOEt: 90-10, Rf=0,14.

b) 4-(4-fluoro-2-trifluoromethyl-benzyl)-piperidine (9b)

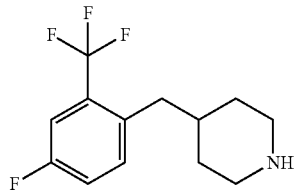 [SMILES: Fc1ccc(CC2CCNCC2)c(C(F)(F)F)c1]

The synthesis of the intermediate 9b is achieved from 1-bromomethyl-4-fluoro-2-trifluoromethylbenzene according to the operating procedure described for the synthesis of 9a (solid, yield 11%).

TLC silica gel 60 F 254 Merck, CH$_2$Cl$_2$-MeOH—NH$_4$OH: 90-9-1, Rf=0.26.

INTERMEDIATE 10

(4-fluoro-phenyl)-piperidin-4-yl-methanone (10)

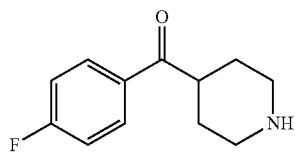 [SMILES: O=C(c1ccc(F)cc1)C1CCNCC1]

6.4 g (49.5 mmol) of isonipecotic acid are placed in the presence of 40 ml of acetic anhydride. The reaction medium is heated to 130° C. for 5 h and then dry concentrated. After triturating with petroleum ether, the formed crystals are filtered. 7.79 g of solid are obtained (92%). 0.5 g (2.92 mmol) of the obtained solid are placed in 1 mL of 1,2-dichloroethane in the presence of 0.92 mL (12.56 mmol) of thionyl chloride, and this solution is then stirred for 1 h at room temperature. The medium is dry concentrated and then the residue is taken up with 2 mL of 1,2-dichloroethane. This solution is added to a mixture of 0.90 g (6.72 mmol) of AlCl$_3$ and 1.29 mL (13.73 mmol) of fluorobenzene in 1 mL of 1,2-dichloroethane. The reaction medium is heated to 80° C. for 3 h. After the solution has returned to room temperature, it is poured on ice water, then the medium is extracted with dichloromethane. After drying on MgSO$_4$, the organic phases are dry concentrated, the obtained residue is purified by flash chromatography on silica (CH$_2$Cl$_2$-MeOH: 95-5). 0.44 g of an oil are isolated (60%). TLC silica gel 60 F 254 Merck, CH$_2$Cl$_2$-MeOH: 95-5, Rf=0.38. The obtained oil is placed in 6 mL of 6N hydrochloric acid and the mixture is heated to 100° C. for 18 h. The medium is neutralized by adding a concentrated soda solution and extracted with ethyl acetate. After drying on MgSO$_4$, the organic phases are dry concentrated. 0.23 g of intermediate 10 are obtained as an oil (62%).

TLC silica gel 60 F 254 Merck, CH$_2$Cl$_2$-MeOH: 95-5, Rf=0.13.

INTERMEDIATES 11 a) 3-(2-trifluoromethyl-phenoxy)-pyrrolidine (11a)

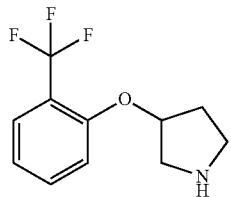 [SMILES: FC(F)(F)c1ccccc1OC1CCNC1]

0.67 mL (4 mmol) of 1-benzyl-pyrrolidin-3-ol are placed in the presence of 0.71 g (4.4 mmol) of 2-trifluoromethyl-phenol and of 1.26 g (4.8 mmol) of triphenylphosphine in 10 mL of THF. At 0° C., 2 mL (4.8 mmol) of DEAD (a 40% solution in toluene), are added dropwise. The reaction medium is heated for 6 h at 65° C., and then stirred for 16 h at room temperature. After concentration, the obtained residue is taken up with ether, washed with a soda (1N) solution and then with a NaCl solution. After drying on MgSO$_4$, the organic phases are dry concentrated, and then the residue is taken up with a petroleum ether-Et$_2$O 65-35 mixture for removing triphenylphosphine oxide. After filtration, the filtrate is concentrated, the obtained residue is purified by flash chromatography on silica (petroleum ether-Et$_2$O, gradient 100-0 to 60-40 over 45 min). 1.06 g of clear oil are obtained (yield 82%). TLC silica gel 60 F 254 Merck, petroleum ether-Et$_2$O 65-35, Rf=0.18. This oil is placed in 10 mL of a ethanol/THF 50/50 mixture in the presence of palladium on charcoal and under a pressure of 5 bars of hydrogen at room temperature for 18 h. The reaction medium is filtered on celite, the filtrate is dry concentrated. The obtained residue is purified by flash chromatography on silica (CH$_2$Cl$_2$-MeOH—NH$_4$OH, 90-9-1). 0.51 g of intermediate 11a are obtained as a clear oil (yield 83%).

TLC silica gel 60 F 254 Merck, CH$_2$Cl$_2$/MeOH 90/10, Rf=0.13.

b) 3-phenoxy-pyrrolidine (11b)

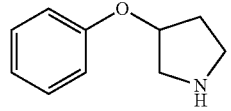 [SMILES: c1ccc(OC2CCNC2)cc1]

The synthesis of intermediate 11b is achieved from phenol according to the operating procedure described for the synthesis of 11a (solid, yield 24%).

TLC silica gel 60 F 254 Merck, CH$_2$Cl$_2$-MeOH: 90-10, Rf=0.21.

INTERMEDIATES 12 a) 2,4-dimethyl-6-piperazin-1-yl-2H-[1,2,4]triazine-3,5-dione (12a)

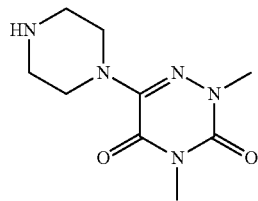 [SMILES: Cn1nc(N2CCNCC2)c(=O)n(C)c1=O]

4.75 g (55.15 mmol) of piperazine are placed in the presence of 4.05 g (18.4 mmol) of intermediate 1b in toluene at room temperature for 30 min. 2.8 mL (20.1 mmol) of triethylamine are added and the mixture is heated for 18 h at 110° C. After concentration of the reaction medium, the obtained residue is taken up with dichloromethane and washed with water. After drying on MgSO₄, the organic phase is dry concentrated. The obtained residue is purified by flash chromatography (CH₂Cl₂-MeOH: 60-40). 3.3 g of intermediate 12a is obtained as a white powder (yield: 79%).

TLC silica gel 60 F 254 Merck, CH₂Cl₂-MeOH: 50-50, Rf=0.4.

b) 2,4-dimethyl-6-(3-oxo-piperazin-1-yl)-2H-[1,2,4]triazine-3,5-dione (12b)

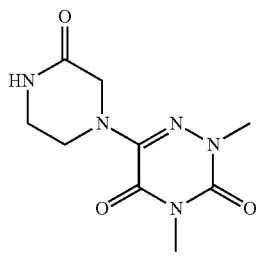 [SMILES: Cn1nc(N2CCNC(=O)C2)c(=O)n(C)c1=O]

The synthesis of the intermediate 12b is achieved from piperazin-2-one according to the operating procedure described in the synthesis of 12a, in n-butanol at 120° C. for 24 h (solid, yield 55%).

TLC silica gel 60 F 254 Merck, CH₂Cl₂-MeOH: 90-10, Rf=0.44.

c) 2,4-dimethyl-6-(3-methyl-piperazin-1-yl)-2H-[1,2,4]triazine-3,5-dione (12c)

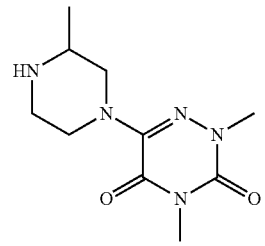 [SMILES: CC1CN(c2nn(C)c(=O)n(C)c2=O)CCN1]

The synthesis of the intermediate 12c is achieved from 2-methyl-piperazine according to the operating procedure described for the synthesis of 12a (solid, yield: 58%).

TLC silica gel 60 F 254 Merck, CH₂Cl₂-MeOH: 90-10, Rf=0.19.

d) INTERMEDIATES 12d-12f

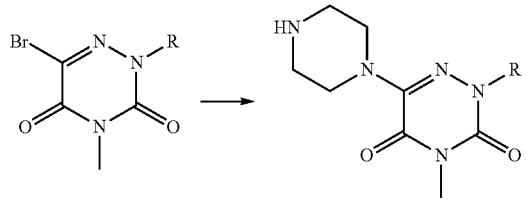

| R = (CH₂)₃CF₃ | 4a | 12d |
| R = (CH₂)₃CH₃ | 4c | 12e |
| R = (CH₂)₂CH(CH₃)₂ | 4g | 12f |

The synthesis of the intermediates 12d-12f is achieved from the intermediates 4a, 4c and 4 g respectively according to the operating procedure described for the synthesis of 12a.

TABLE 9

| | | intermediates 12d-12f | | |
|---|---|---|---|---|
| Starting synthons | Yield | TLC | State | Intermediates 12d-12f |
| 4a | 64% | CH₂Cl₂—MeOH: 90-10 Rf = 0.28 | solid | 12d: 4-methyl-6-piperazin-1-yl-2-(4,4,4-trifluoro-butyl)-2H-[1,2,4]triazine-3,5-dione |
| 4c | 88% | CH₂Cl₂—MeOH: 90-10 Rf = 0.18 | solid | 12e: 2-butyl-4-methyl-6-piperazin-1-yl-2H[1,2,4]triazine-3,5-dione |
| 4g | 53% | CH₂Cl₂—MeOH: 90-10 Rf = 0.27 | oil | 12f: 4-methyl-2-(3-methyl-butyl)-6-piperazin-1-yl-2H[1,2,4]triazine-3,5-dione |

TLC: silica gel 60 F 254 Merck

INTERMEDIATES 13 a) 5-(4-benzyl-piperazin-1-yl)-1,3-dimethyl-1H-pyrimidine-2,4-dione (13a)

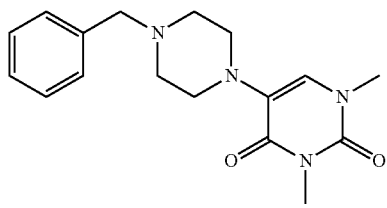 [SMILES: Cn1cc(N2CCN(Cc3ccccc3)CC2)c(=O)n(C)c1=O]

9.6 g (33.53 mmol) of 5-(4-benzyl-piperazin-1-yl)-1H-pyrimidine-2,4-dione are placed at 0° C. in 10 mL of dimethylformamide. 2.95 g (73.56 mmol) of sodium hydride (at 60% in paraffin) are added portion wise. The mixture is stirred for 40 min at 0° C. 5 mL (80.5 mmol) of methyl iodide are added, the medium is stirred at room temperature for 7 h. After concentration of the reaction medium, the obtained residue is taken up with AcOEt and washed with water. After drying on $MgSO_4$, the organic phase is concentrated. The obtained residue is triturated with ether, and then a precipitate is isolated by filtration. 4 g of intermediate 13a are obtained as a beige powder (yield: 38%).

TLC silica gel 60 F 254 Merck, $CH_2Cl_2$-MeOH—$NH_4OH$: 90-9-1, Rf=0.64.

b) 1,3-dimethyl-5-piperazin-1-yl-1H-pyrimidine-2,4-dione (13b)

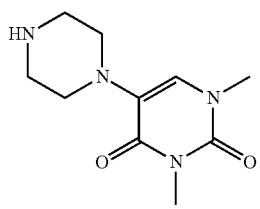 [SMILES: Cn1cc(N2CCNCC2)c(=O)n(C)c1=O]

2.6 g (8.26 mmol) of compound 13a are placed in the presence of 1.3 g of palladium and of 130 mL of formic acid in 300 mL of acetic acid at room temperature for 4 h. The mixture is heated to 100° C.° for 2 h 30 min. After neutralization with a 10% soda solution, the reaction medium is extracted with $CHCl_3$. The organic phase is washed with water and then with a saturated NaCl solution. After drying on $MgSO_4$, the organic phase is concentrated. The obtained residue is purified by flash chromatography ($CH_2Cl_2$-MeOH—$NH_4OH$, gradient 90-10-0 to 90-9-1 over 30 min). 1.05 g of intermediate 13b is obtained as a beige solid (yield: 56%).

TLC silica gel 60 F 254 Merck, $CH_2Cl_2$-MeOH—$NH_4OH$: 90-9-1, Rf=0.07.

EXAMPLES

Example 1

4-heptyl-2-methyl-6-[4-(2-trifluoromethyl-benzoyl)-piperazin-1-yl]-2H-[1,2,4]triazine-3,5-dione (1)

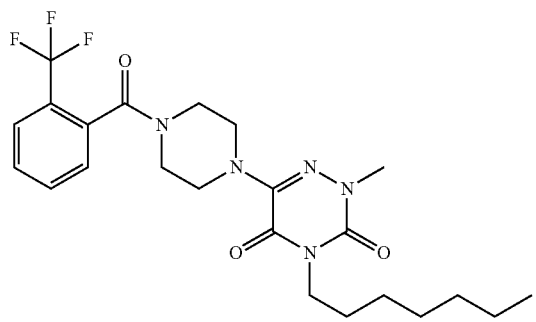 [SMILES: CCCCCCCn1c(=O)c(N2CCN(C(=O)c3ccccc3C(F)(F)F)CC2)nn(C)c1=O]

The compound 1 is prepared according to the synthesis method 1: 0.33 g (1.12 mmol) of derivative 6a and 0.41 g (1.35 mmol) of the triazine 5b are placed in 10 mL of butanol-1 in the presence of 0.55 mL (3.93 mmol) of $NEt_3$. This mixture is stirred at 120° C. for 24 h. After dry concentration of the reaction medium, the obtained residue is taken up with AcOEt and washed with water and with an NaCl saturated solution. After drying on $MgSO_4$, the organic phase is concentrated. The obtained residue is purified by flash chromatography on silica (petroleum ether-AcOEt: 60-40). 0.53 g of a clear oil are isolated (yield: 98%).

TLC silica gel 60 F 254 Merck, petroleum ether-AcOEt: 50-50, Rf=0.43.

$^1$H NMR ($CDCl_3$) ppm: 0.87 (t, 3H, J=6.57 Hz) 1.21-1.38 (m, 8H), 1.57-1.66 (m, 2H), 3.23-3.34 (m, 4H), 3.40-3.47 (m, 1H), 3.46-3.57 (m, 4H), 3.82-3.95 (m, 3H), 3.98-4.05 (m, 1H), 7.35 (d, 1H, J=7.83 Hz), 7.54 (t, 1H, J=8.08 Hz) 7.62 (t, 1H, J=7.07 Hz), 7.72 (d, 1H, J=7.33 Hz).

MS (+ESI) m/z 482 (MH+)

Example 2

2-methyl-6-[4-(2-trifluoromethyl-benzoyl)-piperazin-1-yl]-2H-[1,2,4]triazine-3,5-dione (2)

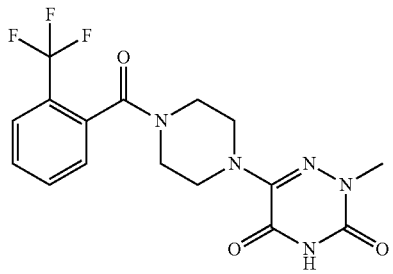 [SMILES: Cn1nc(N2CCN(C(=O)c3ccccc3C(F)(F)F)CC2)c(=O)[nH]c1=O]

The compound 2 (yellow powder) is prepared from the triazine 2e and from the intermediate 6a according to the synthesis method 1 in toluene (yield: 25%).

TLC silica gel 60 F 254 Merck, petroleum ether-AcOEt: 80-20, Rf=0.2.
MP=146° C.
$^1$H NMR (CDCl$_3$) ppm: 3.24-3.42 (m, 4H), 3.42-3.52 (m, 4H), 3.52-3.61 (m, 1H), 3.80-3.89 (m, 1H), 4.06-3.97 (m, 1H), 7.35 (d, 1H, J=7.32 Hz), 7.54 (t, 1H, J=7.57 Hz) 7.61 (t, 1H, J=7.57 Hz), 7.72 (d, 1H, J=7.83 Hz), 8.58 (s, 1H).
MS (+ESI) m/z 384 (MH+)

Example 3

4-methyl-2-(4,4,4-trifluoro-butyl)-6-[4-(2-trifluoromethyl-benzoyl)-piperazin-1-yl]-2H-[1,2,4]triazine-3,5-dione (3)

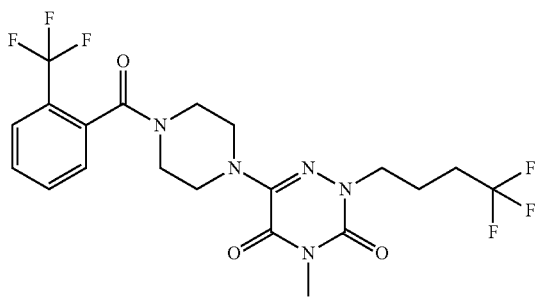 [SMILES: Cn1c(=O)c(N2CCN(C(=O)c3ccccc3C(F)(F)F)CC2)nn(CCCC(F)(F)F)c1=O]

The compound 3 (oil) is prepared from the triazine 4a and from the intermediate 6a according to the synthesis method 1 in n-butanol (yield: 19%).
TLC silica gel 60 F 254 Merck, CH$_2$Cl$_2$-AcOEt: 95-5, Rf=0.28.
$^1$H NMR (CDCl$_3$) ppm: 1.95-2.05 (m, 2H), 2.08-2.22, (m, 2H), 3.26-3.32 (m, 4H), 3.35 (s, 3H), 3.41-3.50 (m, 1H), 3.50-3.58 (m, 1H), 3.82-3.90 (m, 1H), 3.95 (t, 2H, J=6.82 Hz), 3.98-4.08 (m, 1H), 7.35 (d, 1H, J=7.83 Hz), 7.55 (t, 1H, J=7.83 Hz), 7.62 (t, 1H, J=7.83 Hz), 7.73 (d, 1H, J=7.32 Hz).
MS (+APCI) m/z 494 (MH+)

Example 4

4-methyl-6-[4-(2-trifluoromethyl-benzoyl)-piperazin-1-yl]-2H-[1,2,4]triazine-3,5-dione (4)

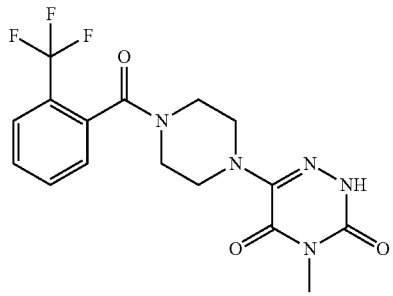 [SMILES: Cn1c(=O)[nH]nc(N2CCN(C(=O)c3ccccc3C(F)(F)F)CC2)c1=O]

The compound 4 (solid) is prepared from the triazine 2a and the intermediate 6a according to the synthesis method 1 in toluene (yield: 27%).
TLC silica gel 60 F 254 Merck, CH$_2$Cl$_2$-AcOEt: 70-30, Rf=0.26.
MP=235° C.

$^1$H NMR (CDCl$_3$) ppm: 2.28-3.34 (m, 4H), 3.34 (s, 3H), 3.39-3.48 (m, 1H), 3.48-3.57 (m, 1H), 3.80-3.91 (m, 1H), 3.96-4.07 (m, 1H), 7.35 (d, 1H, J=7.58 Hz), 7.54 (t, 1H, J=7.83 Hz) 7.62 (t, 1H, J=7.58 Hz), 7.72 (d, 1H, J=7.58 Hz), 8.77 (s, 1H).
MS (+ESI) m/z 384 (MH+)

Example 5

2,4-dimethyl-6-[4-(2-trifluoromethyl-benzoyl)-piperazin-1-yl]-2H-[1,2,4]triazine-3,5-dione (5)

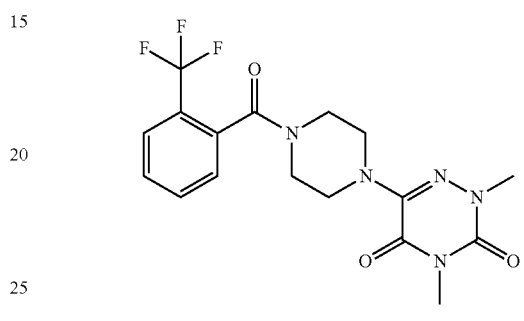

The compound 5 (solid) is prepared from the triazine 1b and the intermediate 6a according to the synthesis method 1 in toluene (yield: 55%).
TLC silica gel 60 F 254 Merck, AcOEt: 100, Rf=0.37.
MP=76° C.
$^1$H NMR (CDCl$_3$) ppm: 3.26-3.33 (m, 4H), 3.34 (s, 3H), 3.40-3.49 (m, 1H), 3.49-3.58 (m, 3H), 3.81-3.90 (m, 1H), 3.97-4.06 (m, 1H), 7.35 (d, 1H, J=7.07 Hz), 7.54 (t, 1H, J=7.83 Hz) 7.61 (t, 1H, J=7.83 Hz), 7.73 (d, 1H, J=8.08 Hz).
MS (+ESI) m/z 398 (MH+)

Example 6

5-[4-(2-trifluoromethyl-benzoyl)-piperazin-1-yl]-1H-pyrimidine-2,4-dione (6)

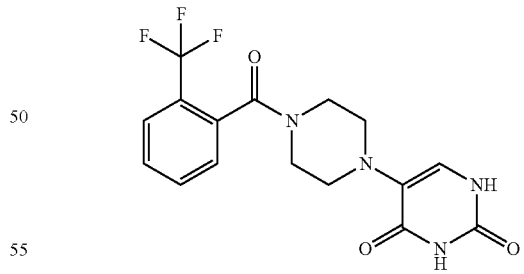

The compound 6 (solid) is prepared from 5-bromo-1H-pyrimidine-2,4-dione and from the intermediate 6a according to the synthesis method 1 in dimethylformamide (yield: 47%).
TLC silica gel 60 F 254 Merck, CH$_2$Cl$_2$-MeOH: 90-10, Rf=0.3.
MP=285° C.
$^1$H NMR (DMSO) ppm: 2.59-2.69 (m, 1H), 2.72-2.87 (m, 2H), 2.88-2.98 (m, 1H), 3.05-3.16 (m, 1H), 3.16-3.25 (m, 1H), 3.63-3.79 (m, 2H), 6.79 (s, 1H), 7.49 (d, 1H, J=7.07 Hz), 7.66 (t, 1H, J=7.83 Hz) 7.76 (t, 1H, J=7.58 Hz), 7.82 (d, 1H, J=7.58 Hz), 10.53 (s, 1H), 11.10 (s, 1H).

MS (+APCI) m/z 369 (MH+)

Example 7

2,4-dimethyl-6-[4-(3-trifluoromethyl-phenyl)-piperazin-1-yl]-2H-[1,2,4]triazine-3,5-dione (7)

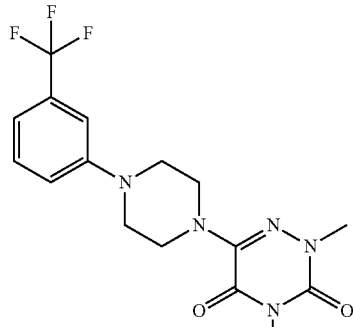

The compound 7 (solid) is prepared from the triazine 1b and from 1-(3-trifluoromethyl-phenyl)-piperazine according to the synthesis method 1 in n-butanol (yield: 63%).

TLC silica gel 60 F 254 Merck, $CH_2Cl_2$-MeOH: 95-5, Rf=0.78.

MP=163° C.

MS (+ESI) m/z 370 (MH+)

Example 8

4-methyl-2-(4,4,4-trifluoro-butyl)-6-[4-(3-trifluoromethyl-phenyl)-piperazin-1-yl]-2H-[1,2,4]triazine-3,5-dione (8)

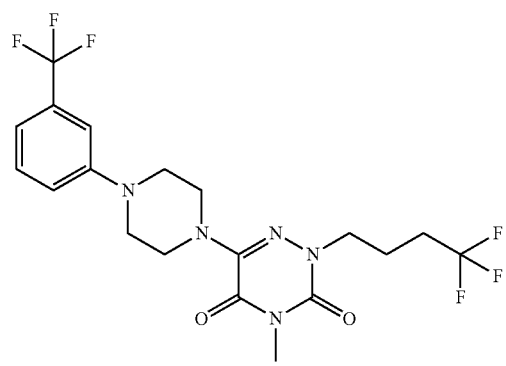 [SMILES: Cn1c(=O)c(N2CCN(c3cccc(C(F)(F)F)c3)CC2)nn(CCCC(F)(F)F)c1=O]

The compound 8 (oil) is prepared from the triazine 4a and from 1-(3-trifluoromethyl-phenyl)-piperazine according to the synthesis method 1 in n-butanol (yield: 76%).

TLC silica gel 60 F 254 Merck, $CH_2Cl_2$-AcOEt: 90-10, Rf=0.59.

MS (+ESI) m/z 466 (MH+)

Example 9

4-methyl-2-(4,4,4-trifluoro-butyl)-6-[4-(2-trifluoromethyl-phenyl)-piperazin-1-yl]-2H-[1,2,4]triazine-3,5-dione (9)

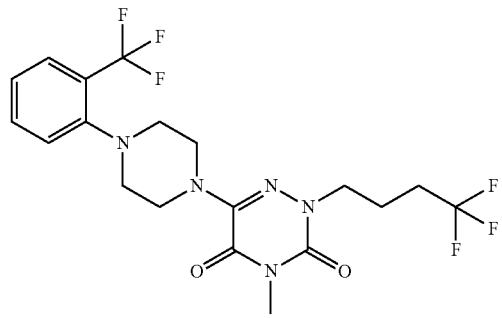 [SMILES: Cn1c(=O)c(N2CCN(c3ccccc3C(F)(F)F)CC2)nn(CCCC(F)(F)F)c1=O]

The compound 9 (solid) is prepared from the triazine 4a and from 1-(2-trifluoromethyl-phenyl)-piperazine according to the synthesis method 1 in n-butanol (yield: 82%).

TLC silica gel 60 F 254 Merck, $CH_2Cl_2$-AcOEt: 90-10, Rf=0.54.

MS (+ESI) m/z 466 (MH+)

Example 10

6-(4-benzyl-piperidin-1-yl)-2,4-dimethyl-2H-[1,2,4]triazine-3,5-dione (10)

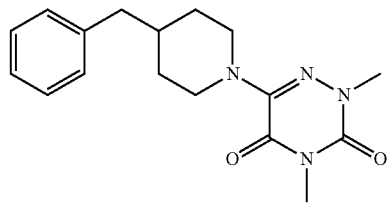

The compound 10 (oil) is prepared from the triazine 1b and from 4-benzyl-piperidine according to the synthesis method 1 in n-butanol (yield: 93%).

TLC silica gel 60 F 254 Merck, $CH_2Cl_2$-AcOEt: 95-5, Rf=0.28.

MS (+ESI) m/z 315 (MH+)

Example 11

2,4-dimethyl-6-[4-(2-trifluoromethyl-phenoxy)-piperidin-1-yl]-2H-[1,2,4]triazine-3,5-dione (11)

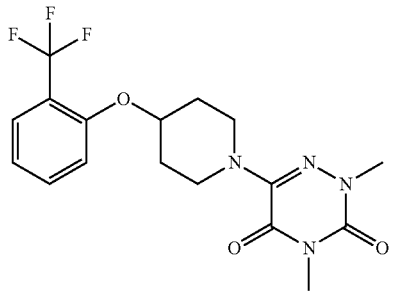

The compound 11 (oil) is prepared from the triazine 1b and from the intermediate 8c according to the synthesis method 1 in n-butanol (yield: 56%).

TLC silica gel 60 F 254 Merck, CH$_2$Cl$_2$-AcOEt: 95-5, Rf=0.27.

$^1$H NMR (CDCl$_3$) ppm: 1.95-2.11 (m, 4H), 3.36 (s, 3H), 3.49-3.57 (m, 7H), 4.70 (m, 1H), 6.99 (t, 1H, J=7.07 Hz) 7.00 (d, 1H, J=7.07 Hz), 7.47 (t, 1H, J=8.08 Hz), 7.58 (d, 1H, J=7.58 Hz).

MS (+ESI) m/z 385 (MH+)

Example 12

3-{4-heptyl-3,5-dioxo-6-[4-(2-trifluoromethyl-phenoxy)-piperidin-1-yl]-4,5-dihydro-3H-[1,2,4]triazin-2-yl}-propionitrile (12)

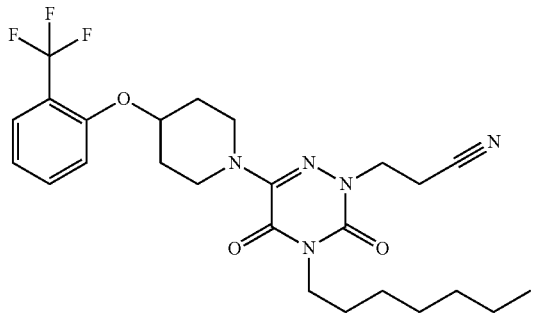 [SMILES: CCCCCCCn1c(=O)c(N2CCC(Oc3ccccc3C(F)(F)F)CC2)nn(CCC#N)c1=O]

The compound 12 (oil) is prepared from the triazine 3c and from the intermediate 8c according to the synthesis method 1 in n-butanol (yield: 46%).

$^1$H NMR (CDCl$_3$) ppm: 0.87 (t, 3H, J=6.31 Hz), 1.24-1.36 (m, 8H), 1.58-1.67 (m, 2H), 1.97-2.10 (m, 4H), 2.80 (t, 2H, J=7.83 Hz), 3.48-3.56 (m, 2H), 3.59-3.65 (m, 2H), 3.91 (t, 2H, J=7.07 Hz), 4.18 (t, 2H, J=6.57 Hz), 4.72 (m, 1H), 6.97-7.02 (m, 2H), 7.47 (t, 1H, J=7.83 Hz), 7.58 (d, 1H, J=7.07 Hz).

MS (+ESI) m/z 508 (MH+)

Example 13

2-butyl-4-methyl-6-[4-(2-trifluoromethyl-phenoxy)-piperidin-1-yl]-2H-[1,2,4]triazine-3,5-dione (13)

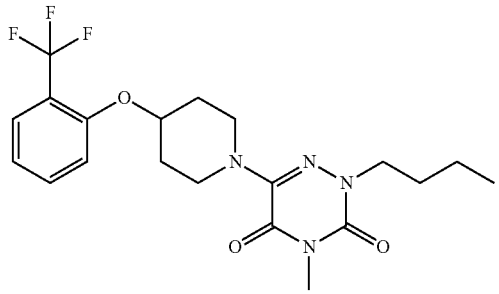 [SMILES: CCCCn1nc(N2CCC(Oc3ccccc3C(F)(F)F)CC2)c(=O)n(C)c1=O]

The compound 13 (oil) is prepared from the triazine 4c and from the intermediate 8c according to the synthesis method 1 in n-butanol (yield: 44%).

$^1$H NMR (CDCl$_3$) ppm: 0.95 (t, 3H, J=7.58 Hz), 1.31-1.41 (m, 2H), 1.66-1.75 (m, 2H), 1.96-2.10 (m, 4H), 3.35 (s, 3H), 3.47-3.55 (m, 4H), 3.89 (t, 2H, J=7.58 Hz), 4.70 (m, 1H), 6.99 (t, 1H, J=7.58 Hz), 7.00 (d, 1H, J=7.32 Hz), 7.47 (t, 1H, J=8.08 Hz), 7.58 (d, 1H, J=7.32 Hz).

MS (+ESI) m/z 427 (MH+)

Example 14

N-methyl-2-{4-methyl-3,5-dioxo-6-[4-(2-trifluoromethyl-phenoxy)-piperidin-1-yl]-4,5-dihydro-3H-[1,2,4]triazin-2-yl}-acetamide (14)

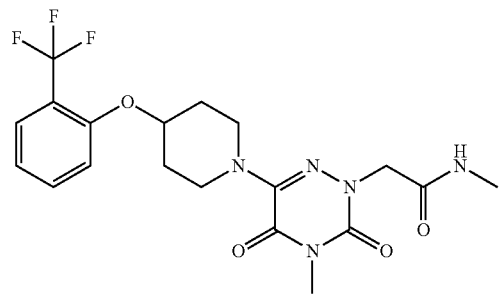 [SMILES: CNC(=O)Cn1nc(N2CCC(Oc3ccccc3C(F)(F)F)CC2)c(=O)n(C)c1=O]

The compound 14 (oil) is prepared from the triazine 4d and from the intermediate 8c according to the synthesis method 1 in n-butanol (yield: 52%).

$^1$H NMR (CDCl$_3$) ppm: 1.94-2.09 (m, 4H), 2.85 (d, 3H, J=5.05 Hz), 3.36 (s, 3H), 3.48-3.63 (m, 4H), 4.51 (s, 2H), 4.70 (m, 1H), 5.90 (m, 1H), 6.99 (d, 1H, J=7.32 Hz), 7.00 (t, 1H, J=6.82 Hz), 7.47 (t, 1H, J=7.83 Hz), 7.58 (d, 1H, J=7.83 Hz).

MS (+ESI) m/z 442 (MH+)

Example 15

2-(2-ethoxy-ethyl)-4-methyl-6-[4-(2-trifluoromethyl-phenoxy)-piperidin-1-yl]-2H-[1,2,4]triazine-3,5-dione (15)

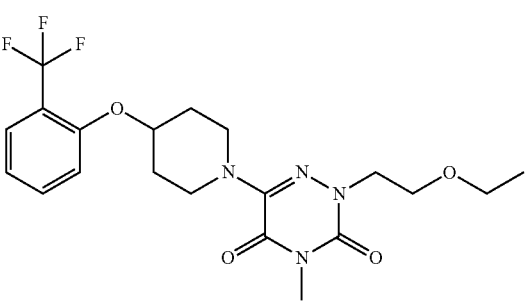 [SMILES: CCOCCn1nc(N2CCC(Oc3ccccc3C(F)(F)F)CC2)c(=O)n(C)c1=O]

The compound 15 (oil) is prepared from the triazine 4e and from the intermediate 8c according to the synthesis method 1 in n-butanol (yield: 47%).

$^1$H NMR (CDCl$_3$) ppm: 1.18 (t, 3H, J=7.07 Hz), 1.95-2.10 (m, 4H), 3.35 (s, 3H), 3.47-3.58 (m, 6H), 3.74 (t, 2H, J=5.81 Hz), 4.08 (t, 2H, J=5.81 Hz), 4.71 (m, 1H), 6.99 (t, 1H, J=7.07 Hz), 7.00 (d, 1H, J=7.83 Hz), 7.47 (t, 1H, J=7.58 Hz), 7.58 (d, 1H, J=7.07 Hz).

MS (+ESI) m/z 443 (MH+)

Example 16

2-[2-(1H-Indol-3-yl)-ethyl]-4-methyl-6-[4-(2-trifluoromethyl-phenoxy)-piperidin-1-yl]-2H-[1,2,4]triazine-3,5-dione (16)

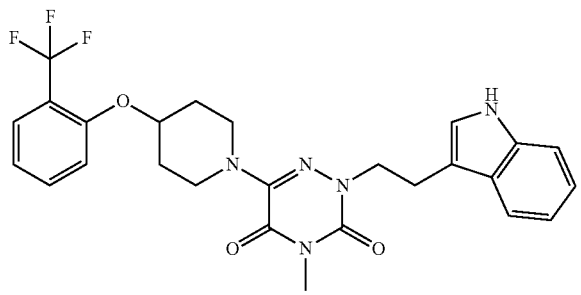 [SMILES: Cn1c(=O)c(N2CCC(Oc3ccccc3C(F)(F)F)CC2)nn(CCc2c[nH]c3ccccc23)c1=O]

The compound 16 (oil) is prepared from the triazine 4f and from the intermediate 8c according to the synthesis method 1 in n-butanol (yield: 20%).

$^1$H NMR (CDCl$_3$) ppm: 1.84-2.00 (m, 4H), 3.21 (t, 2H, J=7.32 Hz), 3.34 (s, 3H), 3.36-3.46 (m, 4H), 4.22 (t, 2H, J=7.32 Hz), 4.63 (m, 1H), 6.99 (d, 1H, J=8.34 Hz), 7.00 (t, 1H, J=8.34 Hz), 7.06 (s br, 1H), 7.10 (t, 3H, J=7.83 Hz), 7.17 (t, 1H, J=7.32 Hz), 7.34 (d, 1H, J=8.08 Hz), 7.48 (t, 1H, J=7.83 Hz), 7.57-7.65 (m, 2H), 7.99 (s br, 1H).

MS (+ESI) m/z 514 (MH+)

Example 17

4-methyl-2-(3-methyl-butyl)-6-[4-(2-trifluoromethyl-phenoxy)-piperidin-1-yl]-2H-[1,2,4]triazine-3,5-dione (17)

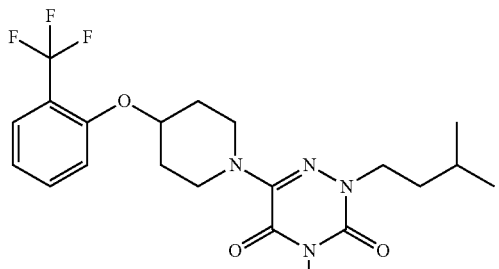

The compound 17 (oil) is prepared from the triazine 4 g and from the intermediate 8c according to the synthesis method 1 in n-butanol (yield: 42%).

MS (+ESI) m/z 441 (MH+)

Example 18

4-methyl-2-[2-(3-nitro-phenyl)-2-oxo-ethyl]-6-[4-(2-trifluoromethyl-phenoxy)-piperidin-1-yl]-2H-[1,2,4]triazine-3,5-dione (18)

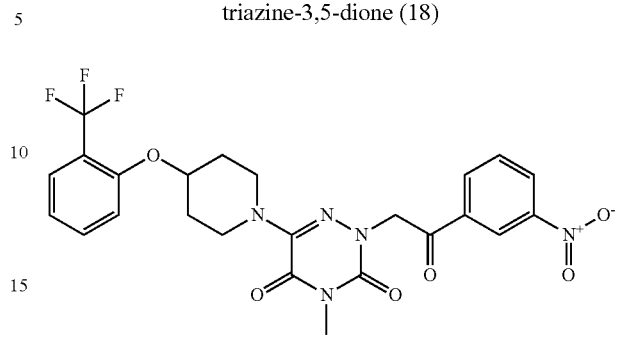

The compound 18 (oil) is prepared from the triazine 4 h and of the intermediate 8c according to the synthesis method 1 in n-butanol (yield: 32%).

MS (+ESI) m/z 534 (MH+)

Example 19

4-methyl-2-(4-oxo-4-thiophen-2-yl-butyl)-6-[4-(2-trifluoromethyl-phenoxy)-piperidin-1-yl]-2H-[1,2,4]triazine-3,5-dione (19)

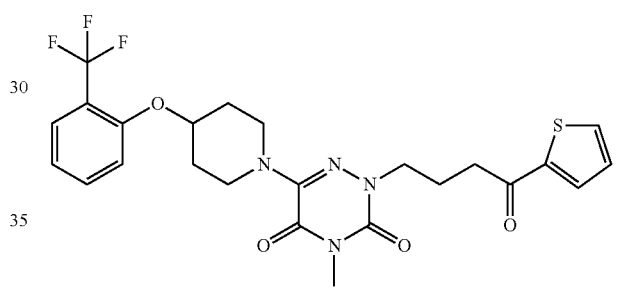

The compound 19 (oil) is prepared from the triazine 4Ii and from the intermediate 8c according to the synthesis method 1 in n-butanol (yield: 51%).

$^1$H NMR (CDCl$_3$) ppm: 1.91-2.07 (m, 4H), 2.21 (m, 2H, J=6.82 Hz), 3.00 (t, 2H, J=7.32 Hz), 3.31 (s, 3H), 3.42-3.54 (m, 4H), 4.01 (t, 2H, J=6.31 Hz), 4.67 (m, 1H), 6.98 (d, 1H, J=8.08 Hz), 6.99 (t, 1H, J=7.59 Hz), 7.11 (m, 1H), 7.47 (t, 1H, J=7.83 Hz), 7.58 (d, 1H, J=7.83 Hz), 7.61 (d, 1H, J=5.30 Hz), 7.69 (m, 1H).

MS (+ESI) m/z 523 (MH+)

Example 20

2-{4-methyl-3,5-dioxo-6-[4-(2-trifluoromethyl-phenoxy)-piperidin-1-yl]-4,5-dihydro-3H-[1,2,4]triazin-2-yl}-N-(3-nitro-phenyl)-acetamide (20)

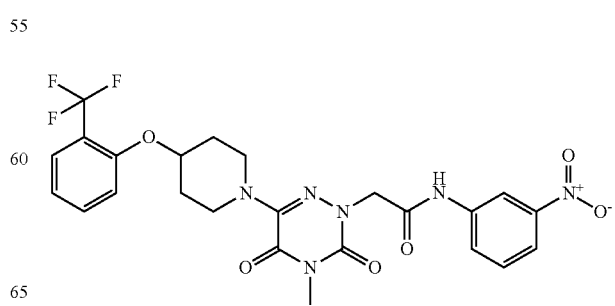

The compound 20 (oil) is prepared from the triazine 4j and from the intermediate 8c according to the synthesis method 1 in n-butanol (yield: 67%).

MS (+ESI) m/z 549 (MH+)

Example 21

4-benzyloxymethyl-6-[4-(2-chloro-phenoxy)-piperidin-1-yl]-2-methyl-2H-[1,2,4]triazine-3,5-dione (21)

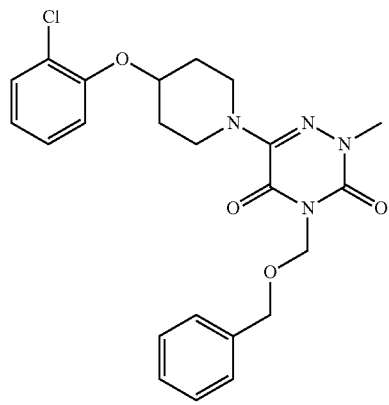 [SMILES: Cn1nc(N2CCC(Oc3ccccc3Cl)CC2)c(=O)n(COCc2ccccc2)c1=O]

The compound 21 (oil) is prepared from the triazine 5c and from the intermediate 8a according to the synthesis method 1 in n-butanol (yield: 60%).

MS (+ESI) m/z 457 (MH+)

Example 22

6-[4-(2-chloro-phenoxy)-piperidin-1-yl]-2-methyl-4-(4,4,4-trifluoro-butyl)-2H-[1,2,4]triazine-3,5-dione (22)

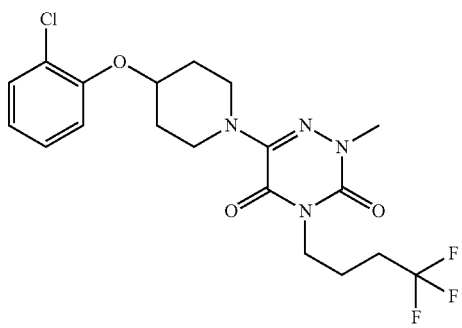 [SMILES: Cn1nc(N2CCC(Oc3ccccc3Cl)CC2)c(=O)n(CCCC(F)(F)F)c1=O]

The compound 22 (oil) is prepared from the triazine 5a and from the intermediate 8a according to the synthesis method 1 in n-butanol (yield: 39%).

TLC silica gel 60 F 254 Merck, $CH_2Cl_2$-AcOEt: 95-5, Rf=0.71.

MS (+APCI) m/z 447 (MH+)

Example 23

3-{6-[4-(2-chloro-phenoxy)-piperidin-1-yl]-4-methyl-3,5-dioxo-4,5-dihydro-3H-[1,2,4]triazin-2-yl}-propionitrile (23)

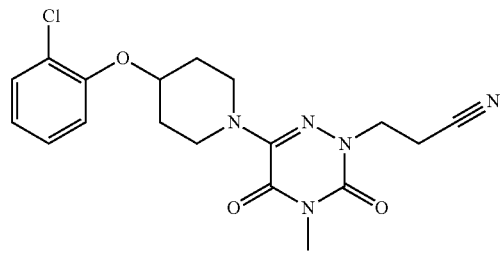 [SMILES: Cn1c(=O)c(N2CCC(Oc3ccccc3Cl)CC2)nn(CCC#N)c1=O]

The compound 23 (oil) is prepared from the triazine 3a and from the intermediate 8a according to the synthesis method 1 in n-butanol (yield: 58%).

TLC silica gel 60 F 254 Merck, petroleum ether-AcOEt: 80-20, Rf=0.36.

$^1$H NMR (CDCl$_3$) ppm: 1.94-2.11 (m, 4H), 2.81 (t, 2H, J=6.57 Hz), 3.36 (s, 3H), 3.49-3.58 (m, 2H), 3.64-3.73 (m, 2H), 4.19 (t, 2H, J=7.07 Hz), 4.56-4.63 (m, 1H), 6.92 (t, 1H, J=7.07 Hz), 6.97 (d, 1H, J=8.33 Hz), 7.20 (t, 1H, J=8.34 Hz), 7.38 (d, 1H, J=7.32 Hz), MS (+APCI) m/z 390 (MH+)

Example 24

3-[6-[4-(2-chloro-phenoxy)-piperidin-1-yl]-3,5-dioxo-4-(4,4,4-trifluoro-butyl)-4,5-dihydro-3H-[1,2,4]triazin-2-yl]-propionitrile (24)

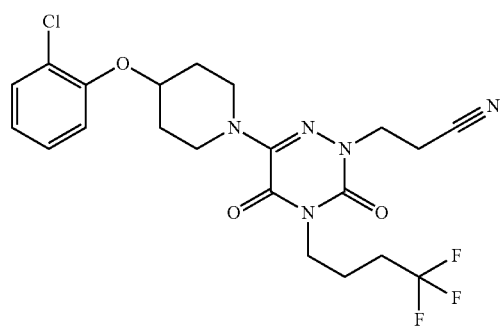 [SMILES: N#CCCn1nc(N2CCC(Oc3ccccc3Cl)CC2)c(=O)n(CCCC(F)(F)F)c1=O]

The compound 24 (oil) is prepared from the triazine 3b and from the intermediate 8a according to the synthesis method 1 in n-butanol (yield: 76%).

TLC silica gel 60 F 254 Merck, petroleum ether-AcOEt: 80-20, Rf=0.11.

MS (+APCI) m/z 486 (MH+)

Example 25

6-[4-(2-chloro-phenoxy)-piperidin-1-yl]-4-methyl-2-(4,4,4-trifluoro-butyl)-2H-[1,2,4]triazine-3,5-dione (25)

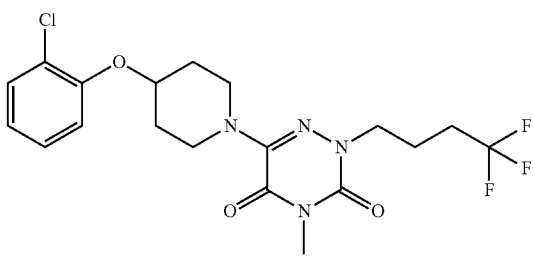 [SMILES: Cn1c(=O)c(N2CCC(Oc3ccccc3Cl)CC2)nn(CCCC(F)(F)F)c1=O]

The compound 25 (oil) is prepared from the triazine 4a and the intermediate 8a according to the synthesis method 1 in n-butanol (yield: 77%).

TLC silica gel 60 F 254 Merck, CH$_2$Cl$_2$-AcOEt: 95-5, Rf=0.69.

$^1$H NMR (CDCl$_3$) ppm: 1.95-2.10 (m, 6H), 2.10-2.24 (m, 2H), 3.36 (s, 3H), 3.43-3.51 (m, 2H), 3.60-3.69 (m, 2H), 3.96 (t, 2H, J=7.32 Hz), 4.56-4.62 (m, 1H), 6.92 (t, 1H, J=7.58 Hz), 6.97 (d, 1H, J=8.33 Hz), 7.20 (t, 1H, J=8.33 Hz), 7.38 (d, 1H, 7.83 Hz).

MS (+APCI) m/z 447 (MH+)

Example 26

2-butyl-6-[4-(2-chloro-phenoxy)-piperidin-1-yl]-4-methyl-2H-[1,2,4]triazine-3,5-dione (26)

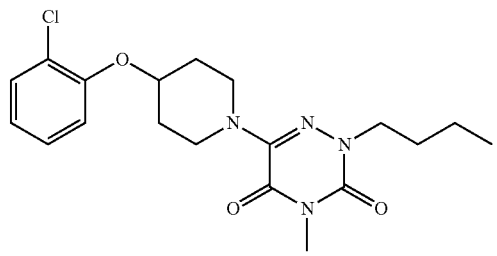 [SMILES: CCCCn1nc(N2CCC(Oc3ccccc3Cl)CC2)c(=O)n(C)c1=O]

The compound 26 (oil) is prepared from the triazine 4c and from the intermediate 8a according to the synthesis method 1 in n-butanol (yield: 44%).

TLC silica gel 60 F 254 Merck, CH$_2$Cl$_2$-AcOEt: 95-5, Rf=0.62.

MS (+APCI) m/z 393 (MH+)

Example 27

6-[4-(2-chloro-phenoxy)-piperidin-1-yl]-2,4-dimethyl-2H-[1,2,4]triazine-3,5-dione (27)

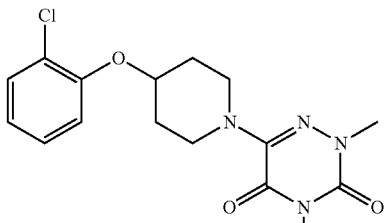

The compound 27 (solid) is prepared from the triazine 1b and from the intermediate 8a according to the synthesis method 1 in n-butanol (yield: 60%).

TLC silica gel 60 F 254 Merck, CH$_2$Cl$_2$-AcOEt: 95-5, Rf=0.51. F=109° C.

$^1$H NMR (CDCl$_3$) ppm: 1.96-2.08 (m, 4H), 3.35 (s, 3H), 3.35-3.46 (m, 2H), 3.54 (s, 3H), 3.61-3.64 (m, 2H), 4.58 (m, 1H), 6.92 (t, 1H, J=7.6 Hz), 6.97 (d, 1H, J=8.2 Hz), 7.2 (t, 1H, J=7.8 Hz), 7.37 (d, 1H, J=7.88 Hz).

MS (+ESI) m/z 351 (MH+)

Example 28

6-[4-(2-fluoro-phenoxy)-piperidin-1-yl]-2,4-dimethyl-2H-[1,2,4]triazine-3,5-dione (28)

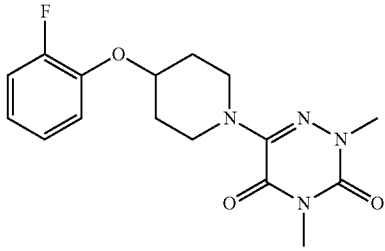 [SMILES: Cn1nc(N2CCC(Oc3ccccc3F)CC2)c(=O)n(C)c1=O]

The compound 28 (oil) is prepared from the triazine 1b and from the intermediate 8e according to the synthesis method 1 in n-butanol (yield: 63%).

TLC silica gel 60 F 254 Merck, CH$_2$Cl$_2$-AcOEt: 95-5, Rf=0.29.

$^1$H NMR (CDCl$_3$) ppm: 1.94-1.99 (m, 2H), 2.02-2.09 (m, 2H), 3.26-3.38 (m, 2H), 3.35 (s, 3H), 3.54 (s, 3H), 3.67-3.74 (m, 2H), 4.48 (m, 1H), 6.92-6.97 (m, 1H), 6.99-7.12 (m, 3H).

MS (+ESI) m/z 335 (MH+)

Example 29

6-[4-(2-chloro-5-trifluoromethyl-phenoxy)-piperidin-1-yl]-2,4-dimethyl-2H-[1,2,4]triazine-3,5-dione (29)

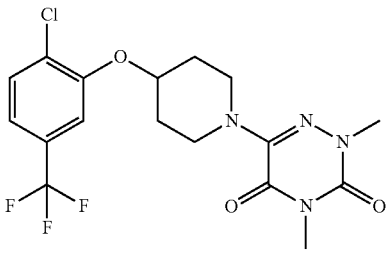 [SMILES: Cn1nc(N2CCC(Oc3cc(C(F)(F)F)ccc3Cl)CC2)c(=O)n(C)c1=O]

The compound 29 (solid) is prepared from the triazine 1b and from the intermediate 8f according to the synthesis method 1 in n-butanol (yield: 58%).
TLC silica gel 60 F 254 Merck, CH$_2$Cl$_2$-AcOEt: 95-5, Rf=0.44.
MP=160° C.
$^1$H NMR (CDCl$_3$) ppm: 1.98-2.03 (m, 2H), 2.05-2.12 (m, 2H), 3.36 (s, 3H), 3.43-3.51 (m, 2H), 3.54 (s, 3H), 3.58-3.65 (m, 2H), 4.65 (m, 1H), 7.16-7.19 (m, 2H), 7.49 (d, 1H, J=8.08 Hz).
MS (+ESI) m/z 419 (MH+)

Example 30

6-[4-(2-chloro-5-fluoro-phenoxy)-piperidin-1-yl]-2,4-dimethyl-2H-[1,2,4]triazine-3,5-dione (30)

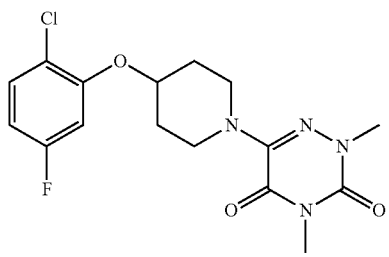 [SMILES: Cn1nc(N2CCC(Oc3cc(F)ccc3Cl)CC2)c(=O)n(C)c1=O]

The compound 30 (solid) is prepared from the triazine 1b and from the intermediate 8b according to the synthesis method 1 in n-butanol (yield: 77%).
TLC silica gel 60 F 254 Merck, CH$_2$Cl$_2$-AcOEt: 95-5, Rf=0.55.
MP=168° C.
$^1$H NMR (CDCl$_3$) ppm: 1.99-2.11 (m, 4H), 3.36 (s, 3H), 3.42-3.49 (m, 2H), 3.54 (s, 3H), 3.61-3,3,67 (m, 2H), 4.55 (m, 1H), 6.62-6.72 (m, 2H), 7.29-7.34 (m, 1H).
MS (+ESI) m/z 369 (MH+)

Example 31

2,4-dimethyl-6-(4-o-tolyloxy-piperidin-1-yl)-2H-[1,2,4]triazine-3,5-dione (31)

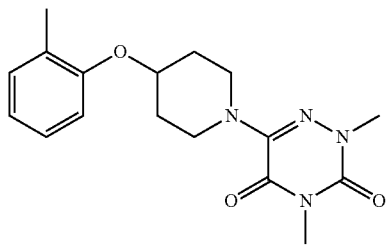 [SMILES: Cc1ccccc1OC1CCN(c2nn(C)c(=O)n(C)c2=O)CC1]

The compound 31 (solid) is prepared from the triazine 1b and from the intermediate 8 g according to the synthesis method 1 in n-butanol (yield: 56%).
TLC silica gel 60 F 254 Merck, CH$_2$Cl$_2$-AcOEt: 95-5, Rf=0.67.
MP=102° C.
$^1$H NMR (CDCl$_3$) ppm: 1.93-1.98 (m, 2H), 2.03-2.09 (m, 2H), 2.24 (s, 3H), 3.36 (s, 3H), 3.36-3.44 (m, 2H), 3.54 (s, 3H), 3.55-3.64 (m, 2H), 4.54 (m, 1H), 6.84-6.89 (m, 2H), 7.12-7.17 (m, 2H).
MS (+ESI) m/z 331 (MH+)

Example 32

2,4-dimethyl-6-[4-(4-trifluoromethyl-phenoxy)-piperidin-1-yl]2H-[1,2,4]triazine-3,5-dione (32)

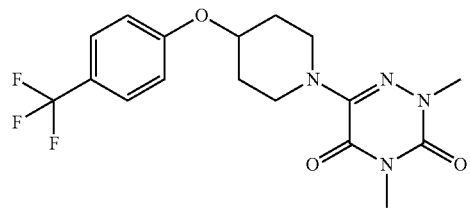 [SMILES: Cn1nc(N2CCC(Oc3ccc(C(F)(F)F)cc3)CC2)c(=O)n(C)c1=O]

The compound 32 (oil) is prepared from the triazine 1b and from the intermediate 8 h according to the synthesis method 1 in n-butanol (yield: 51%).
TLC silica gel 60 F 254 Merck, CH$_2$Cl$_2$-AcOEt: 95-5, Rf=0.49.
MS (+ESI) m/z 385 (MH+)

Example 33

6-[4-(4-fluoro-phenoxy)-piperidin-1-yl]-2,4-dimethyl-2H-[1,2,4]triazine-3,5-dione (33)

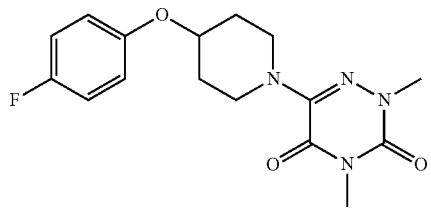 [SMILES: Cn1nc(N2CCC(Oc3ccc(F)cc3)CC2)c(=O)n(C)c1=O]

The compound 33 (solid) is prepared from the triazine 1b and from the intermediate 8d according to the synthesis method 1 in n-butanol (yield: 35%).
TLC silica gel 60 F 254 Merck, CH$_2$Cl$_2$-AcOEt: 90-10, Rf=0.35.
MP=70° C.
$^1$H NMR (CDCl$_3$) ppm: 1.83-1.94 (m, 2H), 1.99-2.09 (m, 2H), 3.26-3.34 (m, 2H), 3.36 (s, 3H), 3.54 (s, 3H), 3.63-3.73 (m, 2H), 4.37-4.44 (m, 1H), 6.83-6.90 (m, 2H), 6.98 (t, 2H, J=8.08 Hz).
MS (+ESI) m/z 335 (MH+)

Example 34

6-[4-(2-methoxy-phenoxy)-piperidin-1-yl]-2,4-dimethyl-2H-[1,2,4]triazine-3,5-dione (34)

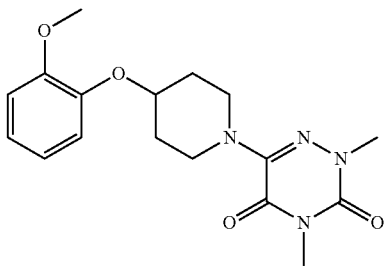 [SMILES: COc1ccccc1OC1CCN(c2nn(C)c(=O)n(C)c2=O)CC1]

The compound 34 (solid) is prepared from the triazine 1b and from the intermediate 81 according to the synthesis method 1 in n-butanol (yield: 77%).

TLC silica gel 60 F 254 Merck, CH$_2$Cl$_2$-AcOEt: 95-5, Rf=0.45.

MP=78° C.

$^1$H NMR (CDCl$_3$) ppm: 1.90-1.98 (m, 2H), 2.02-2.09 (m, 2H), 3.20-3.27 (m, 2H), 3.35 (s, 3H), 3.53 (s, 3H), 3.76-3.83 (m, 2H), 3.85 (s, 3H), 4.41-4.44 (m, 1H), 6.87-6.91 (m, 2H), 6.93-7.01 (m, 2H).

MS (+ESI) m/z 347 (MH+)

Example 35

5-[4-(2-chloro-phenoxy)-piperidin-1-yl]-1,3-dimethyl-1H-pyrimidine-2,4-dione (35)

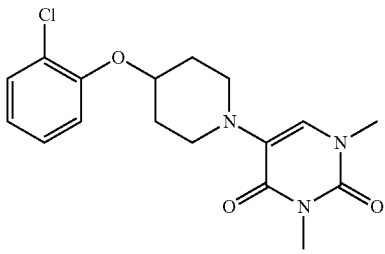 [SMILES: Cn1cc(N2CCC(Oc3ccccc3Cl)CC2)c(=O)n(C)c1=O]

The compound 35 (oil) is prepared from the uracil 1c and from the intermediate 8a according to the synthesis method 1 in n-butanol (yield: 17%).

TLC silica gel 60 F 254 Merck, CH$_2$Cl$_2$-MeOH—NH$_4$OH: 90-9-1, Rf=0.25.

MS (+ESI) m/z 350 (MH+)

Example 36

6-[4-(4-fluoro-benzoyl)-piperidin-1-yl]-2,4-dimethyl-2H-[1,2,4]triazine-3,5-dione (36)

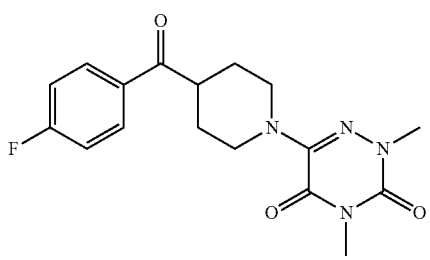 [SMILES: Cn1nc(N2CCC(C(=O)c3ccc(F)cc3)CC2)c(=O)n(C)c1=O]

The compound 36 (solid) is prepared from the triazine 1b and from the intermediate 10 according to the synthesis method 1 in n-butanol (yield: 50%).

TLC silica gel 60 F 254 Merck, CH$_2$Cl$_2$-MeOH: 90-10, Rf=0.78.

MP=129° C.

MS (+ESI) m/z 347 (MH+)

Example 37

2,4-dimethyl-6-[3-(2-trifluoromethyl-phenoxy)-pyrrolidin-1-yl]-2H-[1,2,4]triazine-3,5-dione (37)

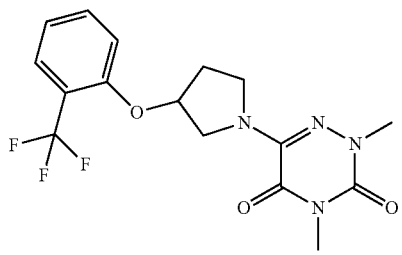 [SMILES: Cn1nc(N2CCC(Oc3ccccc3C(F)(F)F)C2)c(=O)n(C)c1=O]

The compound 37 (solid) is prepared from the triazine 1b and from the intermediate 11a according to the synthesis method 1 in n-butanol (yield: 60%).

TLC silica gel 60 F 254 Merck, CH$_2$Cl$_2$-AcOEt: 90-10, Rf=0.4.

MP=84° C.

MS (+ESI) m/z 371 (MH+)

Example 38

2,4-dimethyl-6-(3-phenoxy-pyrrolidin-1-yl)-2H-[1,2,4]triazine-3,5-dione (38)

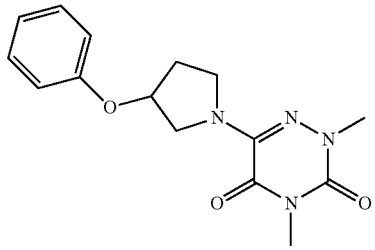 [SMILES: Cn1nc(N2CCC(Oc3ccccc3)C2)c(=O)n(C)c1=O]

The compound 38 (solid) is prepared from the triazine 1b and from the intermediate 11b according to the synthesis method 1 in n-butanol (yield: 72%).

TLC silica gel 60 F 254 Merck, CH$_2$Cl$_2$-AcOEt: 90-10, Rf=0.4.

MP=80° C.

MS (+ESI) m/z 303 (MH+)

Example 39

6-[4-(2-fluoro-5-trifluoromethyl-benzyl)-piperidin-1-yl]-2,4-dimethyl-2H-[1,2,4]triazine-3,5-dione (39)

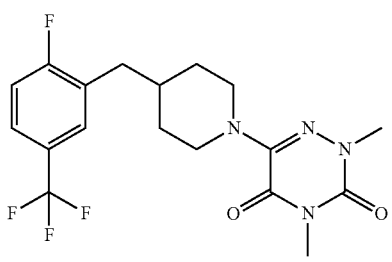

The compound 39 (oil) is prepared from the triazine 1b and from the intermediate 9 according to the synthesis method 1 in n-butanol (yield: 78%).

TLC silica gel 60 F 254 Merck, CH$_2$Cl$_2$-AcOEt: 95-5, Rf=0.46.

MP=116° C.

$^1$H NMR (CDCl$_3$) ppm: 1.39-1.47 (m, 2H), 1.66-1.71 (m, 2H), 1.74-1.80 (m, 1H), 2.59-2.68 (m, 4H), 3.34 (s, 3H), 3.52 (s, 3H), 4.05 (d, 2H, J=12.76 Hz), 7.13 (t, 1H, J=8.90 Hz), 7.43 (d, 1H, J=6.48 Hz), 7.45-7.48 (m, 1H).

MS (+ESI) m/z 401 (MH+)

Example 40

6-[4-(2,5-Bis-trifluoromethyl-benzoyl)-piperazin-1-yl]-2,4-dimethyl-2H-[1,2,4]triazine-3,5-dione (40)

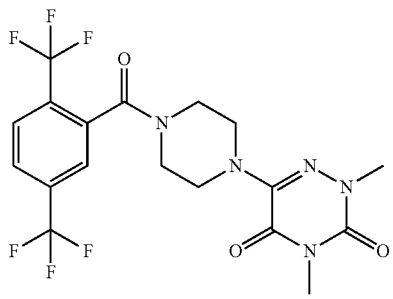 [SMILES: Cn1nc(N2CCN(C(=O)c3cc(C(F)(F)F)ccc3C(F)(F)F)CC2)c(=O)n(C)c1=O]

The compound 40 is prepared according to the synthesis method 2: 0.16 g (0.72 mmol) of derivative 12a is placed in 1 mL of dichloromethane in the presence of 0.15 mL (1.08 mmol) of NEt$_3$ at 0° C. 0.2 g (0.72 mmol) of 2,5-bis-trifluoromethyl-benzoyl chloride is added. This mixture is stirred for 15 min at 0° C., and then for 1 h at room temperature. The medium is taken up with water and extracted with CH$_2$Cl$_2$. After drying on MgSO$_4$, the organic phase is concentrated. The obtained residue is purified by flash chromatography on silica (CH$_2$Cl$_2$-AcOEt: 90-10). 0.24 g of white crystals are isolated (yield: 71%).

TLC silica gel 60 F 254 Merck, CH$_2$Cl$_2$-AcOEt: 95-5, Rf=0.19.

MP=90° C.

MS (+ESI) m/z 466 (MH+)

Example 41

6-[4-(4-fluoro-2-trifluoromethyl-benzoyl)-piperazin-1-yl]-2,4-dimethyl-2H-[1,2,4]triazine-3,5-dione (41)

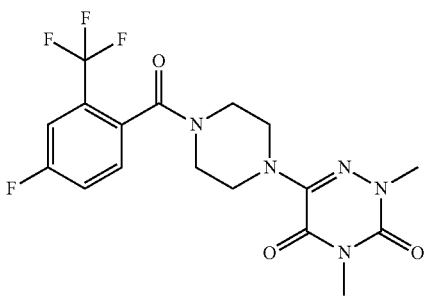

The compound 41 (solid) is prepared from 4-fluoro-2-trifluoromethyl-benzoyl chloride and from the intermediate 12a according to the synthesis method 2 under the operating conditions described for Example 40 (yield: 61%).

TLC silica gel 60 F 254 Merck, CH$_2$Cl$_2$-AcOEt: 95-5, Rf=0.23.

MP=128° C.

MS (+ESI) m/z 416 (MH+)

Example 42

6-[4-(5-fluoro-2-trifluoromethyl-benzoyl)-piperazin-1-yl]-2,4-dimethyl-2H-[1,2,4]triazine-3,5-dione (42)

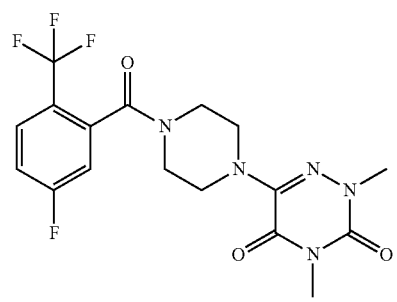

The compound 42 (solid) is prepared from 5-fluoro-2-trifluoromethyl-benzoyl chloride and from the intermediate 12a according to the synthesis method 2 under the operating conditions described for Example 40 (yield: 86%).

TLC silica gel 60 F 254 Merck, CH$_2$Cl$_2$-AcOEt: 95-5, Rf=0.10.

MP=87° C.

$^1$H NMR (CDCl$_3$) ppm: 3.32 (s br, 4H), 3.35 (s, 3H), 3.41-3.49 (m, 1H), 3.49-3.57 (m, 4H), 3.81-3.89 (m, 1H), 3.95-4.02 (m, 1H), 7.07 (d, 1H, J=8.08 Hz), 7.23 (t, 1H, J=8.34 Hz), 7.74 (dd, 1H, J=8.59 Hz and J=5.30 Hz).

MS (+ESI) m/z 416 (MH+)

Example 43

2,4-dimethyl-6-[4-(2-methyl-benzoyl)-piperazin-1-yl]-2H-[1,2,4]triazine-3,5-dione (43)

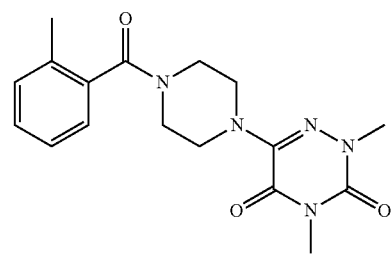 [SMILES: Cc1ccccc1C(=O)N1CCN(c2nn(C)c(=O)n(C)c2=O)CC1]

The compound 43 (solid) is prepared from 2-methyl-benzoyl chloride and from the intermediate 12a according to the synthesis method 2 under the operating conditions described for Example 40 (yield: 70%).

TLC silica gel 60 F 254 Merck, CH$_2$Cl$_2$-AcOEt: 70-30, Rf=0.30.

MP=60° C.

MS (+ESI) m/z 344 (MH+)

Example 44

2,4-dimethyl-6-[4-(3-trifluoromethyl-benzoyl)-piperazin-1-yl]-2H-[1,2,4]triazine-3,5-dione (44)

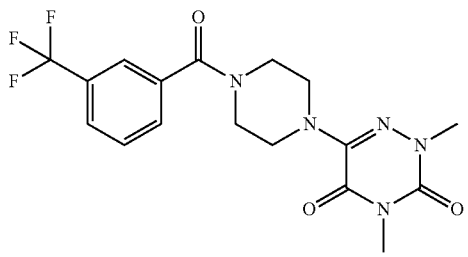 [SMILES: Cn1nc(N2CCN(C(=O)c3cccc(C(F)(F)F)c3)CC2)c(=O)n(C)c1=O]

The compound 44 (solid) is prepared from 3-trifluoromethyl-benzoyl chloride and from the intermediate 12a according to the synthesis method 2 under the operating conditions described for Example 40 (yield: 75%).
TLC silica gel 60 F 254 Merck, CH$_2$Cl$_2$-AcOEt: 70-30, Rf=0.30.
MP=92° C.
MS (+APCI) m/z 398 (MH+)

Example 45

6-[4-(2-bromo-benzoyl)-piperazin-1-yl]-2,4-dimethyl-2H-[1,2,4]triazine-3,5-dione (45)

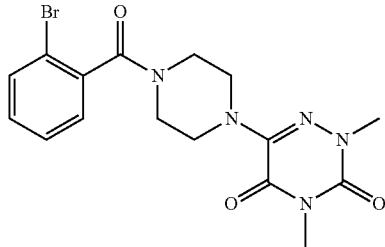 [SMILES: Cn1nc(N2CCN(C(=O)c3ccccc3Br)CC2)c(=O)n(C)c1=O]

The compound 45 (solid) is prepared from 2-bromo-benzoyl chloride and from the intermediate 12a according to the synthesis method 2 under the operating conditions described for Example 40 (yield: 87%).
TLC silica gel 60 F 254 Merck, CH$_2$Cl$_2$-AcOEt: 70-30, Rf=0.30.
MP=119° C.
MS (+APCI) m/z 408 (MH+)

Example 46

6-(4-benzoyl-piperazin-1-yl)-2,4-dimethyl-2H-[1,2,4]triazine-3,5-dione (46)

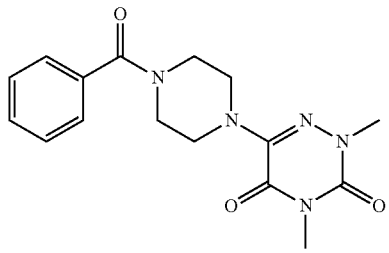 [SMILES: Cn1nc(N2CCN(C(=O)c3ccccc3)CC2)c(=O)n(C)c1=O]

The compound 46 (solid) is prepared from benzoyl chloride and from the intermediate 12a according to the synthesis method 2 under the operating conditions described for Example 40 (quantitative yield).
TLC silica gel 60 F 254 Merck, CH$_2$Cl$_2$-AcOEt: 70-30, Rf=0.26.
MP=132° C.
MS (+APCI) m/z 330 (MH+)

Example 47

6-[4-(5-fluoro-2-trifluoromethyl-benzoyl)-piperazin-1-yl]-4-methyl-2-(4,4,4-trifluoro-butyl)-2H-[1,2,4]triazine-3,5-dione (47)

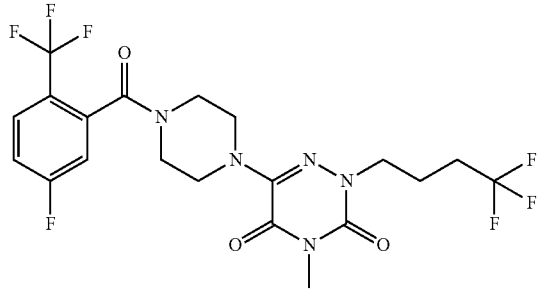 [SMILES: Cn1c(=O)c(N2CCN(C(=O)c3cc(F)ccc3C(F)(F)F)CC2)nn(CCCC(F)(F)F)c1=O]

The compound 47 (solid) is prepared from 5-fluoro-2-trifluoromethyl-benzoyl chloride and from the intermediate 12d according to the synthesis method 2 under the operating conditions described for Example 40 (yield: 91%).
TLC silica gel 60 F 254 Merck, CH$_2$Cl$_2$-MeOH: 90-10, Rf=0.78.
$^1$H NMR (CDCl$_3$) ppm: 1.95-2.07 (m, 2H), 2.07-2.22 (m, 2H), 3.28-3.34 (m, 4H), 3.34 (s, 3H), 3.43-3.59 (m, 2H), 3.81-3.91 (m, 1H), 3.91-4.03 (m, 3H), 7.07 (d, 1H, J=7.58 Hz), 7.23 (t, 1H, J=8.83 Hz), 7.74 (dd, 1H, J=8.84 Hz and J=5.05 Hz).
MS (+ESI) m/z 512 (MH+)

Example 48

6-[4-(5-fluoro-2-trifluoromethyl-benzoyl)-piperazin-1-yl]-4-methyl-2-(3-methyl-butyl)-2H-[1,2,4]triazine-3,5-dione (48)

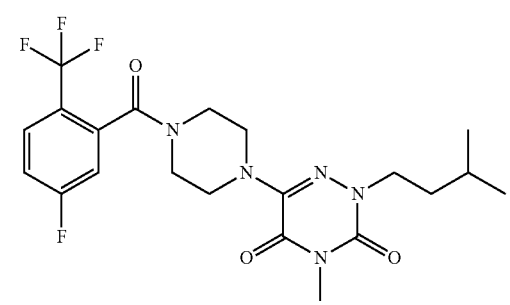

The compound 48 (oil) is prepared from 5-fluoro-2-trifluoromethyl-benzoyl chloride and from the intermediate 12f according to the synthesis method 2 under the operating conditions described for Example 40 (yield: 58%).

TLC silica gel 60 F 254 Merck, CH$_2$Cl$_2$-MeOH: 90-10, Rf=0.28.

$^1$H NMR (CDCl$_3$) ppm: 0.93-0.97 (m, 6H), 1.56-1.63 (m, 3H), 3.29-3.33 (m, 4H), 3.35 (s, 3H), 3.43-3.56 (m, 2H), 3.82-3.93 (m, 3H), 4.02-3.93 (m, 1H), 7.07 (d, 1H, J=7.83 Hz), 7.23 (t, 1H, J=8.34 Hz), 7.73 (dd, 1H, J=8.33 Hz and J=5.05 Hz)

MS (+ESI) m/z 472 (MH+)

Example 49

6-{4-[2-(4-chloro-phenyl)-3-methyl-butyryl]-piperazin-1-yl}-2,4-dimethyl-2H-[1,2,4]triazine-3,5-dione (49)

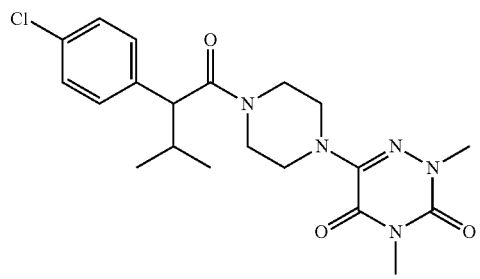 [SMILES: CC(C)C(C(=O)N1CCN(c2nn(C)c(=O)n(C)c2=O)CC1)c1ccc(Cl)cc1]

The compound 49 (solid) is prepared from 2-(4-chlorophenyl)-3-methyl-butyryl chloride and from the intermediate 12a according to the synthesis method 2 under the operating conditions described for Example 40 (yield: 90%).

TLC silica gel 60 F 254 Merck, petroleum ether-AcOEt: 60-40, Rf=0.36.

MP=58° C.

MS (+APCI) m/z 420 (MH+)

Example 50

2,4-dimethyl-6-{4-[(E)-3-(4-nitro-phenyl)-acryloyl]-piperazin-1-yl}-2H-[1,2,4]triazine-3,5-dione (50)

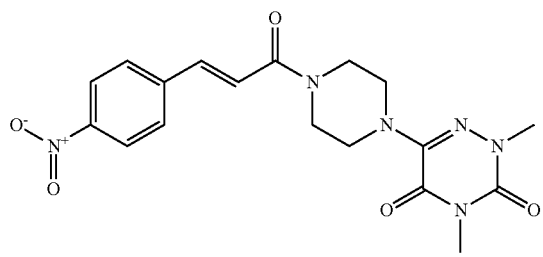 [SMILES: Cn1nc(N2CCN(C(=O)/C=C/c3ccc([N+](=O)[O-])cc3)CC2)c(=O)n(C)c1=O]

The compound 50 (solid) is prepared from (E)-3-(4-nitrophenyl)-acryloyl chloride and from the intermediate 12a according to the synthesis method 2 under the operating conditions described for Example 40 (yield: 8%).

TLC silica gel 60 F 254 Merck, CH$_2$Cl$_2$-AcOEt: 80-20, Rf=0.19.

MP=198° C.

MS (+ESI) m/z 401 (MH+)

Example 51

4-(2,4-dimethyl-3,5-dioxo-2,3,4,5-tetrahydro-[1,2,4]triazin-6-yl)-piperazine-1-carboxylic Acid 3-trifluoromethyl-phenyl Ester (51)

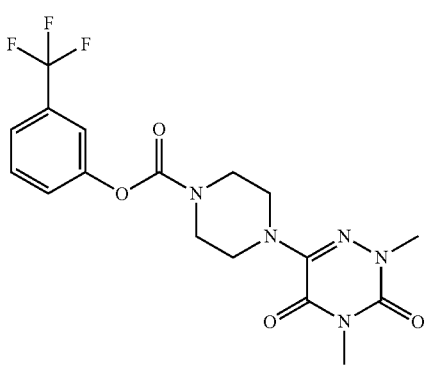 [SMILES: Cn1nc(N2CCN(C(=O)Oc3cccc(C(F)(F)F)c3)CC2)c(=O)n(C)c1=O]

The compound 51 (solid) is prepared from 3-trifluoromethyl-phenylchloroformate and from the intermediate 12a according to the synthesis method 2 under the operating conditions described for Example 40 (yield: 27%).

TLC silica gel 60 F 254 Merck, CH$_2$Cl$_2$-MeOH—NH$_4$OH: 90-9-1, Rf=0.9.

MP=93° C.

MS (+ESI) m/z 414 (MH+)

Example 52

6-{4-[(E)-3-(2-bromo-phenyl)-acryloyl]-piperazin-1-yl}-2,4-dimethyl-2H-[1,2,4]triazine-3,5-dione (52)

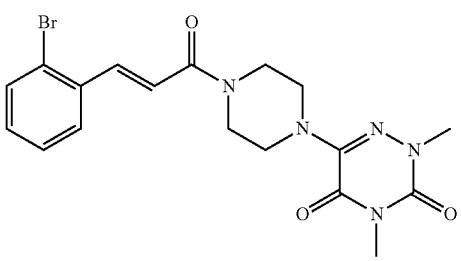 [SMILES: Cn1nc(N2CCN(C(=O)/C=C/c3ccccc3Br)CC2)c(=O)n(C)c1=O]

The compound 52 (glassy solid) is prepared from the acrylic acid of (E)-3-(2-bromo-phenyl) converted into an acid chloride (SOCl$_2$, toluene, 100° C., 3 h), and from the intermediate 12a according to the synthesis method 2 under the operating conditions described for Example 40 (yield: 90%).

TLC silica gel 60 F 254 Merck, CH$_2$Cl$_2$-AcOEt: 80-20, Rf=0.7.

MS (+ESI) m/z 546 (MH+)

Example 53

2,4-dimethyl-6-[3-oxo-4-(2-trifluoromethyl-benzoyl)-piperazin-1-yl]-2H-[1,2,4]triazine-3,5-dione (53)

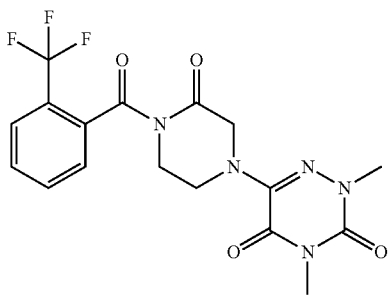 [SMILES: Cn1nc(N2CCN(C(=O)c3ccccc3C(F)(F)F)C(=O)C2)c(=O)n(C)c1=O]

The compound 53 (solid) is prepared from 2-trifluoromethyl-benzoyl chloride and from the intermediate 12b according to the synthesis method 2 under the operating conditions described for Example 40 (yield: 77%).

TLC silica gel 60 F 254 Merck, CH$_2$Cl$_2$-MeOH: 90-10, Rf=0.83.

MP=90° C.

MS (+ESI) m/z 412 (MH+)

Example 54

6-[4-(4-fluoro-2-trifluoromethyl-benzyl)-piperazin-1-yl]-2,4-dimethyl-2H-[1,2,4]triazine-3,5-dione (54)

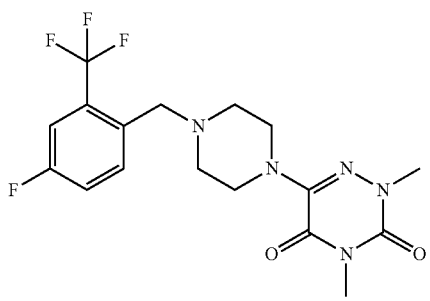 [SMILES: Cn1nc(N2CCN(Cc3ccc(F)cc3C(F)(F)F)CC2)c(=O)n(C)c1=O]

The compound 54 is prepared according to the synthesis method 2: 0.26 g (1.17 mmol) of derivative 12a is placed in 3 mL of toluene in the presence of 0.24 mL (1.75 mmol) of NEt$_3$ and of 0.3 g (1.17 mmol) of 1-bromomethyl-4-fluoro-2-trifluoromethyl-benzene. This mixture is stirred 2 h at 110° C. The medium is taken up with water and extracted with AcOEt. After drying on MgSO$_4$, the organic phase is dry concentrated. The obtained residue is purified by flash chromatography on silica (CH$_2$Cl$_2$-AcOEt: 95-5). 0.37 g of a yellow oil are isolated (yield: 79%).

TLC silica gel 60 F 254 Merck, CH$_2$Cl$_2$-AcOEt: 95-5, Rf=0.29.

MS (+ESI) m/z 402 (MH+)

Example 55

2,4-dimethyl-6-[4-(2-trifluoromethyl-benzyl)-piperazin-1-yl]-2H-[1,2,4]triazine-3,5-dione (55)

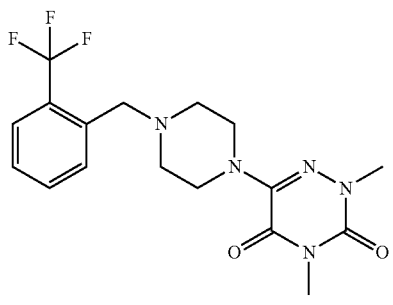

The compound 55 (solid) is prepared from 1-bromomethyl-2-trifluoromethyl-benzene and from the intermediate 12a according to the synthesis method 2 under the operating conditions described for Example 54 (yield: 92%).

TLC silica gel 60 F 254 Merck, petroleum ether-AcOEt: 80-20, Rf=0.25.

MP=92° C.

$^1$H NMR (CDCl$_3$) ppm: 2.56-2.64 (m, 4H), 3.34 (s, 3H), 3.39-3.47 (m, 4H), 3.53 (s, 3H), 3.70 (s, 2H), 7.34 (t, 1H, J=7.58 Hz), 7.52 (t, 1H, J=7.83 Hz) 7.63 (d, 1H, J=7.83 Hz), 7.80 (d, 1H, J=7.58 Hz)

MS (+APCI) m/z 384 (MH+)

Example 56

2-butyl-4-methyl-6-[4-(2-trifluoromethyl-benzyl)-piperazin-1-yl]-2H-[1,2,4]triazine-3,5-dione (56)

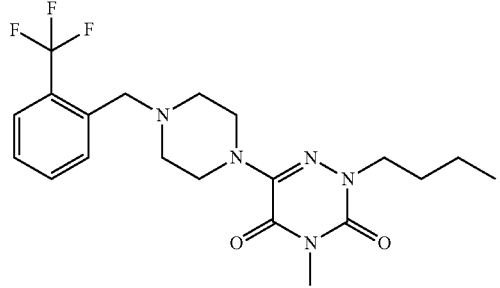 [SMILES: CCCCn1nc(N2CCN(Cc3ccccc3C(F)(F)F)CC2)c(=O)n(C)c1=O]

The compound 56 (oil) is prepared from 1-bromomethyl-2-trifluoromethyl-benzene and from the intermediate 12e according to the synthesis method 2 under the operating conditions described for Example 54 (yield: 84%).

TLC silica gel 60 F 254 Merck, CH$_2$Cl$_2$-AcOEt: 95-5, Rf=0.36.

MS (+ESI) m/z 426 (MH+)

Example 57

4-methyl-2-(4,4,4-trifluoro-butyl)-6-[4-(2-trifluoromethyl-benzyl)-piperazin-1-yl]-2H-[1,2,4]triazine-3,5-dione (57)

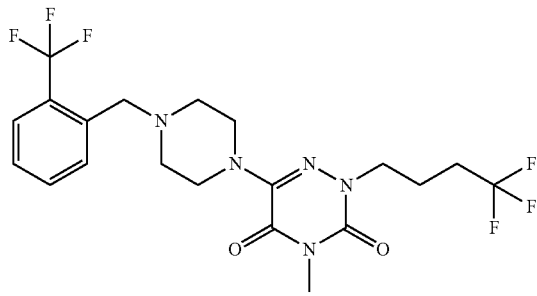 [SMILES: Cn1c(=O)c(N2CCN(Cc3ccccc3C(F)(F)F)CC2)nn(CCCC(F)(F)F)c1=O]

The compound 57 (solid) is prepared from 1-bromomethyl-2-trifluoromethyl-benzene and from the intermediate 12d according to the synthesis method 2 under the operating conditions described for Example 54 (yield: 66%).

TLC silica gel 60 F 254 Merck, CH$_2$Cl$_2$-MeOH: 90-10, Rf=0.65.

$^1$H NMR (CDCl$_3$) ppm: 1.95-2.06 (m, 2H), 2.09-2.23 (m, 2H), 2.56-2.63 (m, 4H), 3.34 (s, 3H), 3.42-3.48 (m, 4H), 3.70 (s, 2H), 3.95 (t, 2H, J=6.57 Hz), 7.35 (t, 1H, J=7.58 Hz), 7.52 (t, 1H, J=7.58 Hz), 7.62 (d, 1H, J=7.58 Hz), 7.79 (d, 1H, J=8.08 Hz).

MS (+ESI) m/z 480 (MH+)

Example 58

2,4-dimethyl-6-[3-methyl-4-(2-trifluoromethyl-benzyl)-piperazin-1-yl]-2H-[1,2,4]triazine-3,5-dione (58)

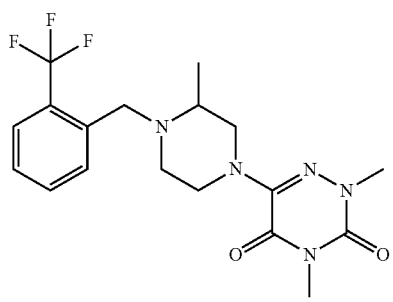 [SMILES: CC1CN(c2nn(C)c(=O)n(C)c2=O)CCN1Cc1ccccc1C(F)(F)F]

The compound 58 (oil) is prepared from 1-bromomethyl-2-trifluoromethyl-benzene and from the intermediate 12c according to the synthesis method 2 under the operating conditions described for Example 54 (yield: 76%).

TLC silica gel 60 F 254 Merck, CH$_2$Cl$_2$-AcOEt: 95-5, Rf=0.40.

MS (+ESI) m/z 398 (MH+)

Example 59

5-(4-benzyl-piperazin-1-yl)-1,3-dimethyl-1H-pyrimidine-2,4-dione (59)

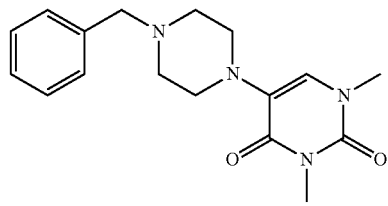 [SMILES: Cn1cc(N2CCN(Cc3ccccc3)CC2)c(=O)n(C)c1=O]

The compound 59 (solid) is prepared according to the synthesis method described in the intermediate paragraph 13a (yield: 54%).

TLC silica gel 60 F 254 Merck, CH$_2$Cl$_2$-MeOH—NH$_4$OH: 90-9-1, Rf=0.64.

MP=162° C.

MS (+ESI) m/z 315 (MH+)

Example 60

5-[4-(4-fluoro-2-trifluoromethyl-benzoyl)-piperazin-1-yl]-1,3-dimethyl-1H-pyrimidine-2,4-dione (60)

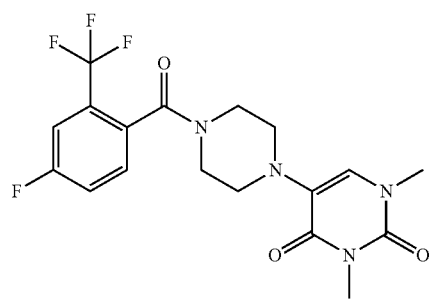 [SMILES: Cn1cc(N2CCN(C(=O)c3ccc(F)cc3C(F)(F)F)CC2)c(=O)n(C)c1=O]

The compound 60 (solid) is prepared from 4-fluoro-2-trifluoromethyl-benzoyl chloride and from the intermediate 13b according to the synthesis method 2 under the operating conditions described for Example 40 (yield: 65%).

TLC silica gel 60 F 254 Merck, CH$_2$Cl$_2$-MeOH—NH$_4$OH: 90-9-1, Rf=0.57.

MS (+ESI) m/z 415 (MH+)

Example 61

5-[4-(5-fluoro-2-trifluoromethyl-benzoyl)-piperazin-1-yl]-1,3-dimethyl-1H-pyrimidine-2,4-dione (61)

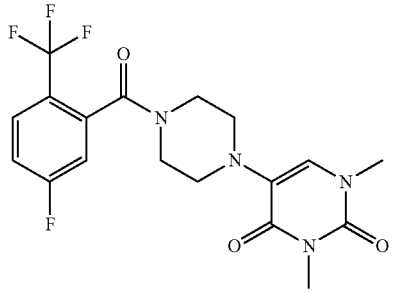

The compound 61 (solid) is prepared from 5-fluoro-2-trifluoromethyl-benzoyl chloride and from the intermediate 13b according to the synthesis method 2 under the operating conditions described for Example 40 (yield: 80%).

TLC silica gel 60 F 254 Merck, $CH_2Cl_2$-MeOH—$NH_4OH$: 90-9-1, Rf=0.60.

MS (+ESI) m/z 415 (MH+)

Example 62

1,3-dimethyl-5-[4-(2-trifluoromethyl-benzoyl)-piperazin-1-yl]-1H-pyrimidine-2,4-dione (62)

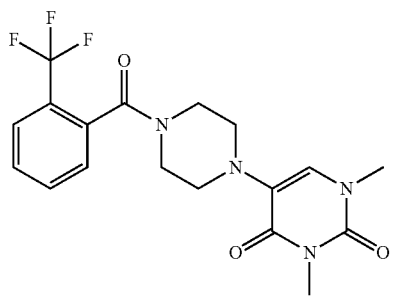 [SMILES: Cn1cc(N2CCN(C(=O)c3ccccc3C(F)(F)F)CC2)c(=O)n(C)c1=O]

The compound 62 (solid) is prepared from 2-trifluoromethyl-benzoyl chloride and from the intermediate 13b according to the synthesis method 2 under the operating conditions described for Example 40 (yield: 59%).

TLC silica gel 60 F 254 Merck, $CH_2Cl_2$-MeOH: 98-2, Rf=0.2.

MP=163° C.

MS (+APCI) m/z 397 (MH+)

Example 63

5-[4-(4-fluoro-2-trifluoromethyl-benzyl)-piperazin-1-yl]-1,3-dimethyl-1H-pyrimidine-2,4-dione (63)

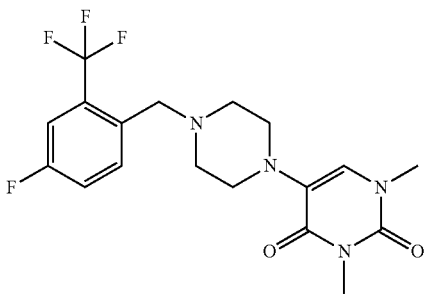 [SMILES: Cn1cc(N2CCN(Cc3ccc(F)cc3C(F)(F)F)CC2)c(=O)n(C)c1=O]

The compound 63 (oil) is prepared from 1-bromomethyl-4-fluoro-2-trifluoromethyl-benzene and from the intermediate 13b according to the synthesis method 2 under the operating conditions described for Example 54 (yield: 67%).

TLC silica gel 60 F 254 Merck, $CH_2Cl_2$-MeOH: 90-10, Rf=0.60.

MS (+ESI) m/z 401 (MH+)

Example 64

4-methyl-6-[4-(2-trifluoromethyl-benzyl)-piperazin-1-yl]-2H-[1,2,4]triazine-3,5-dione (64)

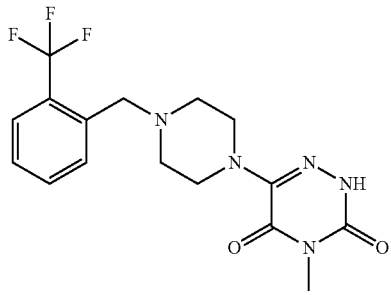 [SMILES: Cn1c(=O)[nH]nc(N2CCN(Cc3ccccc3C(F)(F)F)CC2)c1=O]

The compound 64 is prepared from the triazine 4b and from the intermediate 7a according to the synthesis method 1 in n-butanol. After deprotection of the nitrogen in position 2 ($NH_2NH_2.H_2O$, EtOH, 78° C., 3 h), the compound 64 is obtained as a solid (yield: 64%).

TLC silica gel 60 F 254 Merck, $CH_2Cl_2$-AcOEt: 90-10, Rf=0.15.

MP=205° C.

$^1$H NMR ($CDCl_3$) ppm: 2.56-2.63 (m, 4H), 3.34 (s, 3H), 3.39-3.47 (m, 4H), 3.70 (s, 2H), 7.34 (t, 1H, J=7.58 Hz), 7.52 (t, 1H, J=7.58 Hz), 7.63 (d, 1H, J=7.58 Hz), 7.79 (d, 1H, J=8.08 Hz), 8.65 (s, 1H).

MS (+ESI) m/z 370 (MH+)

Example 65

6-[4-(3-fluoro-phenyl)-piperazin-1-yl]-4-methyl-2H-[1,2,4]triazine-3,5-dione (65)

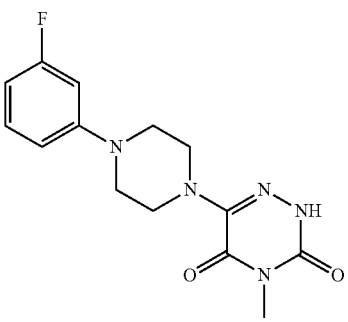 [SMILES: Cn1c(=O)[nH]nc(N2CCN(c3cccc(F)c3)CC2)c1=O]

The compound 65 is prepared from the triazine 4b and from 1-(3-fluoro-phenyl)-piperazine according to the synthesis method 1 in n-butanol. After deprotection of the nitrogen in position 2 ($NH_2NH_2.H_2O$, EtOH, 78° C., 3 h), the compound 65 is obtained as a solid (yield: 17%).

TLC silica gel 60 F 254 Merck, $CH_2Cl_2$-AcOEt: 90-10, Rf=0.14.

MS (+ESI) m/z 306 (MH+)

Example 66

4-methyl-6-[4-(3-trifluoromethyl-phenyl)-piperazin-1-yl]-2H-[1,2,4]triazine-3,5-dione (66)

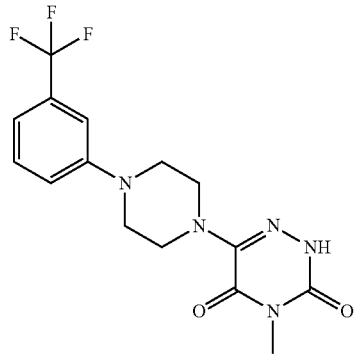 [SMILES: Cn1c(=O)[nH]nc(N2CCN(c3cccc(C(F)(F)F)c3)CC2)c1=O]

The compound 66 is prepared from the triazine 4b and from 1-(3-trifluoromethyl-phenyl)-piperazine according to the synthesis method 1 in n-butanol. After deprotection of the nitrogen in position 2 ($NH_2NH_2 \cdot H_2O$, EtOH, 78° C., 3 h), the compound 66 is obtained as a solid (yield: 73%).

TLC silica gel 60 F 254 Merck, $CH_2Cl_2$-MeOH: 95-5, Rf=0.55.

MS (+ESI) m/z 356 (MH+)

Example 67

6-[4-(3-chloro-phenyl)-piperazin-1-yl]-4-methyl-2H-[1,2,4]triazine-3,5-dione (67)

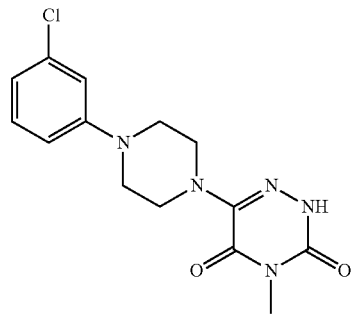 [SMILES: Cn1c(=O)[nH]nc(N2CCN(c3cccc(Cl)c3)CC2)c1=O]

The compound 67 is prepared from the triazine 4b and from 1-(3-chloro-phenyl)-piperazine according to the synthesis method 1 in n-butanol. After deprotection of the nitrogen in position 2 ($NH_2NH_2 \cdot H_2O$, EtOH, 78° C., 3 h), the compound 67 is obtained as a solid (yield: 77%).

TLC silica gel 60 F 254 Merck, $CH_2Cl_2$-MeOH: 95-5, Rf=0.53.

MS (+ESI) m/z 322 (MH+)

Example 68

6-[4-(2,5-Bis-trifluoromethyl-benzoyl)-piperazin-1-yl]-4-methyl-2H-[1,2,4]triazine-3,5-dione (68)

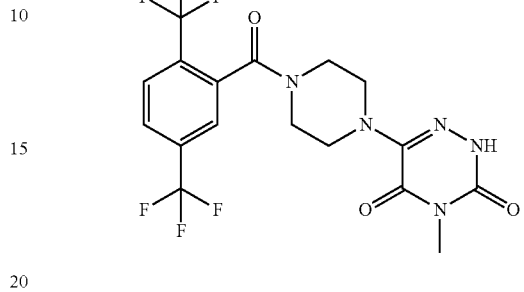

The compound 68 is prepared from the triazine 4b and from the intermediate 6a according to the synthesis method 1 in n-butanol. After deprotection of the nitrogen in position 2 ($NH_2NH_2 \cdot H_2O$, EtOH, 78° C., 3 h), the compound 68 is obtained as a solid (yield: 86%).

TLC silica gel 60 F 254 Merck, $CH_2Cl_2$-MeOH: 95-5, Rf=0.62.

MS (+ESI) m/z 452 (MH+)

Example 69

6-[4-(5-fluoro-2-trifluoromethyl-benzoyl)-piperazin-1-yl]-4-methyl-2H-[1,2,4]triazine-3,5-dione (69)

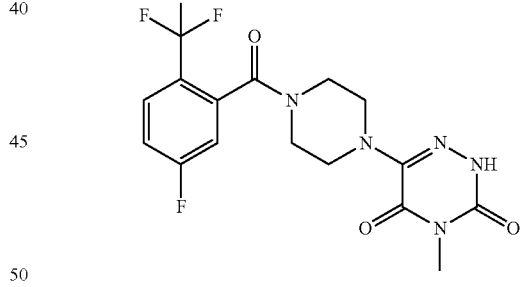

The compound 69 is prepared from the triazine 4b and from the intermediate 6c according to the synthesis method 1 in n-butanol. After deprotection of the nitrogen in position 2 ($NH_2NH_2 \cdot H_2O$, EtOH, 78° C., 3 h), the compound 69 is obtained as a solid (yield: 63%).

TLC silica gel 60 F 254 Merck, $CH_2Cl_2$-MeOH: 95-5, Rf=0.17.

$^1$H NMR (CDCl$_3$) ppm: 3.30-3.32 (m, 4H), 3.34 (s, 3H), 3.40-3.48 (m, 1H), 3.47-3.55 (m, 1H), 3.81-3.88 (m, 1H), 3.95-4.02 (m, 1H), 7.07 (dd, 1H, J=2.05 Hz and J=8.34 Hz), 7.20-7.26 (m, 1H), 7.74 (dd, 1H, J=5.05 Hz and J=8.84 Hz), 8.62 (s, br, 1H).

MS (+ESI) m/z 402 (MH+)

Example 70

6-[4-(4-fluoro-2-trifluoromethyl-benzoyl)-piperazin-1-yl]-4-methyl-2H-[1,2,4]triazine-3,5-dione (70)

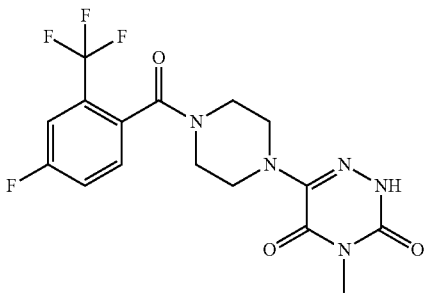 [SMILES: Cn1c(=O)[nH]nc(N2CCN(C(=O)c3ccc(F)cc3C(F)(F)F)CC2)c1=O]

The compound 70 is prepared from the triazine 4b and from the intermediate 6d according to the synthesis method 1 in n-butanol. After deprotection of the nitrogen in position 2 (NH$_2$NH$_2$.H$_2$O, EtOH, 78° C., 3 h), the compound 70 is obtained as a solid (yield: 66%).

TLC silica gel 60 F 254 Merck, CH$_2$Cl$_2$-MeOH: 95-5, Rf=0.36.

$^1$H NMR (CDCl$_3$) ppm: 3.28-3.31 (m, 4H), 3.34 (s, 3H), 3.38-3.46 (m, 1H), 3.49-3.56 (m, 1H), 3.79-3.86 (m, 1H), 3.97-4.04 (m, 1H), 7.29-7.38 (m, 2H), 7.44 (dd, 1H, J=2.52 Hz and J=8.84 Hz), 8.62 (s, br, 1H).

MS (+APCI) m/z 402 (MH+)

Example 71

6-[4-(4-fluoro-2-trifluoromethyl-benzyl)-piperazin-1-yl]-4-methyl-2H-[1,2,4]triazine-3,5-dione (71)

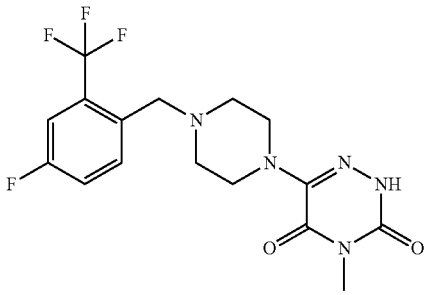 [SMILES: Cn1c(=O)[nH]nc(N2CCN(Cc3ccc(F)cc3C(F)(F)F)CC2)c1=O]

The compound 71 is prepared from the triazine 4b and from the intermediate 7b according to the synthesis method 1 in n-butanol. After deprotection of the nitrogen in position 2 (NH$_2$NH$_2$.H$_2$O, EtOH, 78° C., 3 h), the compound 71 is obtained as a solid (yield: 34%).

TLC silica gel 60 F 254 Merck, CH$_2$Cl$_2$-MeOH: 95-5, Rf=0.64.

$^1$H NMR (CDCl$_3$) ppm: 2.56-2.62 (m, 4H), 3.33 (s, 3H), 3.39-3.42 (m, 4H), 3.65 (s, 2H), 7.22 (m, 1H), 7.34 (d, 1H, J=8.96 Hz), 7.78 (t, 1H, J=6.56 Hz), 8.60 (s, br, 1H).

MS (+ESI) m/z 388 (MH+)

Example 72

4-(4,4,4-trifluoro-butyl)-6-[4-(2-trifluoromethyl-phenoxy)-piperidin-1-yl]-2H-[1,2,4]triazine-3,5-dione (72)

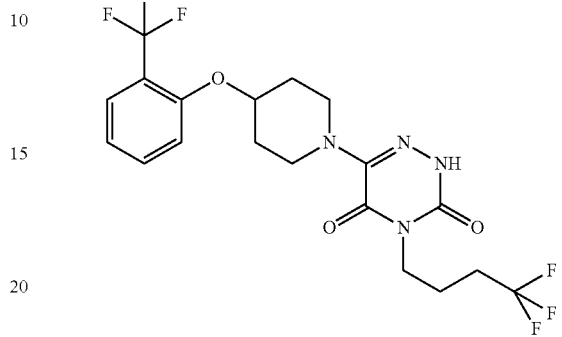

The compound 72 is prepared from the triazine 3b and from the intermediate 8c according to the synthesis method 1 in n-butanol. After deprotection of the nitrogen in position 2 (Na, EtOH, 80° C., 5 h), the compound 72 is obtained as a solid (yield: 38%).

TLC silica gel 60 F 254 Merck, CH$_2$Cl$_2$-AcOEt: 90-10, Rf=0.5.

MP=102° C.

MS (+ESI) m/z 467 (MH+)

Example 73

2-heptyl-4-methyl-6-[4-(2-trifluoromethyl-benzoyl)-piperazin-1-yl]-2H-[1,2,4]triazine-3,5-dione (73)

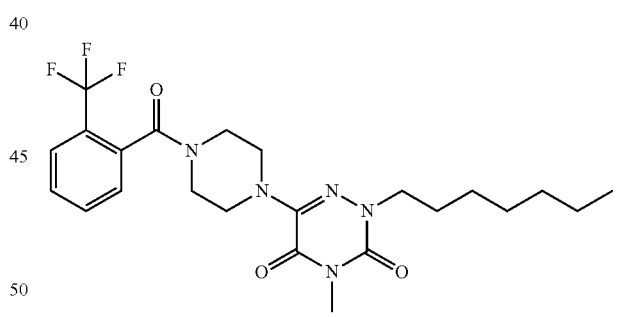

The compound 73 is prepared according to the synthesis method 3: 0.20 g (0.52 mmol) of the compound described for Example 4 is placed in 2 mL of dimethylformamide at 0° C. 0.023 g (0.57 mmol) of NaH are added. The mixture is stirred for 30 min at room temperature. 0.12 g (0.57 mmol) of 1-bromo-heptane in 1 mL of dimethylformamide are added. This mixture is stirred for 4 h 30 min at room temperature. After concentration, the residue is taken up with water and extracted with AcOEt. After drying on MgSO$_4$, the organic phase is concentrated. The obtained residue is purified by flash chromatography on silica (CH$_2$Cl$_2$-AcOEt: 90-10). 0.21 g of a yellow oil are isolated (yield: 84%).

TLC silica gel 60 F 254 Merck, CH$_2$Cl$_2$-MeOH: 95-5, Rf=0.5.

MS (+ESI) m/z 482 (MH+)

Example 74

2-butyl-4-methyl-6-[4-(2-trifluoromethyl-benzoyl)-piperazin-1-yl]-2H-[1,2,4]triazine-3,5-dione (74)

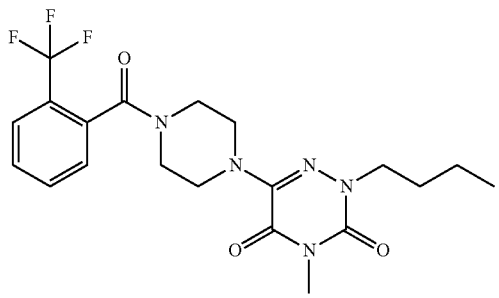 [SMILES: CCCCn1nc(N2CCN(C(=O)c3ccccc3C(F)(F)F)CC2)c(=O)n(C)c1=O]

The compound 74 (oil) is prepared from 1-bromo-butane and from the compound described for Example 4 according to the synthesis method 3 (yield: 70%).

TLC silica gel 60 F 254 Merck, petroleum ether-AcOEt: 50-50, Rf=0.35.

$^1$H NMR (CDCl$_3$) ppm: 0.93-0.96 (t, 3H, J=7.6 Hz) 1.29-1.40 (m, 2H), 1.64-1.73 (m, 2H), 3.26-3.32 (m, 4H), 3.34 (s, 3H), 3.40-3.60 (m, 2H), 3.82-3.91 (m, 3H), 3.97-4.06 (m, 1H), 7.35 (d, 1H, J=7.83 Hz), 7.54 (t, 1H, J=7.83 Hz) 7.62 (t, 1H, J=7.07 Hz), 7.72 (d, 1H, J=8.08 Hz)

MS (+ESI) m/z 440 (MH+)

Example 75

4-methyl-2-(3-methyl-butyl)-6-[4-(2-trifluoromethyl-benzoyl)-piperazin-1-yl]-2H-[1,2,4]triazine-3,5-dione (75)

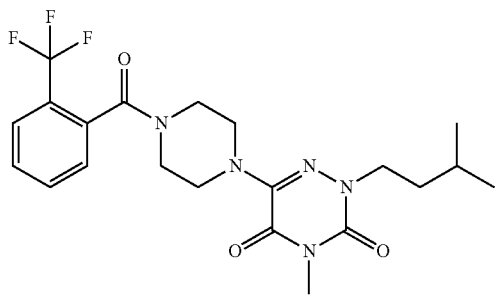 [SMILES: CC(C)CCn1nc(N2CCN(C(=O)c3ccccc3C(F)(F)F)CC2)c(=O)n(C)c1=O]

The compound 75 (oil) is prepared from 1-bromo-3-methyl-butane and from the compound described for Example 4 according to the synthesis method 3 (yield: 79%).

TLC silica gel 60 F 254 Merck, petroleum ether-AcOEt: 50-50, Rf=0.35.

MS (+ESI) m/z 454 (MH+)

Example 76

6-[4-(2-chloro-phenoxy)-piperidin-1-yl]-4-heptyl-2H-[1,2,4]triazine-3,5-dione (76)

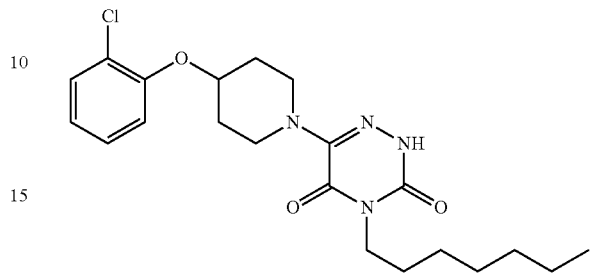

The compound 76 is prepared from the triazine 3c and from the intermediate 8a according to the synthesis method 1 in n-butanol. After deprotection of the nitrogen in position 2 (NaH, DMF, 20° C., 3 h), the compound 76 is obtained as a solid (yield: 67%).

TLC silica gel 60 F 254 Merck, CH$_2$Cl$_2$-AcOEt: 90-10, Rf=0.55.

MP=95° C.

$^1$H NMR (CDCl$_3$) ppm: 0.88 (t, 3H, J=6.82 Hz), 1.22-1.38 (m, 8H), 1.60-1.69 (m, 2H), 1.94-2.09 (m, 4H), 3.38-3.46 (m, 2H). 3.57-3.65 (m, 2H), 3.91 (t, 2H, J=6.56 Hz), 4.58 (m, 1H), 6.91 (t, 1H, J=7.32 Hz), 7.00 (d, 1H, J=8.59 Hz), 7.20 (t, 1H, J=8.08 Hz), 7.37 (d, 1H, J=8.08 Hz), 8.72 (s br, 1H).

MS (+ESI) m/z 421 (MH+)

Example 77

6-[4-(4-fluoro-2-trifluoromethyl-benzyl)-piperidin-1-yl]-2,4-dimethyl-2H-[1,2,4]triazine-3,5-dione (77)

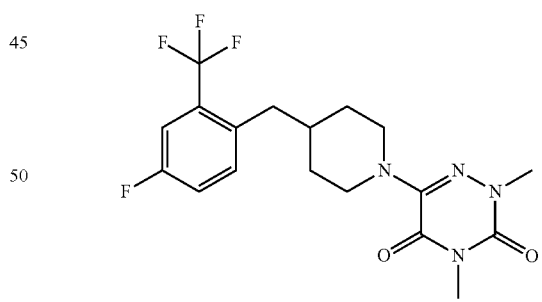

The compound 77 (oil) is prepared from the triazine 1b and from the intermediate 9b according to the synthesis method 1 in n-butanol (yield: 43%).

TLC silica gel 60 F 254 Merck, CH$_2$Cl$_2$-AcOEt: 95-5, Rf=0.48.

$^1$H NMR (CDCl$_3$) ppm: 1.38-1.50 (m, 2H), 1.64-1.79 (m, 3H), 2.60 (t, 2H, J=12.6 Hz), 2.72 (d, 2H, J=6.82 Hz), 3.34 (s, 3H), 3.52 (s, 3H), 4.05 (d, 2H, J=12.3 Hz), 7.17 (t, 1H, J=8.33 Hz), 7.25-7.30 (m, 1H), 7.32-7.38 (m, 1H).

MS (+ESI) m/z 401 (MH+)

Example 78

4-methyl-2-(2-thiophen-2-yl-ethyl)-6-[4-(2-trifluoromethyl-phenoxy)-piperidin-1-yl]-2H-[1,2,4]triazine-3,5-dione (78)

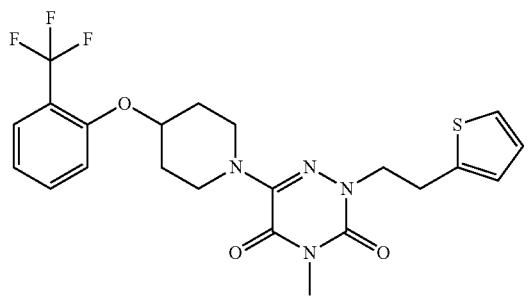 [SMILES: Cn1c(=O)c(N2CCC(Oc3ccccc3C(F)(F)F)CC2)nn(CCc2cccs2)c1=O]

The compound 78 (solid) is prepared from the triazine 4k and from the intermediate 8c according to the synthesis method 1 in n-butanol (yield: 41%).

$^1$H NMR (CDCl$_3$) ppm: 1.93-2.07 (m, 4H), 3.27 (t, 2H, J=7.32 Hz), 3.43 (s, 3H), 3.43-3.54 (m, 4H), 4.17 (t, 2H, J=7.20 Hz), 4.69 (m, 1H), 6.83 (dd, 1H, J=3.53 Hz and J=1.01 Hz), 6.92 (dd, 1H, J=5.18 Hz and J=3.16 Hz), 7.00 (d, 1H, J=8.46 Hz), 7.00 (t, 1H, J=7.58 Hz), 7.14 (dd, 1H, J=5.18 Hz and J=1.26 Hz), 7.48 (t, 1H, J=7.7 Hz), 7.59 (d, 1H, J=7.7 Hz).

MS (+ESI) m/z 481 (MH+)

Example 79

4-methyl-2-o-tolyl-6-[4-(2-trifluoromethyl-phenoxy)-piperidin-1-yl]-2H-[1,2,4]triazine-3,5-dione (79)

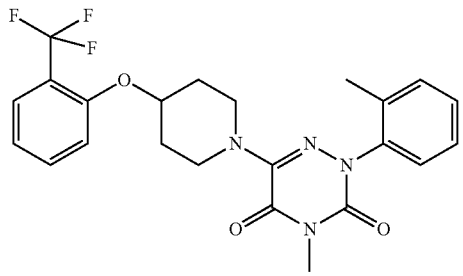 [SMILES: Cc1ccccc1-n1nc(N2CCC(Oc3ccccc3C(F)(F)F)CC2)c(=O)n(C)c1=O]

The compound 79 (solid) is prepared from the triazine 4l and from the intermediate 8c according to the synthesis method 1 in n-butanol (yield: 51%).

TLC silica gel 60 F 254 Merck, CH$_2$Cl$_2$-AcOEt: 90-10, Rf=0.52.

MP=106° C.

$^1$H NMR (CDCl$_3$) ppm: 1.95-2.10 (m, 4H), 2.22 (s, 3H), 3.43 (s, 3H), 3.52-3.57 (m, 4H), 4.69 (m, 1H), 6.98 (d, 1H, J=8.56 Hz), 6.99 (d, 1H, J=7.45 Hz), 7.27-7.34 (m, 4H), 7.46 (t, 1H, J=7.96 Hz), 7.57 (d, 1H, J=7.32 Hz).

MS (+ESI) m/z 461 (MH+)

Example 80

2-(4-fluoro-phenyl)-4-methyl-6-[4-(2-trifluoromethyl-phenoxy)-piperidin-1-yl]-2H-[1,2,4]triazine-3,5-dione (80)

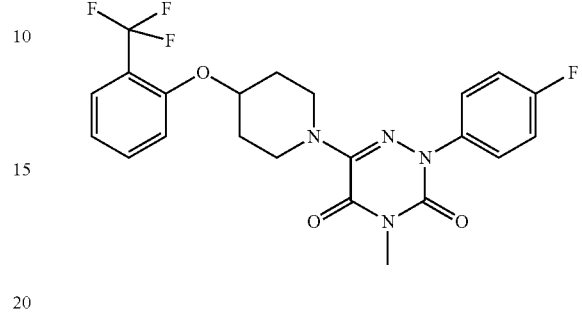

The compound 80 (solid) is prepared from the triazine 4m and from the intermediate 8c according to the synthesis method 1 in n-butanol (yield: 48%).

TLC silica gel 60 F 254 Merck, CH$_2$Cl$_2$-AcOEt: 95-5, Rf=0.64.

MP=111° C.

$^1$H NMR (CDCl$_3$) ppm: 1.99-2.12 (m, 4H), 3.42 (s, 3H), 3.51-3.60 (m, 2H), 3.60-3.69 (m, 2H), 4.72 (m, 1H), 6.97-7.02 (m, 2H), 7.11 (t, 2H, J=8.21 Hz), 7.47 (t, 1H, J=7.32 Hz), 7.53-7.60 (m, 3H).

MS (+ESI) m/z 465 (MH+)

Example 81

4-methyl-2-pyridin-3-yl-6-[4-(2-trifluoromethyl-phenoxy)-piperidin-1-yl]-2H-[1,2,4]triazine-3,5-dione (81)

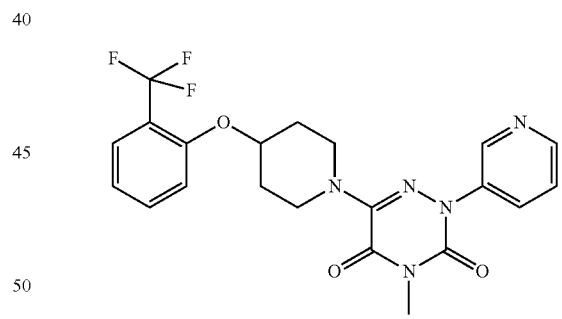

The compound 81 (solid) is prepared from the triazine 4n and from the intermediate 8c according to the synthesis method 1 in n-butanol (yield: 56%).

TLC silica gel 60 F 254 Merck, CH$_2$Cl$_2$-MeOH: 90-10, Rf=0.62.

MP=63° C.

$^1$H NMR (CDCl$_3$) ppm: 1.99-2.13 (m, 4H), 3.44 (s, 3H), 3.56-3.64 (m, 2H), 3.67-3.74 (m, 2H), 4.74 (m, 1H), 6.97-7.02 (m, 2H), 7.37 (ddd, 1H, J=0.6 Hz and J=4.67 Hz and J=8.21 Hz), 7.48 (dt, 1H, J=1.40 Hz and J=7.20 Hz), 7.59 (dd, 1H, J=1.40 Hz and J=8.08 Hz), 8.01 (ddd, 1H, J=1.51 Hz and J=2.65 Hz and J=7.96 Hz), 8.53 (dd, 1H, J=1.51 Hz and J=4.92 Hz), 8.93 (d, 1H, J=2.65 Hz).

MS (+ESI) m/z 448 (MH+)

Example 82

4-methyl-2-thiophen-3-yl-6-[4-(2-trifluoromethyl-phenoxy)-piperidin-1-yl]-2H-[1,2,4]triazine-3,5-dione (82)

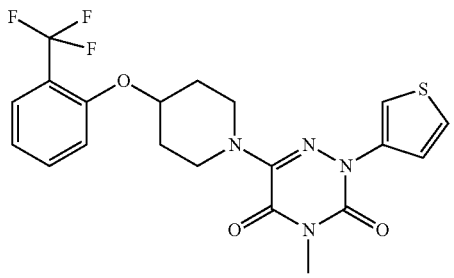 [SMILES: Cn1c(=O)c(N2CCC(Oc3ccccc3C(F)(F)F)CC2)nn(-c2ccsc2)c1=O]

The compound 82 (solid) is prepared from the triazine 4o and from the intermediate 8c according to the synthesis method 1 in n-butanol (yield: 57%).

TLC silica gel 60 F 254 Merck, $CH_2Cl_2$-AcOEt: 95-5, Rf=0.72.

MP=85° C.

$^1$H NMR (CDCl$_3$) ppm: 2.00-2.14 (m, 4H), 3.43 (s, 3H), 3.56-3.64 (m, 2H), 3.67-3.73 (m, 2H), 4.74 (m, 1H), 7.00 (t, 1H, J=6.69 Hz), 7.01 (d, 1H, J=8.46 Hz), 7.29 (dd, 1H, J=3.28 Hz and J=5.30 Hz), 7.48 (dt, 1H, J=1.64 Hz and J=7.83 Hz), 7.52 (dd, 1H, J=1.40 Hz and J=5.43 Hz), 7.59 (dd, 1H, J=1.51 Hz and J=8.08 Hz), 7.69 (dd, 1H, J=1.51 Hz and J=3.28 Hz).

MS (+ESI) m/z 453 (MH+)

Example 83

4-{4-methyl-3,5-dioxo-6-[4-(2-trifluoromethyl-phenoxy)-piperidin-1-yl]-4,5-dihydro-3H-[1,2,4]triazin-2-yl}-benzonitrile (83)

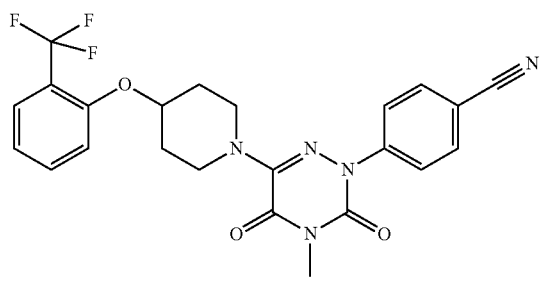 [SMILES: Cn1c(=O)c(N2CCC(Oc3ccccc3C(F)(F)F)CC2)nn(-c2ccc(C#N)cc2)c1=O]

The compound 83 (solid) is prepared from the triazine 4p and from the intermediate 8c according to the synthesis method 1 in n-butanol (yield: 60%).

TLC silica gel 60 F 254 Merck, $CH_2Cl_2$-AcOEt: 95-5, Rf=0.18.

MP=72° C.

$^1$H NMR (CDCl$_3$) ppm: 2.04-2.10 (m, 4H), 3.43 (s, 3H), 3.54-3.62 (m, 2H), 3.70-3.77 (m, 2H), 4.75 (m, 1H), 7.00 (d, 1H, J=7.58 Hz), 7.01 (t, 1H, J=6.06 Hz), 7.48 (t, 1H, J=7.70 Hz), 7.59 (d, 1H, J=7.95 Hz), 7.71 (d, 2H, J=8.84 Hz), 7.86 (d, 2H, J=8.84 Hz).

MS (+ESI) m/z 472 (MH+)

Example 84

2-(2-methoxy-phenyl)-4-methyl-6-[4-(2-trifluoromethyl-phenoxy)-piperidin-1-yl]-2H-[1,2,4]triazine-3,5-dione (84)

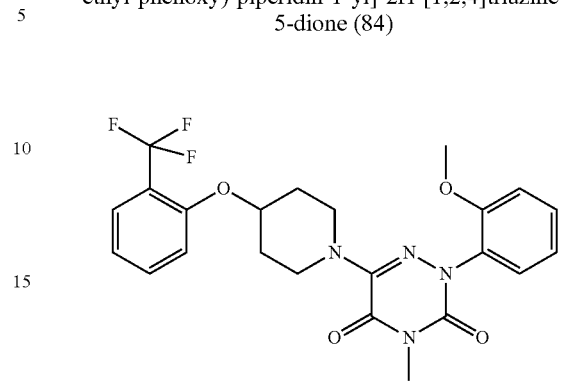

The compound 84 (solid) is prepared from the triazine 4q and from the intermediate 8c according to the synthesis method 1 in n-butanol (yield: 74%).

TLC silica gel 60 F 254 Merck, $CH_2Cl_2$-AcOEt: 95-5, Rf=0.32.

MP=128° C.

$^1$H NMR (CDCl$_3$) ppm: 1.94-2.10 (m, 4H), 3.41 (s, 3H), 3.45-3.59 (m, 4H), 3.84 (s, 3H), 4.67 (m, 1H), 6.95-7.05 (m, 4H), 7.31 (dd, 1H, J=1.64 Hz and J=7.58 Hz), 7.39 (td, 1H, J=1.89 Hz and J=7.70 Hz), 7.45 (td, 1H, J=1.64 Hz and J=7.96 Hz), 7.57 (dd, 1H, J=1.26 Hz and J=7.95 Hz).

MS (+ESI) m/z 477 (MH+)

Example 85

4-methyl-6-[4-(2-trifluoromethyl-phenoxy)-piperidin-1-yl]-2H-[1,2,4]triazine-3,5-dione (85)

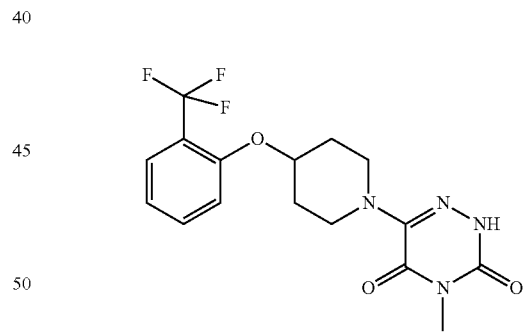

The compound 85 is prepared from the triazine 3a and from the intermediate 8c according to the synthesis method 1 in n-butanol. After deprotection of the nitrogen in position 2 (NaH, DMF, 20° C., 20 h), the compound 85 is obtained as a solid (yield: 77%).

TLC silica gel 60 F 254 Merck, $CH_2Cl_2$-AcOEt: 95-5, Rf=0.16.

MP=150° C.

$^1$H NMR (CDCl$_3$) ppm: 1.96-2.09 (m, 4H), 3.35 (s, 3H), 3.46-3.57 (m, 4H), 4.71 (m, 1H), 6.99 (t, 1H, J=7.32 Hz), 7.00 (d, 1H, J=8.59 Hz), 7.47 (t, 1H, J=7.56 Hz), 7.58 (d, 1H, J=8.08 Hz), 8.99 (s br, 1H).

MS (+ESI) m/z 371 (MH+)

Example 86

4-methyl-2-(2-oxo-cyclohexyl)-6-[4-(2-trifluoromethyl-phenoxy)-piperidin-1-yl]-2H-[1,2,4]triazine-3,5-dione (86)

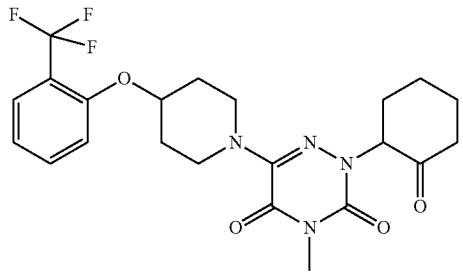 [SMILES: Cn1c(=O)c(N2CCC(Oc3ccccc3C(F)(F)F)CC2)nn(C2CCCCC2=O)c1=O]

The compound 86 (solid) is prepared from 2-chlorocyclohexanone and from the compound described for Example 85 according to the synthesis method 3 (yield: 31%).

TLC silica gel 60 F 254 Merck, $CH_2Cl_2$-MeOH: 95-5, Rf=0.63.

MP=65° C.

$^1$H NMR (CDCl$_3$) ppm: 1.64-1.90 (m, 2H), 1.93-2.18 (m, 6H), 2.19-2.49 (m, 3H), 2.54-2.62 (m, 1H), 3.34 (s, 3H), 3.46 (t, 2H, J=6.95 Hz), 3.48-3.61 (m, 2H), 4.68 (m, 1H), 5.14 (dd, 1H, J=5.93 Hz and J=12.88 Hz), 6.97-7.01 (m, 2H), 7.46 (t, 1H, J=7.32 Hz), 7.58 (d, 1H, J=8.46 Hz).

MS (+ESI) m/z 467 (MH+)

Example 87

4-methyl-2-(1-oxo-indan-2-yl)-6-[4-(2-trifluoromethyl-phenoxy)-piperidin-1-yl]-2H-[1,2,4]triazine-3,5-dione (87)

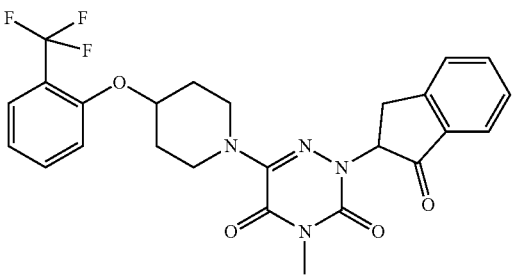 [SMILES: Cn1c(=O)c(N2CCC(Oc3ccccc3C(F)(F)F)CC2)nn(C2Cc3ccccc3C2=O)c1=O]

The compound 87 (solid) is prepared from 2-bromo-indan-1-one and from the compound described for Example 85 according to the synthesis method 3 (yield: 38%).

TLC silica gel 60 F 254 Merck, $CH_2Cl_2$-MeOH: 95-5, Rf=0.63.

MP=110° C.

$^1$H NMR (CDCl$_3$) ppm: 1.86-2.04 (m, 4H), 3.37 (s, 3H), 3.38-3.51 (m, 4H), 3.55-3.65 (m, 2H), 4.64 (m, 1H), 5.37 (m, 1H), 6.93-7.00 (m, 2H), 7.41-7.47 (m, 2H), 7.51 (d, 1H, J=8.21 Hz), 7.56 (d, 1H, J=7.96 Hz), 7.66 (td, 1H, J=1.40 Hz and J=7.58 Hz), 7.82 (d, 1H, J=7.70 Hz).

MS (+ESI) m/z 501 (MH+)

Example 88

2-[2-(2-ethoxy-ethoxy)-ethyl]-4-methyl-6-[4-(2-trifluoromethyl-phenoxy)-piperidin-1-yl]-2H-[1,2,4]triazine-3,5-dione (88)

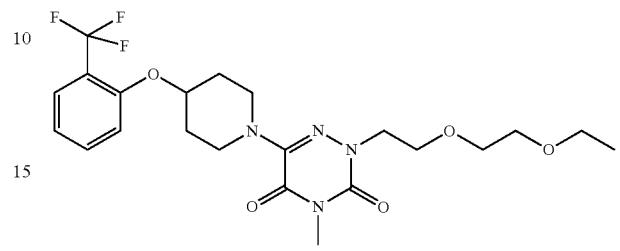

The compound 88 (solid) is prepared from 1-bromo-2-(2-ethoxy-ethoxy)-ethane and from the compound described for Example 85 according to the synthesis method 3 (yield 77%).

TLC silica gel 60 F 254 Merck, $CH_2Cl_2$-MeOH: 95-5, Rf=0.85.

MP=44° C.

$^1$H NMR (CDCl$_3$) ppm: 1.19 (t, 3H, J=7.07 Hz), 1.95-2.01 (m, 4H), 3.34 (s, 3H), 3.46-3.58 (m, 8H), 3.63-3.67 (m, 2H), 3.82 (t, 2H, J=5.81 Hz), 4.10 (t, 2H, J=5.81 Hz), 4.70 (m, 1H), 6.99 (t, 1H, J=7.20 Hz), 7.00 (d, 1H, J=7.07 Hz), 7.47 (t, 1H, J=7.96 Hz), 7.58 (d, 1H, J=7.83 Hz).

MS (+ESI) m/z 487 (MH+)

Example 89

2-(2-hydroxy-ethyl)-4-methyl-6-[4-(2-trifluoromethyl-phenoxy)-piperidin-1-yl]-2H-[1,2,4]triazine-3,5-dione (89)

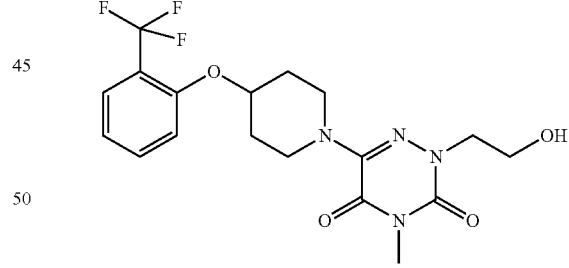

The compound 89 (solid) is prepared from 2-bromo-ethyl acetate and from the compound described for Example 85 according to the synthesis method 3 (yield: 68%).

TLC silica gel 60 F 254 Merck, $CH_2Cl_2$-MeOH: 95-5, Rf=0.85.

MP=112° C.

$^1$H NMR (CDCl$_3$) ppm: 1.97-2.10 (m, 4H), 2.41 (m, 1H), 3.36 (s, 3H), 3.46-3.54 (m, 2H), 3.54-3.62 (m, 2H), 3.94-3.99 (m, 2H), 4.11 (t, 2H, J=4.56 Hz), 4.71 (m, 1H), 7.00 (d, 1H, J=8.58 Hz), 7.00 (t, 1H, J=7.56 Hz), 7.48 (t, 1H, J=8.08 Hz), 7.59 (d, 1H, J=7.96 Hz).

MS (+ESI) m/z 415 (MH+)

Example 90

6-(4-(2-chloro-5-fluorophenoxy)piperidin-1-yl)-2-methyl-1,2,4-triazine-3,5(2H, 4H)-dione (90)

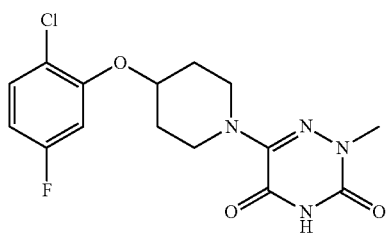

The compound 90 (white powder) is prepared from the triazine 2e and from the intermediate 8b according to the synthesis method 1 in toluene.

TLC silica gel 60 F 254 Merck, $CH_2Cl_2$-MeOH: 95-5, Rf=0.66.

MP=172° C.

$^1$H NMR (CDCl$_3$) ppm: 1.95-2.00 (m, 2H), 2.02-2.08 (m, 2H), 3.54 (s, 3H) 3.50-3.55 (m, 2H), 3.60-3.67 (m, 2H), 4.56 (m, 1H), 6.64 (m, 1H), 6.7 (dd, 1H), 7.32 (dd, 1H), 8.91 (s, 1H).

MS (+ESI) m/z 355 (MH+)

Example 91

6-(4-(2,5-dichlorophenoxy)piperidin-1-yl)-2-methyl-1,2,4-triazine-3,5(2H, 4H)-dione (91)

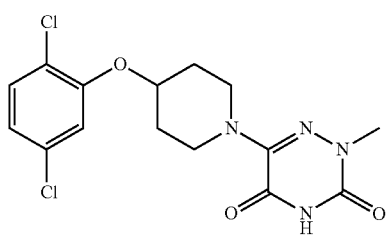 [SMILES: Cn1nc(N2CCC(Oc3cc(F)ccc3Cl)CC2)c(=O)[nH]c1=O]

The compound 91 (white solid) is prepared from the triazine 2e and from 4-(2,5-dichlorophenoxy)piperidine (obtained as under the preparative methods of intermediate 8a) according to the synthesis method 1 in toluene.

$^1$H NMR (CDCl$_3$) ppm: 1.95-2.08 (m, 4H), 3.50 (s, 3H), 3.50-3.53 (m, 2H), 3.61-3.67 (m, 2H), 4.57 (s, 1H), 6.90 (d, 1H, J=8.4 Hz), 6.94 (s, 1H), 7.29 (d, 1H, J=8.4 Hz), 8.75 (s, 1H).

MS (+ESI) m/z 371 (MH+)

Example 92

6-(4-(5-bromo-2-chlorophenoxy)piperidin-1-yl)-2-methyl-1,2,4-triazine-3,5(2H, 4H)-dione (92)

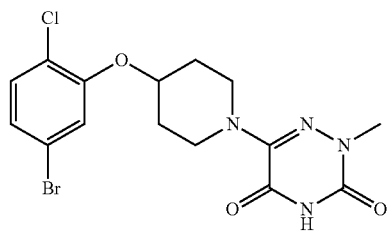 [SMILES: Cn1nc(N2CCC(Oc3cc(Br)ccc3Cl)CC2)c(=O)[nH]c1=O]

The compound 92 (yellow powder) is prepared from the triazine 2e and from 4-(5-bromo-2-chlorophenoxy)piperidine (obtained as under the preparative conditions of intermediate 8a) according to the synthesis method 1 in toluene.

$^1$H NMR (CDCl$_3$) ppm: 1.95-2.08 (m, 4H), 3.50 (s, 3H), 3.50-3.53 (m, 2H), 3.59-3.62 (m, 2H), 4.57 (s, 1H), 7.05 (d, 1H, J=8.8 Hz), 7.09 (s, 1H), 7.22-7.26 (m, 1H), 8.52 (s, 1H).

MS (+ESI) m/z 416 (MH+)

Example 93

6-(4-(2-bromo-4,5-difluorophenoxy)piperidin-1-yl)-2-methyl-1,2,4-triazine-3,5(2H, 4H)-dione (93)

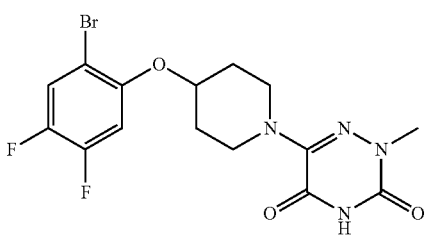 [SMILES: Cn1nc(N2CCC(Oc3cc(F)c(F)cc3Br)CC2)c(=O)[nH]c1=O]

The compound 93 (white solid) is prepared from the triazine 2e and from 4-(2-bromo-4,5-difluorophenoxy)piperidine (obtained as under the preparative conditions of intermediate 8a) according to the synthesis method 1 in toluene.

$^1$H NMR (CDCl$_3$) ppm: 1.94-2.09 (m, 4H), 3.51 (s, 3H), 3.51-3.58 (m, 2H), 3.61-3.67 (m, 2H), 4.48-4.52 (m, 1H), 6.78-6.83 (m, 1H), 7.39-7.44 (m, 1H), 8.22-8.29 (m, 1H).

MS (+ESI) m/z 418 (MH+)

Example 94

2-methyl-6-(4-(3-(trifluoromethyl)phenoxy)piperidin-1-yl)-1,2,4-triazine-3,5(2H, 4H)-dione (94)

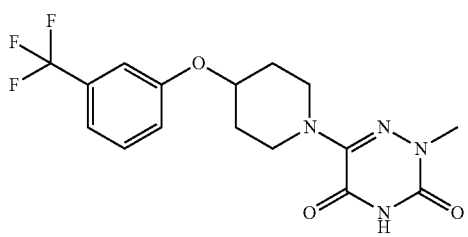 [SMILES: Cn1nc(N2CCC(Oc3cccc(C(F)(F)F)c3)CC2)c(=O)[nH]c1=O]

The compound 94 (white solid) is prepared from the triazine 2e and from 4-(3-(trifluoromethyl)phenoxy)piperidine (obtained as under the preparative conditions of intermediate 8a) according to the synthesis method 1 in toluene.

$^1$H NMR (CDCl$_3$) ppm: 1.88-1.98 (m, 2H), 2.03-2.13 (m, 2H), 3.39-3.45 (m, 2H), 3.51 (s, 3H), 3.68-3.73 (m, 2H), 4.57-4.59 (m, 1H), 7.09 (d, 1H, J=8.4 Hz), 7.22 (d, 1H, J=7.2 Hz), 7.41 (t, 1H, J=8 Hz), 8.34-8.37 (m, 1H).

MS (+ESI) m/z 371 (MH+)

Pharmacological Evaluation

In vitro: Human SCD-1 enzymatic activity from microsomes of HepG2 cells after treatment with inhibitory compounds (inhibition %).

Human hepatocarcinoma HepG2 cells (ATCC, HB-8065) are grown to confluence and then trypsinized. The cell pellet is taken up in 10 mM Tris buffer (pH 7.4), saccharose (250 mM) DTT (1 mM) and then the cells are lyzed by sonication. The microsomes are obtained after centrifugation at 10,000 g for 20 minutes a 4° C. followed by centrifugation of the supernatant at 100,000 g for 60 minutes a 4° C. The pellet is taken up in 10 mM Tris buffer (pH 7.4) saccharose (250 mM) at 4° C. and the microsomal proteins are assayed and stored at −196° C. (liquid nitrogen).

The enzymatic reaction measures the conversion of stearic acid (a C18:0 fatty acid) into oleic acid (C18:1 fatty acid) by SCD-1. The enzymatic reaction is started by adding 125 µg of microsomal fraction of HepG2 cells to tubes (total reaction volume of 500 µl) containing 62 µM of stearic acid (45 µM of stearic acid and 17 µM of [$^{14}$C] stearic acid) in a phosphate buffer at 100 mM (pH 7.16) with 7.2 mM of ATP, 0.54 mM of CoA, 6 mM of MgCl$_2$, 0.8 mM of NADH and the inhibitory compound or the carrier (0.1% DMSO). The tubes are incubated for 20 minutes at 37° C. and the enzymatic reaction is then stopped by adding KOH (12%) and saponification for 30 minutes at 80° C. After acidification (3N HCl), the fatty acids are extracted twice with ethyl ether, evaporated under nitrogen before being taken up with a methanol/dichloromethane (3:1) mixture. The product of the reaction (C18:1) is separated from the substrate of the reaction (C18:0) by HPLC (Perkin Elmer, C18 reverse phase column) coupled to a on-line radioactivity detector (FlowOne). Enzymatic activity is calculated in picomoles of stearic acid converted into oleic acid per minute and per mg of protein. For each inhibitory compound, an inhibition % is determined relatively to the reference enzymatic activity (carrier 0.1% DMSO). Sterculic acid is the reference inhibitory compound (Gomez F. E., Bauman D. E., Ntambi J. M., Fox B. G. Effects of sterculic acid on stearoyl-CoA desaturase in differentiating 313-L1 adipocytes. *Biochem Biophys Res Commun.* 300 316-326 (2003)).

TABLE 10

Human SCD-1 enzymatic activity inhibition % at 10 µM).

| Example | HSCD-1 (HEPG2) % inh. (10 µM) |
|---|---|
| Sterculic acid | 100 |
| 1 | 11 |
| 2 | 63 |
| 3 | 90 |
| 4 | 77 |
| 5 | 43 |
| 6 | 73 |
| 11 | 92 |
| 12 | 71 |
| 13 | 75 |
| 14 | 74 |

TABLE 10-continued

Human SCD-1 enzymatic activity inhibition % at 10 µM).

| Example | HSCD-1 (HEPG2) % inh. (10 µM) |
|---|---|
| 15 | 74 |
| 16 | 57 |
| 19 | 57 |
| 23 | 73 |
| 25 | 70 |
| 27 | 82 |
| 28 | 50 |
| 29 | 71 |
| 30 | 86 |
| 31 | 73 |
| 33 | 48 |
| 42 | 80 |
| 47 | 84 |
| 48 | 64 |
| 55 | 65 |
| 57 | 71 |
| 64 | 57 |
| 69 | 84 |
| 70 | 66 |
| 71 | 50 |
| 74 | 60 |
| 76 | 62 |
| 79 | 54 |
| 80 | 87 |
| 81 | 98 |
| 82 | 100 |
| 83 | 79 |
| 84 | 53 |
| 85 | 95 |
| 86 | 90 |
| 88 | 48 |
| 89 | 100 |

The invention also relates to the compounds of general formula (I) for their use as drugs intended for treating diseases requiring inhibitors of SCD-1 enzyme activity.

The invention also relates to compounds of general formula (I) for their use as drugs intended for treating diseases such as obesity, diabetic dyslipidemia, hypertriglyceridemia, hypercholesterolemia, the metabolic syndrome, atherosclerosis, hepatic steatosis, cardiovascular risks.

The invention also extends to compounds of general formula (I) for their use as drugs intended for treating pathologies related to lipid disorders of the skin.

The invention also relates to compounds of general formula (I) for their use as drugs intended for treating diseases such as acne, psoriasis, hirsutism.

The invention claimed is:

1. A compound of formula I wherein:

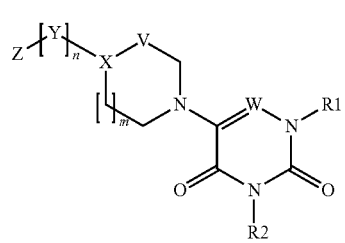

W represents nitrogen

R1 and R2 represent:

a hydrogen or a linear or branched C$_1$-C$_7$ alkyl or alkenyl radical, with the proviso that R1 and R2 are not simultaneously hydrogen, or, a C$_1$-C$_3$ alkyl radical substituted with groups selected from:
trifluoromethyl, nitrile, hydroxy, C$_1$-C$_3$ alkoxy, C$_3$-C$_6$ alkoxyalkoxy, indolyl, thiophenyl, oxothiophenyl, C$_1$-C$_3$ N-alkyl or N-dialkylcarbamoyl groups or,
phenyl or aroyl or benzyloxy or N-arylcarbamoyl groups, for which the phenyl ring is optionally substituted with one or more groups selected from linear or branched C$_1$-C$_4$ alkyl, nitro groups, or halogen atoms,
a phenyl or pyridyl or naphthyl or thiophenyl group optionally substituted with one or more groups selected from halogen atoms, nitro, nitrile, trifluoromethyl, vinyl, methylsulfanyl, linear or branched C$_1$-C$_4$ alkyl, linear or branched C$_1$-C$_3$ alkoxy, phenyl, C$_1$-C$_3$ N-mono- or di-alkylcarbamoyl, or C$_1$-C$_4$ alkylcarboxamido groups,
a C$_5$-C$_6$ 2-oxocycloalkyl radical optionally fused with a phenyl group,
m and n are equal to 1
V represents CH$_2$
X—Y represents —N—(C═O)—, —CH—CH$_2$—, —CH—O—, —CH—(C═O)—,
Z represents a phenyl group substituted with one or more trifluoromethyl groups, halogen atoms, linear or branched C$_1$-C$_4$ alkyl, linear or branched C$_1$-C$_3$ alkoxy groups.

2. The compound according to claim 1, corresponding to the formula I wherein:
W represents nitrogen
R1 and R2 represent:
a hydrogen or a linear or branched C$_1$-C$_7$ alkyl radical, with the proviso that R1 and R2 are not simultaneously hydrogen, or,
a C$_1$-C$_3$ alkyl radical substituted with groups selected from trifluoromethyl, nitrile, hydroxy, C$_1$-C$_3$ alkoxy, C$_3$-C$_6$ alkoxyalkoxy, indolyl, oxothiophenyl, C$_1$-C$_3$ N-alkyl or N-dialkylcarbamoyl groups,
a phenyl or pyridyl or naphthyl or thiophenyl group optionally substituted with one or more groups selected from halogen atoms, nitro, nitrile, trifluoromethyl, vinyl, methylsulfanyl, linear or branched C$_1$-C$_4$ alkyl, linear or branched C$_1$-C$_3$ alkoxy, C$_1$-C$_3$ N-mono- or di-alkylcarbamoyl, or C$_1$-C$_4$ alkylcarboxamido groups,
a C$_5$-C$_6$ 2-oxocycloalkyl radical optionally fused with a phenyl group,
m and n are equal to 1
V represents CH$_2$
X—Y represents —N—(C═O)—, —CH—O—,
Z represents a phenyl group substituted with one or more trifluoromethyl groups, halogen atoms, or linear or branched C$_1$-C$_4$ alkyl groups.

3. The compound according to claim 1, corresponding to the formula I wherein:
W represents nitrogen,
R1 represents:
a hydrogen or linear or branched C$_1$-C$_5$ alkyl radical or,
a C$_1$-C$_3$ alkyl radical substituted with groups selected from trifluoromethyl, nitrile, hydroxy, C$_1$-C$_3$ alkoxy, C$_3$-C$_6$ alkoxyalkoxy, indolyl, oxothiophenyl, or C$_1$-C$_3$ N-alkylcarbamoyl groups,
a phenyl or pyridyl or naphthyl or thiophenyl group optionally substituted with one or more groups selected from halogen atoms, nitro, nitrile, trifluoromethyl, vinyl, methylsulfanyl, linear or branched C$_1$-C$_4$ alkyl, linear or branched C$_1$-C$_3$ alkoxy, phenyl, C$_1$-C$_3$ N-mono- or di-alkylcarbamoyl, or C$_1$-C$_4$ alkylcarboxamido groups,
a C$_5$-C$_6$ 2-oxocycloalkyl radical,
R2 represents: a linear or branched C$_1$-C$_7$ alkyl radical,
m and n are equal to 1,
V represents CH$_2$,
X—Y represents —N—(C═O)—, —CH—O—,
Z represents a phenyl group substituted with one or more trifluoromethyl groups, halogen atoms, or linear C$_1$-C$_4$ alkyl groups.

4. The compound according to claim 1, corresponding to the formula I wherein:
W represents nitrogen,
R1 represents:
a hydrogen or a linear or branched C$_1$-C$_5$ alkyl radical or,
a C$_1$-C$_3$ alkyl radical substituted with groups selected from trifluoromethyl, nitrile, hydroxy, C$_1$-C$_3$ alkoxy, C$_3$-C$_6$ alkoxyalkoxy, indolyl, oxothiophenyl, or C$_1$-C$_3$ N-alkylcarbamoyl groups,
a phenyl or pyridyl or thiophenyl group possibly substituted with one or more groups selected from halogen atoms, nitrile, linear or branched C$_1$-C$_4$ alky, or linear or branched C$_1$-C$_3$ alkoxygroups,
a C$_6$ 2-oxocycloalkyl radical,
R2 represents a methyl or heptyl,
m and n are equal to 1,
V represents CH$_2$,
X—Y represents —N—(C═O)—, —CH—O—,
Z represents a phenyl group substituted with one or more trifluoromethyl groups, halogen atoms or linear C$_1$-C$_4$ alkyl groups.

5. The compound according to claim 1, selected from:
4-heptyl-2-methyl-6-[4-(2-trifluoromethyl-benzoyl)-piperazin-1-yl]-2H-[1,2,4]triazine-3,5-dione,
2-methyl-6-[4-(2-trifluoromethyl-benzoyl)-piperazin-1-yl]-2H-[1,2,4]triazine-3,5-dione,
4-methyl-2-(4,4,4-trifluoro-butyl)-6-[4-(2-trifluoromethyl-benzoyl)-piperazin-1-yl]-2H-[1,2,4]triazine-3,5-dione,
4-methyl-6-[4-(2-trifluoromethyl-benzoyl)-piperazin-1-yl]-2H-[1,2,4]triazine-3,5-dione,
2,4-dimethyl-6-[4-(2-trifluoromethyl-benzoyl)-piperazin-1-yl]-2H-[1,2,4]triazine-3,5-dione,
2,4-dimethyl-6-[4-(2-trifluoromethyl-phenoxy)-piperidin-1-yl]-2H-[1,2,4]triazine-3,5-dione,
3-{4-heptyl-3,5-dioxo-6-[4-(2-trifluoromethyl-phenoxy)-piperidin-1-yl]-4,5-dihydro-3H-[1,2,4]triazin-2-yl}-propionitrile,
2-butyl-4-methyl-6-[4-(2-trifluoromethyl-phenoxy)-piperidin-1-yl]-2H-[1,2,4]triazine-3,5-dione,
N-methyl-2-{4-methyl-3,5-dioxo-6-[4-(2-trifluoromethyl-phenoxy)-piperidin-1-yl]-4,5-dihydro-3H-[1,2,4]triazin-2-yl}-acetamide,
2-(2-ethoxy-ethyl)-4-methyl-6-[4-(2-trifluoromethyl-phenoxy)-piperidin-1-yl]-2H-[1,2,4]triazine-3,5-dione,
2-[2-(1H-Indol-3-yl)-ethyl]-4-methyl-6-[4-(2-trifluoromethyl-phenoxy)-piperidin-1-yl]-2H-[1,2,4]triazine-3,5-dione,
4-methyl-2-(4-oxo-4-thiophen-2-yl-butyl)-6-[4-(2-trifluoromethyl-phenoxy)-piperidin-1-yl]-2H-[1,2,4]triazine-3,5-dione,
3-{6-[4-(2-chloro-phenoxy)-piperidin-1-yl]-4-methyl-3,5-dioxo-4,5-dihydro-3H-[1,2,4]triazin-2-yl}-propionitrile,

- 6-[4-(2-chloro-phenoxy)-piperidin-1-yl]-4-methyl-2-(4,4,4-trifluoro-butyl)-2H-[1,2,4]triazine-3,5-dione,
- 6-[4-(2-chloro-phenoxy)-piperidin-1-yl]-2,4-dimethyl-2H-[1,2,4]triazine-3,5-dione,
- 6-[4-(2-fluoro-phenoxy)-piperidin-1-yl]-2,4-dimethyl-2H-[1,2,4]triazine-3,5-dione,
- 6-[4-(2-chloro-5-trifluoromethyl-phenoxy)-piperidin-1-yl]-2,4-dimethyl-2H-[1,2,4]triazine-3,5-dione,
- 6-[4-(2-chloro-5-fluoro-phenoxy)-piperidin-1-yl]-2,4-dimethyl-2H-[1,2,4]triazine-3,5-dione,
- 2,4-dimethyl-6-(4-o-tolyloxy-piperidin-1-yl)-2H-[1,2,4]triazine-3,5-dione,
- 6-[4-(4-fluoro-phenoxy)-piperidin-1-yl]-2,4-dimethyl-2H-[1,2,4]triazine-3,5-dione,
- 6-[4-(5-fluoro-2-trifluoromethyl-benzoyl)-piperazin-1-yl]-2,4-dimethyl-2H-[1,2,4]triazine-3,5-dione,
- 6-[4-(5-fluoro-2-trifluoromethyl-benzoyl)-piperazin-1-yl]-4-methyl-2-(4,4,4-trifluoro-butyl)-2H-[1,2,4]triazine-3,5-dione,
- 6-[4-(5-fluoro-2-trifluoromethyl-benzoyl)-piperazin-1-yl]-4-methyl-2-(3-methyl-butyl)-2H-[1,2,4]triazine-3,5-dione,
- 6-[4-(5-fluoro-2-trifluoromethyl-benzoyl)-piperazin-1-yl]-4-methyl-2H-[1,2,4]triazine-3,5-dione,
- 6-[4-(4-fluoro-2-trifluoromethyl-benzoyl)-piperazin-1-yl]-4-methyl-2H-[1,2,4]triazine-3,5-dione,
- 2-butyl-4-methyl-6-[4-(2-trifluoromethyl-benzoyl)-piperazin-1-yl]-2H-[1,2,4]triazine-3,5-dione,
- 6-[4-(2-chloro-phenoxy)-piperidin-1-yl]-4-heptyl-2H-[1,2,4]triazine-3,5-dione,
- 4-methyl-2-o-tolyl-6-[4-(2-trifluoromethyl-phenoxy)-piperidin-1-yl]-2H-[1,2,4]triazine-3,5-dione,
- 2-(4-fluoro-phenyl)-4-methyl-6-[4-(2-trifluoromethyl-phenoxy)-piperidin-1-yl]-2H-[1,2,4]triazine-3,5-dione,
- 4-methyl-2-pyridin-3-yl-6-[4-(2-trifluoromethyl-phenoxy)-piperidin-1-yl]-2H-[1,2,4]triazine-3,5-dione,
- 4-methyl-2-thiophen-3-yl-6-[4-(2-trifluoromethyl-phenoxy)-piperidin-1-yl]-2H-[1,2,4]triazine-3,5-dione,
- 4-{4-methyl-3,5-dioxo-6-[4-(2-trifluoromethyl-phenoxy)-piperidin-1-yl]-4,5-dihydro-3H-[1,2,4]triazin-2-yl}-benzonitrile,
- 2-(2-methoxy-phenyl)-4-methyl-6-[4-(2-trifluoromethyl-phenoxy)-piperidin-1-yl]-2H-[1,2,4]triazine-3,5-dione,
- 4-methyl-6-[4-(2-trifluoromethyl-phenoxy)-piperidin-1-yl]-2H-[1,2,4]triazine-3,5-dione,
- 4-methyl-2-(2-oxo-cyclohexyl)-6-[4-(2-trifluoromethyl-phenoxy)-piperidin-1-yl]-2H-[1,2,4]triazine-3,5-dione,
- 2[2-(2-ethoxy-ethoxy)-ethyl]-4-methyl-6-[4-(2-trifluoromethyl-phenoxy)-piperidin-1-yl]-2H-[1,2,4]triazine-3,5-dione, or
- 2-(2-hydroxy-ethyl)-4-methyl-6-[4-(2-trifluoromethyl-phenoxy)-piperidin-1-yl]-2H-[1,2,4]triazine-3,5-dione.

6. A method for preparing a compound of formula I as defined in claim 1, wherein a compound of formula II

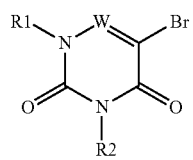

with W, R1 and R2 being defined in claim 1, is fused with a compound of formula III

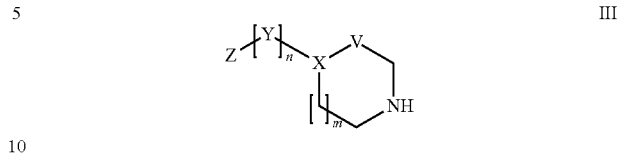

for which m, n, X, Y, V, and Z, are as defined in claim 1.

7. A method for preparing a compound of formula I as defined in claim 1, for which X represents a nitrogen, wherein a compound of formula IV

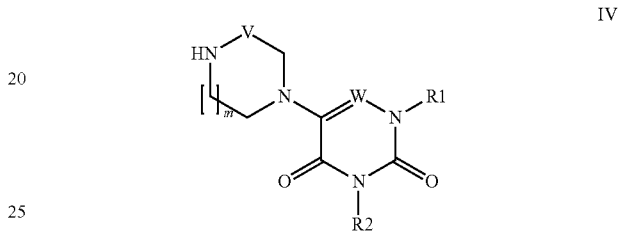

with m, V, W, R1 and R2 being defined in claim 1, is fused with a compound of general formula V

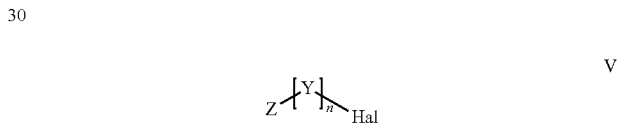

wherein Hal represents a halogen,
n represents 0 or 1, and
when n=1, Y represents —(C=O)—, —CH$_2$—, or —O—(C=O)—,
when n=0, Y represents —CH=CH—(C=O)—, or —C—(CH(CH$_3$)$_2$)—(C=O)—
and Z is defined in claim 1.

8. A method for preparing a compound of formula I as defined in claim 1, wherein W represents a nitrogen, and wherein a compound of formula VI

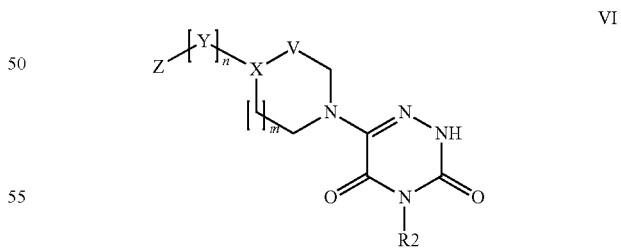

with X, Y, V, Z, m, n and R2 being defined in claim 1, is alkylated by a halogenated compound of formula R1Hal, wherein Hal represents a halogen and R1 is defined in claim 1.

9. A method for treating obesity or type-2 diabetes which comprises administering a compound of formula (I) as defined in claim 1 to a patient in need thereof.

10. A pharmaceutical composition comprising a compound of formula (I) as defined according to claim 1 or addition salts with pharmaceutically acceptable bases and acids, in association with any suitable excipient.

11. A method for preparing a compound according to claim 1, wherein a compound of formula II

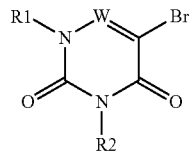

with W, R1 and R2 being defined in formula I, is fused with a compound of formula III

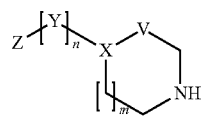

for which m, n, X, Y, V, and Z, are defined in claim 1.

12. A method for preparing a compound according to claim 2, wherein a compound of formula II

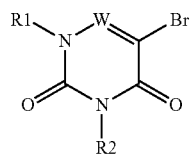

with W, R1 and R2 being defined in claim 2, is fused with a compound of formula III

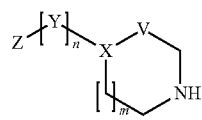

for which m, n, X, Y, V, and Z, are as described in claim 2.

13. A method for preparing compound according to claim 3, wherein a compound of formula II

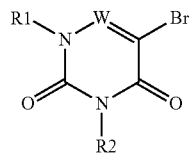

with W, R1 and R2 being defined in claim 3, is fused with a derivative of general formula III

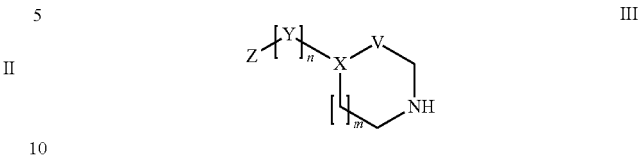

for which m, n, X, Y, V, and Z, are defined in claim 3.

14. A method for preparing a compound of formula I according to claim 4, wherein a compound of formula II

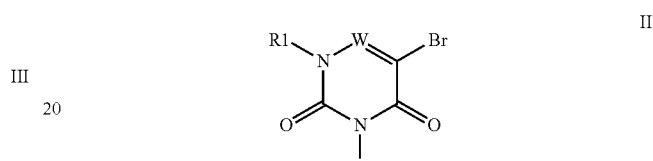

with W, R1 and R2 being defined in claim 4, is fused with a compound of formula III

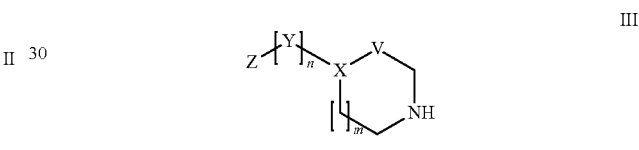

for which m, n, X, Y, V, and Z, are defined in claim 4.

15. The method of claim 3, wherein R2 represents methyl.

16. The method of claim 6, wherein the reaction is conducted in the presence of triethylamine in n-butanol or toluene or dimethylformamide.

17. The method of claim 7, wherein the reaction is conducted in the presence of triethylamine in dichloromethane or in toluene when Y is —CH$_2$—.

18. The method of claim 8, wherein the reaction is conducted in the presence of NaH or tBuOK in dimethylformamide.

19. The method of claim 11, wherein the reaction is conducted in the presence of triethylamine in n-butanol or toluene or dimethylformamide.

20. The method of claim 12, wherein the reaction is conducted in the presence of triethylamine in n-butanol or toluene or dimethylformamide.

21. The method of claim 13, wherein the reaction is conducted in the presence of triethylamine in n-butanol or toluene or dimethylformamide.

22. The method of claim 14, wherein the reaction is conducted in the presence of triethylamine in n-butanol or toluene or dimethylformamide.

* * * * *